United States Patent
Weinhäusel

(10) Patent No.: US 10,156,570 B2
(45) Date of Patent: *Dec. 18, 2018

(54) LUNG CANCER DIAGNOSTIC METHOD AND MEANS

(71) Applicant: AIT AUSTRIAN INSTITUTE OF TECHNOLOGY GMBH, Vienna (AT)

(72) Inventor: Andreas Weinhäusel, Neckenmarkt (AT)

(73) Assignee: AIT Austrian Institute of Technology GMBH, Vienna (AT)

( * ) Notice: Subject to any disclaimer, the term of this patent is extended or adjusted under 35 U.S.C. 154(b) by 68 days.

This patent is subject to a terminal disclaimer.

(21) Appl. No.: 14/893,712

(22) PCT Filed: May 23, 2014

(86) PCT No.: PCT/EP2014/060667
§ 371 (c)(1),
(2) Date: Nov. 24, 2015

(87) PCT Pub. No.: WO2014/187959
PCT Pub. Date: Nov. 27, 2014

(65) Prior Publication Data
US 2016/0109453 A1    Apr. 21, 2016

(30) Foreign Application Priority Data

May 24, 2013  (EP) .................................... 13169067

(51) Int. Cl.
*G01N 33/50* (2006.01)
*G01N 33/574* (2006.01)

(52) U.S. Cl.
CPC ... *G01N 33/57423* (2013.01); *G01N 2800/60* (2013.01)

(58) Field of Classification Search
None
See application file for complete search history.

(56) References Cited

U.S. PATENT DOCUMENTS

2002/0099012 A1* 7/2002 Wang ................. A61K 39/0011
424/184.1
2004/0235071 A1  11/2004 Lightcap et al.
2005/0220795 A1* 10/2005 Wittrup ................... C07K 16/40
424/146.1
2010/0055724 A1*  3/2010 Taylor .................. G01N 33/574
435/7.92
2012/0045766 A1*  2/2012 Nakamura ........... A61K 31/713
435/6.12

FOREIGN PATENT DOCUMENTS

WO    WO2012/142208    10/2012

OTHER PUBLICATIONS

Cha et al. (Cancer Epidemiology, 33: 281-287, 2009).*
Kim et al. (Cancer Res., 67(20): 9616-9622, 2007).*
Deng et al. (Cancer Chemother. Pharmacol., 54: 301-307, 2004).*
McClelland et al. (AJP, 174(2): 638-646, 2009).*
Chen et al. (Cancer Chemother Pharmacol, 61: 979-987, 2008).*
Penning et al. (Biochem. J., 351, 67-77: 2000).*
Chapman, C.J. et al.: "Autoantibodies in lung cancer: possibilities for early detection and subsequent cure", Thorax, (2008), 63, pp. 228-233.
Farlow, E. et al.: "Development of a Multiplexed Tumor-Associated Autoantibody-Based Blood Test for the Detection of Non-Small Cell Lunch Cancer", Clinical Cancer Research, vol. 16(13), (Jul. 1, 2010), pp. 3452-3462.
Gnjatic, S. et al.: "Seromic analysis of antibody responses in non-small cell lung cancer patients and healthy donors using conformational protein arrays", Journal of Immunological Methods, vol. 341, (2009), pp. 50-58.
Huang, L et al.: "Proteomics-based identification of secreted protein dihydrodiol dehydrogenase as a novel serum markers of non-small cell lung cancer", Lung Cancer, (2006), 54, pp. 87-94.
Zhong, L. et al.: "Profiling Tumor-Associated Antibodies for Early Detection of Non-small Cell Lung Cancer", Journal of Thoracic Oncology, vol. 1, No. 6, (Jul. 2006), pp. 513-519.
Backes et al., "Immunogenicity of Autoantigens", BMC Genomics, 12:340, (2011), pp. 1-13.
Greenbaum et al., "Comparing Protein Abundance and mRNA Expression Levels on a Genomic Scale", Genome Biology, 4:117, (2003).
Gygi et al., "Correlation between Protein and mRNA Abundance in Yeast", Molecular and Cellular Biology, 19:3, (Mar. 1999), pp. 1720-1730.

* cited by examiner

*Primary Examiner* — Nelson B Moseley, II
(74) *Attorney, Agent, or Firm* — Norton Rose Fulbright US LLP

(57) ABSTRACT

The present invention discloses a method of diagnosing lung cancer by using specific markers from a set, having diagnostic power for lung cancer diagnosis and distinguishing lung cancer types in diverse samples.

10 Claims, No Drawings

LUNG CANCER DIAGNOSTIC METHOD AND MEANS

CROSS-REFERENCE TO RELATED APPLICATIONS

This application is a national phase application under 35 U.S.C. § 371 of International Application No. PCT/EP2014/060667 filed 23 May 2014, which claims priority to European Patent Application No. 13169067.9 filed 24 May 2013. The entire contents of each of the above-referenced disclosures is specifically incorporated by reference herein without disclaimer.

The present invention relates to cancer diagnostic methods and means therefor.

Neoplasms and cancer are abnormal growths of cells. Cancer cells rapidly reproduce despite restriction of space, nutrients shared by other cells, or signals sent from the body to stop reproduction. Cancer cells are often shaped differently from healthy cells, do not function properly, and can spread into many areas of the body. Abnormal growths of tissue, called tumors, are clusters of cells that are capable of growing and dividing uncontrollably. Tumors can be benign (noncancerous) or malignant (cancerous). Benign tumors tend to grow slowly and do not spread. Malignant tumors can grow rapidly, invade and destroy nearby normal tissues, and spread throughout the body. Malignant cancers can be both locally invasive and metastatic. Locally invasive cancers can invade the tissues surrounding it by sending out "fingers" of cancerous cells into the normal tissue. Metastatic cancers can send cells into other tissues in the body, which may be distant from the original tumor. Cancers are classified according to the kind of fluid or tissue from which they originate, or according to the location in the body where they first developed. All of these parameters can effectively have an influence on the cancer characteristics, development and progression and subsequently also cancer treatment. Therefore, reliable methods to classify a cancer state or cancer type, taking diverse parameters into consideration is desired.

In cancer-patients serum-antibody profiles change as well as autoantibodies against the cancerous tissue are generated. Those profile-changes are highly potential of tumor associated antigens as markers for early diagnosis of cancer. The immunogenicity of tumor associated antigens are conferred to mutated amino acid sequences, which expose an altered non-self epitope. Other explanations for its immunogenicity include alternative splicing, expression of embryonic proteins in adulthood, deregulation of apoptotic or necrotic processes and abnormal cellular localizations (e.g. nuclear proteins being secreted). Other explanations are also implicated of this immunogenicity, including alternative splicing, expression of embryonic proteins in adulthood, deregulation of apoptotic or necrotic processes, abnormal cellular localizations (e.g. nuclear proteins being secreted). Examples of epitopes of the tumour-restricted antigens, encoded by intron sequences (i.e. partially unspliced RNA were translated) have been shown to make the tumor associated antigen highly immunogenic. However until today technical prerequisites performing an efficient marker screen were lacking.

Chapman et al., 2008. Thorax, 63(3), 228-233 investigated autoantibodies against p53, c-myc, HER2, NY-ESO-1, CAGE, MUC1 and GBU4-5 by ELISA in lung cancer.

Zhong et al., 2006. Journal of Thoracic Oncology, 1(6), 513-519 describes profiling tumor-associated antibodies in non-small cell lung cancer.

Gnjatic et al., 2009. J. Immunol Meth, 341(1-2), 50-58 describe serum antibodies in non-small cell lung cancer.

US 2004/235071 A1 describes methods for diagnostic or prognostic assays by detecting several marker proteins indicative of cancer.

Farlow et al., 2010. Clin Cancer Res, 16(13), 3452-3461 describe blood tests for detecting autoantibodies in non-small cell lung cancer.

Huang et al., 2006, Lung Cancer, 54(1), 87-94 the proteomics based identification of the secreted protein dihydrodiol dehydrogenase, DDH, as serum marker in non-small cell lung carcinoma. DDH (Swissprot database id P52895) is also disclosed as Aldo-keto reductase family 1 member C2 and is different from other members of this family, such as AKR1C4.

WO 2012/142208 A1 describes AKR1C3 inhibitors and monoclonal antibodies against AKR1C3.

None of these documents describe the present invention.

The object of the present invention is therefore to provide improved marker sequences and the diagnostic use thereof for the treatment of lung cancer.

The provision of specific markers permits a reliable diagnosis and stratification of patients with lung cancer, in particular by means of a protein biochip.

The invention therefore relates to the use of marker proteins for the diagnosis of lung cancer, wherein at least one marker protein is selected from the marker proteins of List 1.

List 1: Marker Proteins Given by their Protein Symbol.
ACO2 (includes EG:11429), ADH5 (includes EG:100145871), ADI1 (includes EG:104923), AGRN, AKAP13, AKR1C4, ALDOA, APBB1, ARHGDIA, ARHGEF1, ARHGEF18, ATXN2L, BAZ1A, BCAS2, C10orf35, CCDC88C, CD81, CEP250, CLDN5, COL4A1, COMP, COPE, CUL7, D2HGDH, DUSP2, EDARADD, EIF3M, EPS8, ERCC5, EXOSC10, FAM192A, FAM21A/FAM21C, FBF1, FGFR3, FPGS, FYN, G3BP2, GABBR1, GGA2, GLOD4, GOLGA7, HERC2, HLA-E, HMGB2, IGHG1, KCTD15, KIF5A, LRP1 (includes EG:16971), MC1R, MDFIC, MED20, MEGF6, MUC2 (includes EG:4583), NECAP1, NEDD9, NFKB1, NFKBIA, NFYA, NLRC5, NLRP1, NOL11, PCBP1, PLCG1, PPP1CA, PPP6R1, PRMT1, PSAP, PSMC4, RCSD1, RPS25, RRP1B, RSBN1, SBK1, SETD2, SFN, SLC9A3R2, SMYD5, SNCB, SNRNP48, SREBF2, SRPR, SRRM2, SUMO1P3, TBCB, TMEM222, TOMM20 (includes EG:100043869), TP53 (includes EG:22059), TP53BP2, TRAK1, TRIM28, TRIM78P, TRIOBP, TXN2, UQCRC1, UTP14A, VIMP, WNK2, ZC3H13, ZEB1, ACBD5, ADAMDEC1, AKAP8, ANKRD12, AP1G1, AP1M1, ARFRP1, ATG16L1, AZGP1, BACE1, BICD2, BRD2, C11orf30, C1QTNF4, CBX4, CD74, CHST10, CLIP1, CLTC, CLUAP1, COL6A3, COPA, CTBP2, DAGLB, DDX54, DLG5, DNAJB1, EML3, FBXW5, FLOT1, FOSL2, GGA1 (includes EG:106039), HAUS7, HOXB2, HSPA8, HSPG2, ID3, IL1B, IMPDH2, ISOC1, ITFG3, KRT73, LOC341056, LYSMD2, MED11 (includes EG:100148504), MED4 (includes EG:29079), METAP2, NAP1L1, NFATC1, NOTCH2, NPHP3, NR1H2, NSMCE1, NUMBL, OTUD4, PARP14, PFKL, PKM, POTEE/POTEF, PPP1R15B, PPP4C, PRC1 (includes EG:233406), PRRC2A, PSMA1, PSMB5, PSME4, QARS, RAI1, RAP2B, RASAL3, RECQL, RNF39, RPS19, SCAF1, SCML4, SMG5, SNRPF, STAG2, TAPBPL, TBX21, TFRC, TGOLN2, TIAM1, TMC8, TMEM154, UBFD1, VAT1, YLPM1, YWHAE, YWHAQ, ZAP70, ZNF837, AGT, AP2M1, APLP1, ARCN1, ASAP1, B3GNT1, BNIP3L, C12orf32, C19orf66, CCT8, CDC42EP3, CFDP1, CNBP, COG4, COPS6, CORO2A, CTPS1, CYCS, DALRD3, DDX10, DDX41, DHX35, FABP7, FASN, FLYWCH1, GNAI2, GNPDA1, H1F0, HNRNPAB, HSPA5, IL16, ITPR3, JUNB, LRRC8B, MARCH2, MBD1, MORF4L1, NAGLU, NCOA3, NEK1, NPLOC4, NSUN5P1, OLFML3, PAM, PHF23, PHIP, PIN1, PPM1G, R3HCC1, RABGGTB, RFC1, RIC8A, RPL18, RPS4Y2, RTKN, SAMHD1, SGK2, SND1, SPHK2, SPTBN4, STAG1, STAT3, TMUB2, TRAP1, TSR1, U2SURP, USP7, WBP11, WDR24, WDR33, WDR73, ZNF554, ZNFX1, A2M, AATK, ANAPC2, ANKRD11, ANKRD13B, ARHGAP30, ATP5O, ATRX, C11orf2, C11orf68, C19orf43, C7orf41, CCDC88A, CCT5, CD2BP2, CNPPD1, CPE, CSTB, CTAGE5, CTC1, DNTTIP2, FAM213A, FGFBP3, GEN1, GOLGA8A/GOLGA8B, GOLGB1, GRN, HDAC2, HLA-C, HNRNPM, HSP90AA1, INF2, KIAA1462, KRT19 (includes EG:16669), LDHB (includes EG:3945), LRIG1, MAGI1, MAN2C1, MARS, MED15, MGA, MICAL1, MINA, MRPS18C, PIGT, PIK3R5, POLR2J4, PPP1R15A, PRKAG1, PRSS53, PSMC5, RNF4, RPL13, RRP9, S100A9, SIPA1, SIPA1L3, SLC4A2, SOX4, SPTBN1, SRA1, SRM, SRSF2, STAT1, SYT1 (includes EG:20979), TKT, TREX1, TRIP12, TUBGCP3, TWF2, UBAP1, UBXN1, USP30, USP42, UXT, ZFPL1, ZMIZ2, ZNF335, ZNF358, ZNF629, AAMP, AHCY, ANXA11, ANXA6, ARL6IP4, ARPC4, ASMTL, ATP5H, BBS2, BEX4, C14orf129, C9orf16, CALR, CCT3, CDC123, DDR1, DDX19B, DNMBP, ELK1, EPHB3, F5, FAM208B, FKBP15, GANAB, GBE1, GPSM1, HIST1H1C, HNRNPC, HOOK2, IGF2, IGFBP6, INTS1, INTS9, LAMB1, LAMC2, LCP2, LRPAP1, MATK, MBD3 (includes EG:17192), MORC2, NAV2, NELF, NKRF, OGFR, PCDH7, PCGF2, PLXNB2, PODXL2, PRDX5, PSMB1, PSMB8, RAPGEF1, RPL37A, RPP40, SEL1L3, SFI1 (includes EG:305467), SH3BGRL3, SIVA1, SLC35A2, STAT6, STRN4, STX16, SUMF2, SYTL1, TBC1D10B, TMEM230, TSC22D3, VRK1, WAPAL, ZNF146, ZNRF1, AKT3, ASNSD1, ATP1A3, BRK1, BZW1, C17orf101, CDKN2D, CIAO1, EIF1, EZR, FAM13A, FAM40A, FAM65B, HAPLN3, HECTD1, KIF13B, LRRC37A3 (includes others), MAD1L1, MEPCE, NDUFS7, OS9, PARP1, PREP, RALBP1, RAP1GAP, SERINC2, SHKBP1, SSRP1, TGS1, TPM3, TRPS1, UCHL3, UQCRC2, WDR11, XAF1, AP3D1, C3orf19, CCDC86, DNAJA1, DYNC1H1, FAM120A, FAM32A, FNDC3A, FOXP4, HDAC10, HMGN2, HNRNPA2B1, HOXB3, HSF1 (includes EG:15499), IBA57 (includes EG:100330979), KHDRBS1, LARP4, MAP1A, MAST1, MCM6, MPST, NCOA4, NT5C3L, PTPN1, RASSF7, RPL10A, SAMD1, SDHB, SIPA1L1, SSSCA1, UBE2J2, ZMYM2, AKR1A1, AKR7A2, ANKRD24, ANXA1, BRF2, CBWD1, COX6B1, CSTF2T, EIF2A, EME2, GART, GPS1, INPP5E, ITGA6, KIF1C, LOC285463, MCM2, MLL3, N4BP3, NDST2, NHEJ1, NUDT5, PFAS, PJA2, RANBP2, SAP30BP, SEC13, SERBP1, SF3B3, SHCBP1, SMCHD1, SNX15, TACC2, TMEM8A, TMSB10/TMSB4X, TRAF2, TRAF4, UFD1L, VPS72 (includes EG:100001285), ZFP36L2, CORO1A, KLC4, KLHDC3, MTCH2, RNF13, SERPINF1, SGCE, ST3GAL3, STX18, TMEM59L, WHSC2, ZNF439, AKR1B1, APOBR, ARID1B, ATP5SL, BCL11A, C2orf29, CAPN2, CHMP1A, CLN6 (includes EG:315746), CLNS1A, CORO7/CORO7-PAM16, DHX16, DYNC1I2, ECSCR, EEF1A2, EIF3G, EPS8L3, FAM208A, FAM73A, GBP5, GLRX3, HNRNPA1, HNRPDL, IL17RA, L3MBTL2, LDB1, LOC494127, LOC644762, LPPR3, MAGED4/MAGED4B, MAP1B, MAPK6, MCRS1, MLL, NARS, NCL, PAIP1, PEPD, PES1, PLCB3, PLXNA2, POLR2J, PRDX1, PRPF3, PRPF8, PSD4, PSMF1, PTPN4, RARS2, RBM39, RFX5, RGS14, RNF166, RPL26, RPL28, SH2D2A, SPAG7, TAX1BP1, TCEA2, TUBA1B, TXNIP, UBE2D2, UBE2Q1, WDR6, WDR90, XBP1 (includes EG:140614), ACSS1, ANKRD44, ATXN3, COBRA1, DNAJA4, DNAJC11, GLE1 (includes EG:2733), GNL3, HDAC3, HDAC6, HDLBP, HINT1, HNRNPUL1, IGF2R, KCNJ14, LIN7C, NELL2, NMT1, PLCL2, PLD3, PNMA1, PPP1R13B, RSL1D1, SEC24B, SLC3A2, SMC1A, TAP1, TSEN54, UVSSA, WRB, ZC3H7B, ATXN7L2, BMS1, CCDC56, CHD3, DDOST, DENND5A, EIF2B4, EPN2, KAT6B, LTBP3, MAPK8IP1, MEAF6, MLL4, MPP3, NCKAP5L, NNAT, PIK3R2, PKD1, PKN1, PPBP, RPL15, SENP2, SGSM3, SKIV2L2, SMG6, SNRPD3, SYP, TADA3, ZBTB22, AKAP11, AKAP9, BINS, C12orf35, CNOT2, CREM (includes EG:12916), CRIP1, CSNK2B, DEF6, DENR, DIP2C, DNLZ, FAM59A, GJA9, HLA-B, IGHMBP2, KARS, KIAA0947, LOC100130899, LOC389705, LOC440354, MAN2B1, MAP7D1, MVD, OBSCN, OSTM1, PABPC1, PHF3, PIPSL, PRDM8, PRPF19, PRRT1, PSME1, PTGS2, RBM15, RERE, RPS10, SAP18, SCHIP1, SF3B2, SMEK2, SPECC1L, SPG7, SRSF4, SYNPO, TAF1C, THBS1, TRIM44, TRNAU1AP, UBAP2L, UIMC1, YARS, YTHDF1, ZFYVE28, ZNF668, AHSG, CASP1, CCT6A, CELF3, EIF4A2, FLII, FNTB, GPR56, INPP5D, LCAT, LRRC47, LRWD1, MYH9 (includes EG:17886), NBPF15 (includes others), NFIC, NOMO1 (includes others), PANK4, PFKM, PIGQ, PMPCB, PNN, RBL2 (includes EG:100331892), SGTA, SRSF1, STAU1, UBE2D4, UBE4A, ACTR1B, AEBP1, ARID5A, ATP6AP1, BTBD6, CDC37, CDC42BPB, CDCA4, CENPB, CEP192, COMMD7, CRAT, CSRP1, CTSK, DCAF6, DIRAS3, DMPK, EIF3D, ELAVL4, EPN1, ERBB2, ERCC3, FBLL1, FBXL17, FURIN, HIVEP2, INPPL1, IQGAP2, IWS1, LAT, LOXL2, MAGI2, METTL3, MKLN1, MRPS9 (includes EG:301371), MYCBP2, NARFL, NPEPL1, OFD1, P4HB, PHC2, PHF1, PRKAR2A, PSMD6, PSTPIP1, RASSF1, RPL18A, SEPN1, SIAH1, SIAM, TMEM184B, TTYH1, TUBB4B, UNK, USP39, VDAC1, ZNF592, ANKIB1, ANKRD54, BCR, BIRC5, CACNB3, CC2D1A (includes EG:212139), CHD8, CLIC1, COA5, EDF1, EPS8L2, FAM21B, GON4L, ILF3, IP6K1, LCMT1, MSLN, NEUROD2, NFATC4, PHAX, POLR2B, PTP4A3, PTPRA, QSOX1, RPL36A, SLC35B2, SMURF2, SRCAP, SYNE2, TMEM43, U2AF1, VBP1, WSB1, ANXA7, ARHGEF11, BCL9, C17orf28, C17orf56, CHCHD7, CHKB, CISH, CLK1, CYTIP, DDX24, DDX39B, DNM2, DOT1L, EFR3A, EXT2, FAM181A, GPR98, HIC1, HSPA1A/HSPA1B, KIF21B, KIF22, KLF6, LAT2, LMF2, MTA1, NIP7, NXPH3, PA2G4, PLXNB1, PPP1R8, PUF60, RAB43, RALGDS, RPAP2, SLC44A2, SSH3, SUPV3L1, TMEM173, TSC2, UBXN4, ZCCHC9, ZNF12, ZNF260, AKNA, ALB, ARAF, BAG1, BCL6, C9orf86, CCND1, CD97, CEP76, COL3A1, COMMD9, DLD, ENTPD6, KLF4, KLHL23/PHOSPHO2-KLHL23, LAMA5, LMO4, MAZ, MUC5AC/MUC5B, NOA1, NOL12, NRAS (includes EG:18176), POLR2A, PPP1RB, PRPF31, RNF135, RPS17/RPS17L, SART3, SCAF4, SECISBP2, SNX1, TARS2, TOMM34, TPI1P2, TTC27, ZNF428, ZNF574, APBA2, EEF1D, GABARAPL2, GTF3C1, HSPA9, KIF4A, MCM3AP, MOB4, MRPS24, NDUFAB1, OPA1, PEF1, PKP3, PPM1F, RUSC2, TMEM160, ABT1, ACTN4, BLMH, CEP70, CLASRP, CNKSR3, CRAMP1L, DUS3L, ETFA, FADD, FBRS, FKBP10, FKBP1A, HAX1, HINFP, HLA-A, HNRNPK, HNRNPR, INPP4A, ITK, LSM14A, LSP1 (includes EG:16985), MFHAS1, MLH3 (includes EG:217716), MSL1 (human), NAA25, NDUFA10, NDUFS2, NFRKB, NIPAL3, NUDC, NUMA1, OBFC1, OTUD1, PARP10, PEX1 (includes EG:100534854), PIGR, PPID, PRMT6, PRPS1, RAD21, RGS1, RPL17, RPS15, SEC24C, SF3A1, SIRT7, SKP1/SKP1P2, SLK, SPTAN1, STAB1, STAT4, TBC1D10A, TSPYL2, UBE2N, WASL, ZC3H3 (includes EG:223642), ZNF333, ZXDC, ACTB, AIM1 (includes EG:11630), CHMP1B, DVL2, EDC4, EXOSC5, FBN3, FBXO44, GSK3A, HNRNPH1, IL32, LONP1, MAPK7, MBD4, MSTO1, NARS2, NCAPG, NUF2, PPL, RPL9, SORD, TOE1, TRIM8, XPO1, ALG3, CARD11, CLC, DAXX, DDX27, DDX56, DSE, EIF4H, EXOC6, FEM1A, ISM1, MTM1, MUS81, MYO1F, NDFIP2, NET1 (includes EG:10276), NYNRIN, PDXDC1, PLEC, PRRC2C, RAB14, SCRIB, SCYL1, SETD4, SNX17, TBR1, TFF1, TXNRD1, AHCTF1, ARHGEF6, ATF1 (includes EG:100040260), ATG13 (includes EG:362164), CDC27, CIRH1A, CRYM, CSRNP1, DDX42, DIDO1, EIF3H, EIF4G1, EPRS, GLTSCR1, MARK3, MTHFS, NCOA6, NRBP1, NRXN2, PAAF1, PFKFB4, PPP1R2, REV3L, RIMBP3 (includes others), RPL7, S1PR4, SDF4, SIL1 (includes EG:100334837), TLE3 (includes EG:100007463), TMEM199, TPR, TRAK2, USP5, WASF1, ZBTB40, AACS, ACOT7, ARF3, BTBD10, BTBD2, DUSP8, FHL2, GSDMD, HADH, KEAP1, LAMP1, PMVK, PPP1R18, RC3H2, SFXN1, SMARCE1, SYT6, TAGLN3, USP15, ACAA1, ACSS2, ADAMTS16, AHNAK, AK2, ALKBH5, APBB1IP, APOL1, APOM, ARHGAP1, ATP13A2, ATP8B5P, BAD, BAP1, BAZ2A, BNC2, BRPF1, BTRC, BYSL, BZRAP1, C17orf70, C1orf144, C20orf3, C21orf2, C5orf55, C8orf33, CALB2, CBLC, CCDC137, CCDC77, CCNDBP1, CD40LG, CDK16, CENPT, CERK, CFP, CHD4, CHMP4B, COL1A2, COL6A1, COQ6, CPNE1, CRIPAK, CSK, CTTN, DAZAP2, DBNL, DCTN1, DDX20, DDX51, DEDD2, DNAJC13, DNMT1, DOCK2, DPYSL3, DRAP1, DUSP10, EGR2, EIF2S2, EIF3A, EIF5A, EIF5B, ENTPD4, ESYT1, FAM160B2, FAM60A, FIGNL1, FOXK1, FUT8, GIMAP5, GNB2, GOLGA4, GOLM1, GPATCH1, GYG1, GYS1, HADHA, HBP1, HNRNPH3, HNRNPL, HYOU1, IARS2, IKZF5, IL2RG, IRF4, ISG15, IST1 (includes EG:307833), JUP, KAT7, KCNN4, KIAA0319L, KIF2A, KPNA2, KSR1, LAG3, LANCL2, LARP1, LENG8, LGMN, LRSAM1, MALT1, MAPK8IP3, MAST4, MAT2A, ME3, MED13, MED8 (includes EG:112950), MICALL2, MIIP, MLH1, MLL2, MLST8, MRPL49 (includes EG:18120), NARF, NFX1, NHSL1, NOLC1, NOTCH1, NPIPL3 (includes others), NUP93, ODC1, PEX5, PEX6 (includes EG:117265), PHC1, PHF14, PHF20, PLEKHB2, PLEKHJ1, PLEKHM1P, PMF1, POLR1D, POM121, PPA1, PPP2R2B, PPRC1, PRKCSH, PSMD1, PTBP1, R3HDM2, RAD52 (includes EG:100426645), RANGAP1, RARA, RASSF5, RELB, RIPK1, RNF114, RPL22, RPLP0P2, RPS18, RPS6KA1, RPTOR, RSL24D1, SCAF11, SEC16A, SETD1B, SETX, SHE, SKIV2L, SLC1A5, SLC4A3, SLC7A5, SMARCB1, SNF8, SON, SPG20, SPINT1, SPNS2, SPRR3, SRSF7, SS18, SSBP4, STIM2, STK10, STOML2, SURF6, SUSD2, TACC3, TADA2B, TAF1 (includes EG:270627), TALDO1, TAOK2, TAP2, TBC1D1, TBCC, TCHP, TNFAIP8L2, TNKS, TNKS1BP1, TNRC6B, TOR1A, TRADD, TRAF3IP3, TRIAP1, TRIM66, TSHZ1, TUBGCP6, UBR4, UTY, VAV1, VCAN, VPS11, WBP2, WDR75, YTHDC1, ZC3H7A, ZC3HAV1, ZNF227, ZNF253, ZNF830, ZYX, CAP1, FAM189B, GSTM4, MRPL10 (includes EG:107732), NONO, OCIAD2, SRSF3, TANK, XPO4, ZNF638, ALKBH2, CCDC74A/CCDC74B, CLPTM1, EIF6, ERBB3, GREM1, GRWD1, ITGB2, JTB, MAGED2, MRPL23, NEFM, PSMC2, RAB3A, RPL10, RPL29 (includes EG:100039782), RUNDC3A, SEPT7, TCEAL2, TSPAN7, TXLNA, UBA1, USP10, ZNF192, ZNF284, CYFIP1, JPH3, PRPF4B, THAP7, ADAR, AFAP1, C19orf21, C22orf28, CDC5L, CEBPB (includes EG:1051), CNDP2, CPNE8, DIAPH1, DIEXF, DPP3, EXOSC7, FKBP9L, GLG1 (includes EG:20340), GLUL, GSTM2, HAUS4, HSP90AB1, KDM3B, KRBA1, LAS1L, LCK, MED13L, MPDU1, MTHFD2, MUC1, NUCB1, PCID2, PEBP1, PPP1R26, PRKCQ, PTOV1, RASGRP2, RGS2 (includes EG:19735), RPL36, RRP36 (includes EG:100360664), SEMA3F, SGCB, SIRT2, SMPD1, TCF7, TESC, TRIM24, USP11, YAF2, ZNF256.

Marker proteins identified by their Protein Symbol are sufficiently identified. Any protein identified by these Protein Symbols are subject of the present invention. Full names, sequences and additional information RefSeq Genes are freely available using publicly available databases, such as the NCBI database (www.ncbi.nlm.nih.gov) or in particular the UCSC genome browser (genome.ucsc.edu) as of 24 May 2013, when looking for the proteins. For the inventive proteins human RefSeq Genes exist, as noted in the database. For example, as stated by the UCSC genome browser, the protein C10orf35 is "uncharacterized protein; Position: chr10:71,390,003-71,393,355"; CNPPD1 is "*Homo sapiens* cyclin Pas1/PHO80 domain containing 1"; CRAT is "*Homo sapiens* carnitine L-acetyltransferase"; CLIP1 is "*Homo sapiens* CAP-GLY domain containing linker protein 1".

Although the detection of a single marker can be sufficient to indicate a risk for lung cancer, it is preferred to use more than one marker, e.g. 2, 3, 4, 5, 6, 7, 8, 9, 10, 11, 12 or more markers in combination, especially if combined with statistical analysis. From a diagnostic point of view, a single auto-antigen based diagnosis can be improved by increasing sensitivity and specificity by using a panel of markers where multiple autoantibodies are being detected simultaneously. Particular preferred combinations are of markers within one of the marker lists 2 to 31 as identified further herein.

The inventive markers are suitable protein antigens that are overexpressed in tumor and can be used to either identify cancerous tissue or to differentiate between histological lung cancer types. The markers usually cause an antibody reaction in a patient. Therefore the most convenient method to detect the presence of these markers in a patient is to detect antibodies against these marker proteins in a sample from the patient, especially a body fluid sample, such as blood, plasma or serum.

To detect an antibody in a sample it is possible to use marker proteins as binding agents and subsequently to detect bound antibodies. It is not necessary to use the entire marker proteins but it is sufficient to use antigenic fragments that are bound by the antibodies. "Antigenic fragment" herein relates to a fragment of the marker protein that causes an immune reaction against said marker protein in a human. Preferred antigenic fragments of any one of the inventive marker proteins are the fragments of the clones as identified by the UniqueID. Such antigenic fragments may be antigenic in a plurality of humans, such as at least 5, or at least 10 individuals.

"Diagnosis" for the purposes of this invention means the positive determination of lung cancer by means of the marker proteins according to the invention as well as the assignment of the patients to lung cancer. The term "diagnosis" covers medical diagnostics and examinations in this regard, in particular in-vitro diagnostics and laboratory diagnostics, likewise proteomics and peptide blotting. Further tests can be necessary to be sure and to exclude other diseases. The term "diagnosis" therefore likewise covers the differential diagnosis of lung cancer by means of the marker proteins according to the invention and the risk or prognosis of lung cancer.

Specific indications that can be identified with one or more of the inventive markers are lung cancer and in particular also histological types of lung cancer. Particular differentiations that can be made with the inventive markers and methods are distinguishing 1) healthy conditions vs. cancer (adenocarcinoma or large cell carcinoma or small cell carcinoma or squamous cell carcinoma), 2) healthy conditions vs. adenocarcinoma, 3) healthy conditions vs. large cell carcinoma, 4) healthy conditions vs. small cell carcinoma, and 5) healthy conditions vs. squamous cell carcinoma, 6) healthy conditions vs. large cell carcinoma plus adenocarcinoma, and 7) healthy conditions vs. small cell carcinoma plus squamous cell carcinoma.

The invention thus also relates to a surgical method comprising detecting cancer according to the present invention and removing said cancer.

In particular the inventive method may comprise detecting lung cancer and histological subtypes of lung cancer when distinguishing healthy conditions vs. cancer, healthy conditions vs. adenocarcinoma, healthy conditions vs. small cell carcinoma, healthy conditions vs. squamous cell carcinoma, and healthy conditions vs. large cell carcinoma. A positive result in distinguishing said indications can prompt a further cancer test, in particular more invasive tests than a blood test such as an endoscopy or biopsy.

The inventive markers are preferably grouped in sets of high distinctive value. Some sets excel at diagnosing or distinguishing 1, 2, 3, 4, 5, 6 or 7 of the above identified indications.

Preferred markers are of List 2, which comprise markers for all of the above indications 1) to 7).

List 2: Preferred Marker Protein Set, Suitable for Multiple Analytic Distinctions; Proteins are Identified by the Gene Symbol:
AKR1C4, ATRX, BCL11A, C10orf35, CD81, CDCA4, CEP250, CLIP1, CNPPD1, CRAT, CUL7, DDX10, EIF3M, FAM192A, FPGS, HIST1H1C, IMPDH2, KCTD15, LOC285463, MAP1B, MEGF6, NARFL, NECAP1, NFKB1, NFKBIA, NOL11, NUMA1, OGFR, PCBP1, PPP1CA, PPP4C, PRC1 (includes EG:233406), PSMC4, RABGGTB, RAI1, RCSD1, RFC1, RFX5, RPP40, SLC9A3R2, SNCB, SND1, SUMO1P3, TBX21, TMEM222, TP53 (includes EG:22059), TRAK1, TRIOBP, UTP14A, ZC3H13, ZNF837, ZNFX1.

In particular embodiments, the invention provides the method of diagnosing lung cancer or the risk of lung cancer in a patient by detecting at least 2 of the marker proteins selected from the markers of List 2 in a patient comprising the step of detecting antibodies binding said marker proteins, detecting said marker proteins or antigenic fragments thereof in a sample of the patient. Also provided is a method of diagnosing lung cancer or the risk of lung cancer in a patient by detecting at least 20%, preferably at least 30%, especially preferred at least 40%, at least 50%, at least 60%, at least 70%, at least 80% at least 90% or all of the marker proteins selected from the markers of List 2 in a patient comprising the step of detecting antibodies binding said marker proteins, detecting said marker proteins or antigenic fragments thereof in a sample of the patient.

Further preferred marker sets according to the present invention are provided in example 7 as lists 3 to 31. Thus the present invention also provides the method of diagnosing lung cancer or the risk of lung cancer in a patient by detecting at least 2 of the marker proteins selected from the markers of List 3, 4, 5, 6, 7, 8, 9, 10, 11, 12, 13, 14, 15, 16, 17, 18, 19, 20, 21, 22, 23, 24, 25, 26, 27, 28, 29, 30, 31 or any combination thereof in a patient comprising the step of detecting antibodies binding said marker proteins, detecting said marker proteins or antigenic fragments thereof in a sample of the patient. Further provided is a method of diagnosing lung cancer or the risk of lung cancer in a patient by detecting at least 20%, preferably at least 30%, especially preferred at least 40%, at least 50%, at least 60%, at least 70%, at least 80% at least 90% or all, of the marker proteins selected from the markers of List 3, 4, 5, 6, 7, 8, 9, 10, 11, 12, 13, 14, 15, 16, 17, 18, 19, 20, 21, 22, 23, 24, 25, 26, 27, 28, 29, 30, 31 or any combination thereof in a patient comprising the step of detecting antibodies binding said marker proteins, detecting said marker proteins or antigenic fragments thereof in a sample of the patient.

Also provided is a method of diagnosing lung cancer or the risk of lung cancer in a patient by detecting a marker protein selected from any one of List 1 in a patient comprising the step of detecting antibodies binding said marker protein, detecting said marker protein or antigenic fragments thereof in a sample of the patient. Of course, preferably more than one marker protein is detected. As noted with regards to the marker combinations of sets of lists 2 to 31, preferably at least 2, but also 3, 4, 5, 6, 7, 8, 9, 10, 11, 12, 13, 14, 15, 16, 17, 18, 19, 20, 21, 22, 23, 24, or 25 or more, of the inventive marker proteins can be detected. This relates to any one of the inventive sets of lists 1 to 31. Even more preferred at least 20%, at least 30%, at least 40%, at least 50%, at least 60%, at least 70%, at least 80%, at least 90%, at least 95% or all of the markers of any set of any of the lists 1 to 31 are used in a diagnostic set. Such parts of at least 2 markers or at least 20% markers (or more as indicated) are also referred to as subsets herein.

Such a marker combination of a particular list or any combination of marker selection thereof are referred to herein as diagnostic set. Such sets constitute a further aspect of the invention and kits are provided comprising diagnostic agents (such as binding moieties) to detect such markers. The entire disclosure herein relates to both the inventive kits (that can be used in the inventive methods) as well as the methods themselves, that make use of agents that can be comprised in the kit.

Preferred combinations are of markers that are particularly indicative for a specific distinction as given in table 1 below.

Preferred marker combinations are of 2, 3, 4, 5, 6 or 7 lists selected from lists 3, 4, 5, 6, 28, 29, and 30. These lists, as well as any combination are particularly effective for distinguishing indication 1, healthy conditions vs. cancer, and are preferably used therefore. Of course, not all of the markers are usually necessary since subsets also have sufficient diagnostic power. Preferably at least 2 markers or at least 20% of the markers (or any higher number as given above) of these lists or combined lists are used in the inventive methods.

Preferred marker combinations are of 2, 3, 4, or 5 lists selected from lists 7, 8, 9, 10, and 11. These lists, as well as any combination are particularly effective for distinguishing indication 2, healthy conditions vs. adenocarcinoma and are preferably used therefore. Of course, not all of the markers are usually necessary since subsets also have sufficient diagnostic power. Preferably at least 2 markers or at least 20% of the markers (or any higher number as given above) of these lists or combined lists are used in the inventive methods.

Preferred marker combinations are of 2, 3, 4, or 5 lists selected from lists 12, 13, 14, 15, and 16. These lists, as well as any combination are particularly effective for distinguishing indication 3, healthy conditions vs. large cell carcinoma, and are preferably used therefore. Of course, not all of the markers are usually necessary since subsets also have sufficient diagnostic power. Preferably at least 2 markers or at least 20% of the markers (or any higher number as given above) of these lists or combined lists are used in the inventive methods.

Preferred marker combinations are of 2, 3, 4, or 5 lists selected from lists 17, 18, 19, 20, and 21. These lists, as well as any combination are particularly effective for distinguishing indication 4, healthy conditions vs. small cell carcinoma, and are preferably used therefore. Of course, not all of the markers are usually necessary since subsets also have sufficient diagnostic power. Preferably at least 2 markers or at least 20% of the markers (or any higher number as given above) of these lists or combined lists are used in the inventive methods.

A preferred marker combination is of the 2, 3, 4, or 5 lists selected from lists 22, 23, 24, 25, and 26. These lists, as well as any combination are particularly effective for distinguishing indication 5, healthy conditions vs. squamous cell carcinoma, and are preferably used therefore. Of course, not all of the markers are usually necessary since subsets also have sufficient diagnostic power. Preferably at least 2 markers or at least 20% of the markers (or any higher number as given above) of these lists or combined lists are used in the inventive methods.

In especially preferred embodiments, the combination is of lists 3, 4, 5, 6, 28, 29, and 30, wherein the markers are selected from A2M, AATK, ACBD5, ACO2 (includes EG:11429), ADAMDEC1, ADH5 (includes EG:100145871), ADI1 (includes EG:104923), AGRN, AGT, AKAP13, AKAP8, AKR1C4, ALDOA, ALKBH2, ANAPC2, ANKRD11, ANKRD12, ANKRD13B, ANXA6, AP1G1, AP1M1, AP2M1, APBB1, APLP1, ARCN1, ARFRP1, ARHGAP30, ARHGDIA, ARHGEF1, ARHGEF18, ASAP1, ATG16L1, ATP5O, ATRX, ATXN2L, AZGP1, B3GNT1, BACE1, BAZ1A, BCAS2, BICD2, BNIP3L, BRD2, C10orf35, C11orf2, C11orf30, C11orf68, C12orf32, C19orf43, C19orf66, C1QTNF4, C7orf41, CAP1, CBX4, CCDC74A/CCDC74B, CCDC88A, CCDC88C, CCT5, CCT8, C2BP2, CD74, CD81, CDC42EP3, CDCA4, CEP250, CFDP1, CHST10, CLDN5, CLIP1, CLPTM1, CLTC, CLUAP1, CNBP, CNPPD1, COG4, COL4A1, COL6A3, COMP, COPA, COPE, COPS6, CORO2A, CORO7/CORO7-PAM16, CPE, CSTB, CTAGE5, CTBP2, CTC1, CTPS1, CUL7, CYCS, CYFIP1, D2HGDH, DAGLB, DALRD3, DDX10, DDX41, DDX54, DHX35, DLG5, DNAJB1, DNTTIP2, DUSP2, EDARADD, EDC4, EIF3M, EIF6, EML3, EPS8, ERBB3, ERCC5, EXOSC10, FABP7, FAM189B, FAM192A, FAM213A, FAM21A/FAM21C, FASN, FBF1, FBXW5, FGFBP3, FGFR3, FLOT1, FLYWCH1, FOSL2, FPGS, FYN, G3BP2, GABBR1, GEN1, GGA1 (includes EG:106039), GGA2, GLOD4, GNAI2, GNPDA1, GOLGA7, GOLGA8A/GOLGA8B, GOLGB1, GREM1, GRN, GRWD1, GSTM4, H1F0, HAUS7, HDAC2, HERC2, HLA-C, HLA-E, HMGB2, HNRNPAB, HNRNPM, HOXB2, HSP90AA1, HSPA5, HSPA8, HSPG2, ID3, IGHG1, IL16, IL1B, IMPDH2, INF2, ISOC1, ITFG3, ITGB2, ITPR3, JPH3, JTB, JUNB, KCTD15, KIAA1462, KIF5A, KRT19 (includes EG:16669), KRT73, LDHB (includes EG:3945), LOC341056, LRIG1, LRP1 (includes EG:16971), LRRC8B, LYSMD2, MAGED2, MAGI1, MAN2C1, MARCH2, MARS, MBD1, MBD4, MC1R, MDFIC, MED11 (includes EG:100148504), MED15, MED20, MED4 (includes EG:29079), MEGF6, METAP2, MGA, MICAL1, MINA, MORF4L1, MRPL10 (includes EG:107732), MRPL23, MRPS18C, MUC2 (includes EG:4583), NAGLU, NAP1L1, NARS2, NCOA3, NECAP1, NEDD9, NEFM, NEK1, NFATC1, NFKB1, NFKBIA, NFYA, NLRC5, NLRP1, NOL11, NONO, NOTCH2, NPHP3, NPLOC4, NR1H2, NSMCE1, NSUN5P1, NUMBL, OCIAD2, OLFML3, OTUD1, OTUD4, PAM, PARP14, PCBP1, PFKL, PHF23, PHIP, PIGT, PIK3R5, PIN1, PKM, PLCG1, POLR2B, POLR2J4, POTEE/POTEF, PPM1G, PPP1CA, PPP1R15A, PPP1R15B, PPP4C, PPP6R1, PRC1 (includes EG:233406), PRKAG1, PRMT1, PRPF4B, PRRC2A, PRSS53, PSAP, PSMA1, PSMB5, PSMC2, PSMC4, PSMC5, PSME4, QARS, R3HCC1, RAB3A, RABGGTB, RAI1, RAP2B, RASAL3, RCSD1, RECQL, RFC1, RIC8A, RNF39, RNF4, RPL10, RPL13, RPL18, RPL29 (includes EG:100039782), RPL9, RPS19, RPS25, RPS4Y2, RRP1B, RRP9, RSBN1, RTKN, RUNDC3A, S100A9, SAMHD1, SBK1, SCAF1, SCML4, SEPT7, SERPINF1, SETD2, SFN, SGK2, SIPA1, SIPA1L1, SIPA1L3, SIRT7, SLC4A2, SLC9A3R2, SMG5, SMYD5, SNCB, SND1, SNRNP48, SNRPF, SORD, SOX4, SPHK2, SPTBN1, SPTBN4, SRA1, SREBF2, SRM, SRPR, SRRM2, SRSF2, SRSF3, STAG1, STAG2, STAT1, STAT3, SUMO1P3, SYT1 (includes EG:20979), TANK, TAPBPL, TBCB, TBX21, TCEAL2, TFRC, TGOLN2, THAP7, TIAM1, TKT, TMC8, TMEM154, TMEM160, TMEM222, TMUB2, TOMM20 (includes EG:100043869), TP53 (includes EG:22059), TP53BP2, TRAK1, TRAP1, TREX1, TRIM28, TRIM78P, TRIOBP, TRIP12, TSPAN7, TSR1, TUBGCP3, TWF2, TXLNA, TXN2, U2AF1, U2SURP, UBA1, UBAP1, UBFD1, UBXN1, UQCRC1, USP10, USP30, USP42, USP7, UTP14A, UXT, VAT1, VIMP, WBP11, WDR24, WDR33, WDR73, WHSC2, WNK2, XPO1, XPO4, YLPM1, YWHAE, YWHAQ, ZAP70, ZC3H13, ZEB1, ZFPL1, ZMIZ2, ZNF192, ZNF284, ZNF335, ZNF358, ZNF554, ZNF629, ZNF638, ZNF837, ZNFX1. These markers as well as the combined set of any one of at least 2 markers or at least 20% of said markers (or any higher number as indicated above) is particularly suitable for distinguishing healthy conditions vs. cancer and is preferably used for this diagnosis.

In especially preferred embodiments, the combination is of lists 7, 8, 9, 10, and 11 and wherein the markers are selected from AAMP, AATK, AGRN, AHCY, AKR1A1, AKR7A2, AKT3, ANKRD24, ANXA1, ANXA11, ANXA6, AP1M1, AP2M1, AP3D1, ARCN1, ARL6IP4, ARPC4, ASAP1, ASMTL, ASNSD1, ATP1A3, ATP5H, ATRX, BBS2, BEX4, BRF2, BRK1, BZW1, C10orf35, C14orf129, C17orf101, C19orf66, C1QTNF4, C3orf19, C9orf16, CALR, CBWD1, CCDC86, CCT3, CDC123, CDKN2D, CEP250, CIAO1, CNBP, CORO1A, COX6B1, CSTB, CSTF2T, CUL7, DALRD3, DDR1, DDX19B, DNAJA1, DNMBP, DNTTIP2, DYNC1H1, EIF1, EIF2A, ELK1, EME2, EPHB3, EZR, F5, FAM120A, FAM13A, FAM192A, FAM208B, FAM32A, FAM40A, FAM65B, FKBP15, FLYWCH1, FNDC3A, FOXP4, GANAB, GART, GBE1, GGA1 (includes EG:106039), GPS1, GPSM1, HAPLN3, HDAC10, HECTD1, HIST1H1C, HMGN2, HNRNPA2B1, HNRNPC, HOOK2, HOXB3, HSF1 (includes EG:15499), IBA57 (includes EG:100330979), IGF2, IGFBP6, INPP5E, INTS1, INTS9, ITGA6, KCTD15, KHDRBS1, KIF13B, KIF1C, KLC4, KLHDC3, LAMB1, LAMC2, LARP4, LCP2, LOC285463, LRP1 (includes EG:16971), LRPAP1, LRRC37A3 (includes others), MAD1L1, MAP1A, MARS, MAST1, MATK, MBD3 (includes EG:17192), MC1R, MCM2, MCM6, MED15, MEGF6, MEPCE, MLL3, MORC2, MPST, MTCH2, MUC2 (includes EG:4583), N4BP3, NAGLU, NAV2, NCOA4, NDST2, NDUFS7, NELF, NFKB1, NHEJ1, NKRF, NOL11, NR1H2, NT5C3L, NUDT5, OGFR, OS9, PARP1, PCDH7, PCGF2, PFAS, PJA2, PLCG1, PLXNB2, PODXL2, PPP1CA, PPP1R15A, PPP4C, PPP6R1, PRDX5, PREP, PRKAG1, PSMB1, PSMB8, PSMC4, PTPN1, RALBP1, RANBP2, RAP1GAP, RAPGEF1, RASSF7, RCSD1, RFC1, RIC8A, RNF13, RPL10A, RPL18, RPL37A, RPP40, RPS25, SAMD1, SAP30BP, SDHB, SEC13, SEL1L3, SERBP1, SERINC2, SERPINF1, SETD2, SF3B3, SFI1 (includes EG:305467), SGCE, SH3BGRL3, SHCBP1, SHKBP1, SIPA1L1, SIVA1, SLC35A2, SMCHD1, SMG5, SNCB, SNRNP48, SNX15, SOX4, SPTBN1, SRA1, SSRP1, SSSCA1, ST3GAL3, STAT6, STRN4, STX16, STX18, SUMF2, SUMO1P3, SYTL1, TACC2, TBC1D10B, TGS1, TMEM222, TMEM230, TMEM59L, TMEM8A, TMSB10/TMSB4X, TP53 (includes EG:22059), TPM3, TRAF2, TRAF4, TRAK1, TRIM28, TRIOBP, TRPS1, TSC22D3, TWF2, U2SURP, UBE2J2, UCHL3, UFD1L, UQCRC2, USP30, VIMP, VPS72 (includes EG:100001285), VRK1, WAPAL, WDR11, WHSC2, XAF1, ZFP36L2, ZFPL1, ZMYM2, ZNF146, ZNF439, ZNRF1. These markers as well as the combined set of any one of at least 2 markers or at least 20% of said markers (or any higher number as indicated above) is particularly suitable for distinguishing healthy conditions vs. adenocarcinoma and is preferably used for this diagnosis.

In especially preferred embodiments, the combination is of lists 12, 13, 14, 15, and 16 and wherein the markers are selected from ACSS1, AHSG, AKAP11, AKAP9, AKR1B1, ANAPC2, ANKRD11, ANKRD44, ANXA6, APOBR, ARHGAP30, ARHGEF1, ARID1B, ATP5SL, ATXN3, ATXN7L2, BCL11A, BIN3, BMS1, BRD2, C11orf68, C12orf32, C12orf35, C17orf101, C19orf43, C2orf29, CAPN2, CASP1, CCDC56, CCT3, CCT6A, CD81, CDC123, CELF3, CFDP1, CHD3, CHMP1A, CLDN5, CLIP1, CLN6 (includes EG:315746), CLNS1A, CNOT2, COBRA1, COL4A1, CORO7/CORO7-PAM16, CREM (includes EG:12916), CRIP1, CSNK2B, CTPS1, CUL7, DDOST, DDR1, DDX10, DDX54, DEF6, DENND5A, DENR, DHX16, DIP2C, DNAJA4, DNAJC11, DNLZ, DYNC1I2, ECSCR, EEF1A2, EIF2A, EIF2B4, EIF3G, EIF4A2, EPN2, EPS8L3, ERCC5, EZR, FAM208A, FAM32A, FAM59A, FAM65B, FAM73A, FASN, FBXW5, FGFR3, FLII, FNTB, GBP5, GJA9, GLE1 (includes EG:2733), GLRX3, GNAI2, GNL3, GPR56, GRN, HDAC3, HDAC6, HDLBP, HERC2, HINT1, HLA-B, HNRNPA1, HNRNPUL1, HNRPDL, IGF2R, IGHG1, IGHMBP2, IL17RA, INPP5D, ITFG3, KARS, KAT6B, KCNJ14, KIAA0947, KRT73, L3MBTL2, LCAT, LDB1, LIN7C, LOC100130899, LOC285463, LOC389705, LOC440354, LOC494127, LOC644762, LPPR3, LRRC47, LRWD1, LTBP3, MAGED4/MAGED4B, MAGI1, MAN2B1, MAP1B, MAP7D1, MAPK6, MAPK8IP1, MBD3 (includes EG:17192), MCRS1, MEAF6, MLL, MLL4, MPP3, MVD, MYH9 (includes EG:17886), NARS, NBPF15 (includes others), NCKAP5L, NCL, NCOA3, NELL2, NFATC1, NFIC, NFKB1, NMT1, NNAT, NOL11, NOMO1 (includes others), NOTCH2, NPHP3, OBSCN, OGFR, OS9, OSTM1, PABPC1, PAIP1, PANK4, PARP1, PCBP1, PEPD, PES1, PFKM, PHF3, PIGQ, PIK3R2, PIPSL, PKD1, PKN1, PLCB3, PLCL2, PLD3, PLXNA2, PMPCB, PNMA1, PNN, POLR2J, PPBP, PPP1R13B, PPP1R15A, PPP6R1, PRC1 (includes EG:233406), PRDM8, PRDX1, PRPF19, PRPF3, PRPF8, PRRT1, PSD4, PSMB8, PSME1, PSMF1, PTGS2, PTPN4, RABGGTB, RAI1, RARS2, RBL2 (includes EG:100331892), RBM15, RBM39, RERE, RFX5, RGS14, RNF166, RNF39, RPL15, RPL18, RPL26, RPL28, RPP40, RPS10, RPS19, RSL1D1, SAP18, SCHIP1, SDHB, SEC24B, SENP2, SETD2, SF3B2, SGSM3, SGTA, SH2D2A, SKIV2L2, SLC3A2, SLC9A3R2, SMC1A, SMEK2, SMG6, SNCB, SND1, SNRPD3, SPAG7, SPECC1L, SPG7, SRA1, SRSF1, SRSF4, STAU1, SYNPO, SYP, TADA3, TAF1C, TAP1, TAX1BP1, TBX21, TCEA2, THBS1, TPM3, TRIM44, TRIOBP, TRNAU1AP, TSEN54, TUBA1B, TXN2, TXNIP, U2SURP, UBAP2L, UBE2D2, UBE2D4, UBE2Q1, UBE4A, UFD1L, UIMC1, USP7, UTP14A, UVSSA, WDR6, WDR90, WRB, XBP1 (includes EG:140614), YARS, YTHDF1, ZBTB22, ZC3H13, ZC3H7B, ZEB1, ZFYVE28, ZNF668, ZNF837, ZNFX1. These markers as well as the combined set of any one of at least 2 markers or at least 20% of said markers (or any higher number as indicated above) is particularly suitable for distinguishing healthy conditions vs. large cell carcinoma and is preferably used for this diagnosis.

In especially preferred embodiments, the combination is of lists 17, 18, 19, 20, and 21 and wherein the markers are selected from ACBD5, ACTR1B, ADH5 (includes EG:100145871), AEBP1, AKNA, AKR1C4, ALB, ANKIB1, ANKRD54, ANXA6, ANXA7, AP2M1, AP3D1, APBA2, ARAF, ARHGEF11, ARID5A, ATP5H, ATP6AP1, ATRX, BAG1, BCL6, BCL9, BCR, BEX4, BIN3, BIRC5, BTBD6, C17orf28, C17orf56, C9orf86, CACNB3, CBWD1, CC2D1A (includes EG:212139), CCND1, CCT6A, CD74, CD97, CDC37, CDC42BPB, CDCA4, CENPB, CEP192, CEP76, CHCHD7, CHD8, CHKB, CISH, CLIC1, CLK1, CNPPD1, COA5, COG4, COL3A1, COMMD7, COMMD9, CORO2A, CPE, CRAT, CSRP1, CTPS1, CTSK, CYTIP, DCAF6, DDX24, DDX39B, DHX16, DIRAS3, DLD, DMPK, DNM2, DOT1L, ECSCR, EDARADD, EDF1, EEF1D, EFR3A, EIF1, EIF3D, EIF3M, ELAVL4, ENTPD6, EPN1, EPS8, EPS8L2, ERBB2, ERCC3, EXOSC10, EXT2, FAM181A, FAM21B, FBLL1, FBXL17, FBXW5, FGFBP3, FURIN, GABARAPL2, GART, GJA9, GON4L, GPR98, GRN, GTF3C1, HAPLN3, HIC1, HIVEP2, HNRNPUL1, HSPA1A/HSPA1B, HSPA5, HSPA9, HSPG2, ILF3, IMPDH2, INPP5E, INPPL1, IP6K1, IQGAP2, ITFG3, IWS1, KCTD15, KIF21B, KIF22, KIF4A, KLF4, KLF6, KLHL23/PHOSPHO2-KLHL23, LAMA5, LAT, LAT2, LCMT1, LMF2, LMO4, LOC285463, LOC341056, LOXL2, MAGED4/MAGED4B, MAGI2, MARCH2, MARS, MAZ, MCM3AP, MED11 (includes EG:100148504), METTL3, MKLN1, MOB4, MPST, MRPS24, MRPS9 (includes EG:301371), MSLN, MTA1, MUC5AC/MUC5B, MYCBP2, NAP1L1, NARFL, NBPF15 (includes others), NDUFAB1, NECAP1, NEK1, NEUROD2, NFATC4, NFKB1, NFKBIA, NIP7, NOA1, NOL11, NOL12, NPEPL1, NRAS (includes EG:18176), NXPH3, OFD1, OPA1, P4HB, PA2G4, PARP1, PCBP1, PEF1, PHAX, PHC2, PHF1, PHF3, PIN1, PKP3, PLXNB1, POLR2A, POLR2B, POLR2J4, PPM1F, PPP1R1B, PPP1R8, PRDX1, PRKAR2A, PRPF31, PSMB5, PSMD6, PSMF1, PSTPIP1, PTP4A3, PTPRA, PUF60, QSOX2, RAB43, RABGGTB, RALGDS, RASSF1, RCSD1, RFC1, RFX5, RNF135, RPAP2, RPL18A, RPL26, RPL36A, RPS17/RPS17L, RUSC2, SAP30BP, SART3, SCAF4, SEC13, SECISBP2, SEPN1, SF3B2, SGSM3, SIAH1, SLC35A2, SLC35B2, SLC44A2, SMURF2, SNCB, SNX1, SRCAP, SREBF2, SRSF2, SSH3, SIAM, SUMO1P3, SUPV3L1, SYNE2, SYNPO, TARS2, TGOLN2, TGS1, TMEM160, TMEM173, TMEM184B, TMEM43, TMSB10/TMSB4X, TOMM34, TP53 (includes EG:22059), TPI1P2, TRIM28, TRIOBP, TSC2, TTC27, TTYH1, TUBB4B, U2AF1, U2SURP, UBE2J2, UBXN4, UNK, UQCRC1, USP39, VBP1, VDAC1, WBP11, WSB1, ZC3H13, ZCCHC9, ZNF12, ZNF260, ZNF428, ZNF439, ZNF574, ZNF592. These markers as well as the combined set of any one of at least 2 markers or at least 20% of said markers (or any higher number as indicated above) is particularly suitable for distinguishing healthy conditions vs. small cell carcinoma and are preferably used for this diagnosis.

In especially preferred embodiments, the combination is of lists 22, 23, 24, 25, and 26 and wherein the markers are selected from AACS, AAMP, ABT1, ACO2 (includes EG:11429), ACOT7, ACTB, ACTN4, ACTR1B, ADI1 (includes EG:104923), AGT, AHCTF1, AIM1 (includes EG:11630), AKR1C4, ALG3, ANKRD24, AP2M1, AP3D1, APBB1, APLP1, ARF3, ARHGDIA, ARHGEF6, ARID5A, ATF1 (includes EG:100040260), ATG13 (includes EG:362164), ATP1A3, ATRX, BCL11A, BEX4, BLMH, BTBD10, BTBD2, C10orf35, CARD11, CC2D1A (includes EG:212139), CD81, CDC27, CELF3, CEP70, CHD3, CHMP1A, CHMP1B, CIRH1A, CLASRP, CLC, CLIP1, CNKSR3, COPA, CRAMP1L, CRAT, CRYM, CSRNP1, CSTB, DAXX, DDR1, DDX27, DDX42, DDX56, DIDO1, DIRAS3, DNAJB1, DNAJC11, DSE, DUS3L, DUSP8, DVL2, DYNC1I2, EDC4, EIF3H, EIF4G1, EIF4H, ENTPD6, EPRS, EPS8, ETFA, EXOC6, EXOSC5, FADD, FAM192A, FAM21A/FAM21C, FAM40A, FAM59A, FASN, FBN3, FBRS, FBXO44, FEM1A, FHL2, FKBP10, FKBP1A, FYN, GEN1, GLOD4, GLRX3, GLTSCR1, GRN, GSDMD, GSK3A, HADH, HAX1, HINFP, HLA-A, HLA-B, HMGB2, HNRNPA2B1, HNRNPAB, HNRNPH1, HNRNPK, HNRNPR, IL32, INPP4A, INTS1, ISM1, ISOC1, ITFG3, ITK, KCTD15, KEAP1, KHDRBS1, KLF4, LAMA5, LAMB1, LAMP1, LOC285463, LONP1, LSM14A, LSP1 (includes EG:16985), MAP7D1, MAPK7, MAPK8IP1, MARK3, MAZ, MBD4, MFHAS1, MLH3 (includes EG:217716), MLL3, MSL1 (human), MSTO1, MTHFS, MTM1, MUS81, MYO1F, NAA25, NARFL, NARS2, NCAPG, NCOA4, NCOA6, NDFIP2, NDUFA10, NDUFS2, NECAP1, NET1 (includes EG:10276), NFKBIA, NFRKB, NIPAL3, NOL11, NOL12, NR1H2, NRBP1, NRXN2, NUDC, NUF2, NUMA1, NYNRIN, OBFC1, OGFR, OTUD1, PAAF1, PARP10, PDXDC1, PEPD, PEX1 (includes EG:100534854), PFKFB4, PFKM, PHC2, PIGQ, PIGR, PIPSL, PLEC, PMVK, PPID, PPL, PPP1CA, PPP1R18, PPP1R2, PPP4C, PRMT6, PRPF8, PRPS1, PRRC2C, PSMA1, PSMC4, PUF60, QARS, RAB14, RAD21, RAI1, RALBP1, RASSF1, RBM39, RC3H2, RCSD1, REV3L, RGS1, RIMBP3 (includes others), RPL17, RPL7, RPL9, RPP40, RPS15, RPS17/RPS17L, RPS4Y2, S1PR4, SCML4, SCRIB, SCYL1, SDF4, SEC24C, SETD4, SF3A1, SFN, SFXN1, SH2D2A, SIL1 (includes EG:100334837), SIRT7, SKP1/SKP1P2, SLC3A2, SLC44A2, SLK, SMARCE1, SMC1A, SMG5, SNX17, SORD, SPTAN1, SRA1, SRRM2, STAB1, STAT4, SYNPO, SYT6, TAGLN3, TBC1D10A, TBCB, TBR1, TBX21, TFF1, TLE3 (includes EG:100007463), TMEM184B, TMEM199, TMEM222, TMUB2, TOE1, TP53 (includes EG:22059), TP53BP2, TPR, TRAK2, TRAP1, TRIM8, TSC2, TSPYL2, TUBA1B, TXNRD1, U2SURP, UBE2N, UFD1L, USP15, USP5, VAT1, VPS72 (includes EG:100001285), WASF1, WASL, XPO1, ZBTB40, ZC3H3 (includes EG:223642), ZEB1, ZNF333, ZNFX1, ZXDC. These markers as well as the combined set of any one of at least 2 markers or at least 20% of said markers (or any higher number as indicated above) is particularly suitable for distinguishing healthy conditions vs. squamous cell carcinoma and are preferably used for this diagnosis.

Some markers are more preferred than others. Especially preferred markers are those which are represented at least 5, at least 6, at least 7, at least 8, at least 9, at least 10, at least 11, at least 12 times in any one of lists 3 to 31. These markers are preferably used in any one of the inventive methods or sets.

Less preferred markers are selected from ABCC3, ADAM29, ANXA1, ANXA2, BIRC5, CA125, CA19-9, CAGE, CCNB1, CEA, CTAG1B, CTSD, Cyfra 21-1, EEF1A, eIF4G, ENO1, erp29, FH, GAGE 7, GBU4-5, HER2, HLA-B, HMMR, HSD17B3, HSP70-9B, IGF2BP2, IMMP1L, IMPDH, LAMC1, LBC, L-myc, MAGEC1, MALAT1, MTAP, MUC1, MYCBP, NOLC1, NSE, NY-ESO-1, OMLF1, OXCT1, p16, p62, PGAM, PKC, PMS2L15, PRDX6, ProGRP, PTH, PXN, RBP, RCVRN, RP11-499F19, RPL23A, SEC15L2, SERPINA1, SERPINB3, SMOX, SOX1, SOX2, SOX21, SOX3, TLP, TP53, TPA, TPI1, UBQLN1, XAGE-1, XRCC5, ZIC2.

Preferably none of these markers is used in the inventive methods or present in one of the inventive set.

The present invention also relates to a method of selecting such at least 2 markers (or more as given above) or at least 20% of the markers (or more as given above) of any one of the inventive sets with high specificity. Such a method includes comparisons of signal data for the inventive markers of any one of the inventive markers sets, especially as listed in lists 1 to 31, with said signal data being obtained from controls samples of known conditions or indications and further statistically comparing said signal data with said conditions thereby obtaining a significant pattern of signal data capable of distinguishing the conditions of the known control samples.

In particular, the controls may comprise one or more cancerous control (preferably at least 5, or at least 10 cancerous controls) and a healthy control (preferably at least 5, or at least 10 healthy controls). Preferably 2 different indications are selected that shall be distinguished. In preferred embodiments, the control comprises samples for the indications selected from indications 1), 2), 3), 4), 5), 6), and 7) as mentioned above.

The controls can be used to obtain a marker dependent signal pattern as indication classifier. Such a signal pattern can be obtained by routine statistical methods, such as binary tree methods. Common statistical methods calculate a (optionally multi-dimensional) vector within the multitude of control data signal values as diagnostically significant distinguishing parameter that can be used to distinguish one or more indications from other one or more indications. The step usually comprises the step of "training" a computer software with said control data. Such pre-obtained training data or signal data can be provided on a computer-readable medium to a practitioner who performs the inventive diagnosis.

Preferably, the method comprises optimizing the selection process, e.g. by selecting alternative or additional markers and repeating said comparison with the controls signals, until a specificity and/or sensitivity of at least 75% is obtained, preferably of at least 80%, at least 85%, at least 90%, at least 95%.

"Marker" or "marker proteins" are diagnostic indicators found in a patient and are detected, directly or indirectly by the inventive methods. Indirect detection is preferred. In particular, all of the inventive markers have been shown to cause the production of (auto)antigens in cancer patients or patients with a risk of developing cancer. The easiest way to detect these markers is thus to detect these (auto)antibodies in a blood or serum sample from the patient. Such antibodies can be detected by binding to their respective antigen in an assay. Such antigens are in particular the marker proteins themselves or antigenic fragments thereof. Suitable methods exist in the art to specifically detect such antibody-antigen reactions and can be used according to the invention. Preferably the entire antibody content of the sample is normalized (e.g. diluted to a preset concentration) and applied to the antigens. Preferably the IgG, IgM, IgD, IgA or IgE antibody fraction, is exclusively used. Preferred antibodies are IgG. Preferably the subject is a human and consequently also the marker proteins as auto-antigens are human.

Binding events can be detected as known in the art, e.g. by using labeled secondary antibodies. Such labels can be enzymatic, fluorescent, radioactive or a nucleic acid sequence tag. Such labels can also be provided on the binding means, e.g. the antigens as described in the previous paragraph. Nucleic acid sequence tags are especially preferred labels since they can be used as sequence code that not only leads to quantitative information but also to a qualitative identification of the detection means (e.g. antibody with certain specificity). Nucleic acid sequence tags can be used in known methods such as Immuno-PCR. In multiplex assays, usually qualitative information is tied to a specific location, e.g. spot on a microarray. With qualitative information provided in the label, it is not necessary to use such localized immunoassays. In is possible to perform the binding reaction of the analyte and the detection means, e.g. the serum antibody and the labeled antigen, independent of any solid supports in solution and obtain the sequence information of the detection means bound to its analyte. A binding reaction allows amplification of the nucleic acid label in a detection reaction, followed by determination of the nucleic acid sequence determination. With said determined sequence the type of detection means can be determined and hence the marker (analyte, e.g. serum antibody with tumor associated antigen specificity).

In preferred embodiments of the invention the step of detecting antibodies binding said marker proteins, detecting said marker proteins or antigenic fragments thereof comprises comparing said detection signal with detection signals of a healthy control and comparing said detection signals, wherein an increase in the detection signal indicates lung cancer or said risk of lung cancer.

In preferred embodiments of the invention the step of detecting antibodies binding said marker proteins, detecting said marker proteins or antigenic fragments thereof comprises comparing said detection signal with detection signals of a cancerous control. In preferred embodiments, the control comprises the indications that are intended to be distinguished, such as indications 1), 2), 3), 4), 5), 6), and 7) as mentioned above. In particular preferred, especially in cases of using more marker sets of 2 or more markers as mentioned above, a statistical analysis of the control is performed, wherein the controls are used to obtain a marker dependent signal pattern as indication classifier and the marker dependent signals of the sample to be analysed is compared with and/or fitted onto said pattern thereby obtaining information of the diagnosed condition or indication. Such a signal pattern can be obtained by routine statistical methods, such as binary tree methods. Common statistical methods calculate a (optionally multi-dimensional) vector within the multitude of control data signal values as diagnostically significant distinguishing parameter that can be used to distinguish one or more indications from other one or more indications. Such statistical analysis is usually dependent on the used analytical platform that was used to obtain the signal data, given that signal data may vary from platform to platform. Such platforms are e.g. different microarray or solution based setups (with different labels or analytes—such as antigen fragments—for a particular marker). Thus the statistical method can be used to calibrate each platform to obtain diagnostic information with high sensitivity and specificity. The step usually comprises the step of "training" a computer software with said control data. Alternatively, pre-obtained training data can be used. Such pre-obtained training data or signal data can be provided on a computer-readable medium to a practitioner.

In further embodiments a detection signal from the sample of a patient in amplitude of at least 60%, preferably at least 80%, of the cancerous control indicates lung cancer.

Usually not all of the inventive markers or detection agents may lead to a signal. Nevertheless only a fraction of the signals is suitable to arrive at a diagnostic decision. In preferred embodiments of the invention a detection signal in at least 60%, preferably at least 70%, least 75%, at least 85%, or in particular preferred at least 95%, even more preferred all, of the used markers indicates.

The present diagnostic methods further provide necessary therapeutic information to decide on a surgical intervention. Therefore the present invention also provides a method of treating a patient comprising lung cancer, comprising detecting cancer according to any aspect or embodiment of the invention and removing said lung cancer. "Stratification or therapy control" for the purposes of this invention means that the method according to the invention renders possible decisions for the treatment and therapy of the patient, whether it is the hospitalization of the patient, the use, effect and/or dosage of one or more drugs, a therapeutic measure or the monitoring of a course of the disease and the course of therapy or etiology or classification of a disease, e.g., into a new or existing subtype or the differentiation of diseases and the patients thereof. In a further embodiment of the invention, the term "stratification" covers in particular the risk stratification with the prognosis of an outcome of a negative health event.

One skilled in the art is familiar with expression libraries, they can be produced according to standard works, such as Sambrook et al, "Molecular Cloning, A laboratory handbook, 2nd edition (1989), CSH press, Cold Spring Harbor, N.Y. Expression libraries are also preferred which are tissue-specific (e.g., human tissue, in particular human organs). Members of such libraries can be used as inventive antigen for use as detection agent to bind analyte antibodies. Furthermore included according to the invention are expression libraries that can be obtained by exon-trapping. A synonym for expression library is expression bank. Also preferred are protein biochips or corresponding expression libraries that do not exhibit any redundancy (so-called: Uniclone® library) and that may be produced, for example, according to the teachings of WO 99/57311 and WO 99/57312. These preferred Uniclone libraries have a high portion of non-defective fully expressed proteins of a cDNA expression library. Within the context of this invention, the antigens can be obtained from organisms that can also be, but need not be limited to, transformed bacteria, recombinant phages, or transformed cells from mammals, insects, fungi, yeasts, or plants. The marker antigens can be fixed, spotted, or immobilized on a solid support. Alternatively, is also possible to perform an assay in solution, such as an Immuno-PCR assay.

In a further aspect, the present invention provides a kit of diagnostic agents suitable to detect any marker or marker combination as described above, preferably wherein said diagnostic agents comprise marker proteins or antigenic fragments thereof suitable to bind antibodies in a sample, especially preferred wherein said diagnostic agents are immobilized on a solid support or in solution, especially when said markers are each labelled with a unique label, such as a unique nucleic acid sequence tag. The inventive kit may further comprise detection agents, such as secondary antibodies, in particular anti-human antibodies, and optionally also buffers and dilution reagents. The invention therefore likewise relates to the object of providing a diagnostic device or an assay, in particular a protein biochip, ELISA or Immuno-PCR assay, which permits a diagnosis or examination for lung carcinoma.

Additionally, the marker proteins (as binding moieties for antibody detection) can be present in the respective form of a fusion protein, which contains, for example, at least one affinity epitope or tag. The tag may be one such as contains c-myc, his tag, arg tag, FLAG, alkaline phosphatase, VS tag, T7 tag or strep tag, HAT tag, NusA, S tag, SBP tag, thioredoxin, DsbA, a fusion protein, preferably a cellulose-binding domain, green fluorescent protein, maltose-binding protein, calmodulin-binding protein, glutathione S-transferase, or lacZ, a nanoparticle or a nucleic acid sequence tag. Such a nucleic acid sequence can be e.g. DNA or RNA, preferably DNA.

In all of the embodiments, the term "solid support" covers embodiments such as a filter, a membrane, a magnetic or fluorophore-labeled bead, a silica wafer, glass, metal, ceramics, plastics, a chip, a target for mass spectrometry, or a matrix. However, a filter is preferred according to the invention.

As a filter, furthermore PVDF, nitrocellulose, or nylon is preferred (e.g., Immobilon P Millipore, Protran Whatman, Hybond N+ Amersham).

In another preferred embodiment of the arrangement according to the invention, the arrangement corresponds to a grid with the dimensions of a microtiter plate (8-12 wells strips, 96 wells, 384 wells, or more), a silica wafer, a chip, a target for mass spectrometry, or a matrix.

Preferably the inventive kit also comprises non-diagnostic control proteins, which can be used for signal normalization. These control proteins bind to moieties, e.g. proteins or antibodies, in the sample of a diseased patient same as in a healthy control. In addition to the inventive marker proteins any number, but preferably at least 2 controls can be used in the method or in the kit.

Preferably the inventive kit is limited to a particular size. According to these embodiments of the invention the kit comprises at most 3000 diagnostic agents, preferably at most 2500 diagnostic agents, at most 2000 diagnostic agents, at most 1500 diagnostic agents, at most 1200 diagnostic agents, at most 1000 diagnostic agents, at most 800 diagnostic agents, at most 500 diagnostic agents, at most 300 diagnostic agents, at most 200 diagnostic agents, at most 100 diagnostic agents, such as marker proteins or antigenic fragments thereof.

In especially preferred embodiments of the invention the kit further comprises a computer-readable medium or a computer program product, such as a computer readable memory devices like a flash storage, CD-, DVD- or BR-disc or a hard drive, comprising signal data for the control samples with known conditions selected from cancer and/or of healthy controls, and/or calibration or training data for analysing said markers provided in the kit for diagnosing lung cancer or distinguishing conditions or indications selected from healthy conditions and cancer. Especially preferred are the indications 1), 2), 3), 4), 5), 6) and 7) mentioned above.

The kit may also comprise normalization standards, that result in a signal independent of a healthy condition and cancerous condition. Such normalization standards can be used to obtain background signals. Such standards may be specific for ubiquitous antibodies found in a human, such as antibodies against common bacteria such as *E. coli*. Preferably the normalization standards include positive and negative (leading to no specific signal) normalization standards.

The present invention is further illustrated by the following figures and examples, without being limited to these embodiments of the invention.

EXAMPLES

Example 1: Patient Samples

Biomarker screening has been performed with plasma samples from a test set of plasma samples derived from 99 individuals with confirmed lung carinoma, comprising 24 patients with adenocarcinoma, 25 patients with large cell carcinoma, 25 patients with small cell carcinoma and 25 patients with squamous cell carcinoma, and 93 healthy controls (n=192). All these individuals underwent chest radiography. The differentiation of carcinoma (denoted Carc), and controls (denoted Contr) was conducted during clinical examination of patients and tissue samples.

Example 2: Immunoglobuline (IgG) Purification from the Serum or Plasma Samples

The patient serum or plasma samples were stored at −80° C. before they were put on ice to thaw them for IgG purification using Melon Gel 96-well Spin Plate according the manufacturer's instructions (Pierce). In short, 10 µl of thawed sample was diluted in 90 µl of the equilibrated purification buffer on ice, then transferred onto Melon Gel support and incubated on a plate shaker at 500 rpm for 5 minutes. Centrifugation at 1,000×g for 2 minutes was done to collect the purified IgG into the collection plate.

Protein concentrations of the collected IgG samples were measured by absorbance measures at 280 nm using an Epoch Micro-Volume Spectrophotometer System (Biotec, USA). IgG-concentrations of all samples were concentration-adjusted and 0.6 mg/ml of samples were diluted 1:1 in PBS2× buffer with TritonX 0.2% and 6% skim milk powder for microarray analyses.

Example 3: Microarray Design

A protein-chip named "16 k protein chip" from 15284 human cDNA expression clones derived from the Unipex cDNA expression library plus technical controls was generated. Using this 16 k protein chip candidate markers were used to identify auto-antibody profiles suitable for unequivocal distinction of healthy conditions and lung cancer.

Protein-microarray generation and processing was using the Unipex cDNA expression library for recombinant protein expression in *E. coli*. His-tagged recombinant proteins were purified using Ni-metal chelate chromatography and proteins were spotted in duplicates for generation of the microarray using ARChipEpoxy slides.

Example 4: Preparation, Processing and Analyses of Protein Microarrays

The microarray with printed duplicates of the protein marker candidates was blocked with DIG Easy Hyb (Roche) in a stirred glass tank for 30 minutes. Blocked slides were washed 3× for 5 minutes with fresh PBSTritonX 0.1% washing buffer with agitation. The slides were rinsed in distilled water for 15 seconds to complete the washing step and remove leftovers from the washing buffer. Arrays were spun dry at 900 rpm for 2 minutes. Microarrays were processed using the Agilent Microarray Hybridisation Chambers (Agilent) and Agilent's gasket slides filled with 490 μl of the prepared sample mixture and processed in a hybridization oven for 4 h at RT with a rotation speed of 12. During this hybridization time the samples were kept under permanent rotating conditions to assure a homolog dispensation.

After the hybridization was done, the microarray slides were washed 3× with the PBSTritonX 0.1% washing buffer in the glass tank with agitation for 5 minutes and rinsed in distilled water for about 15 seconds. Then, slides were dried by centrifugation at 900 rpm for 2 minutes. IgG bound onto the features of the protein-microarrays were detected by incubation with cy5 conjugated Alexa Fluor® 647 Goat Anti-Human IgG (H+L) (Invitrogen, Lofer, Austria), diluted in 1:10,000 in PBSTritonX 0.1% and 3% skim milk powder using rotating conditions for 1 h, with a final washing step as outlined above. Microarrays were then scanned and fluorescent data extracted from images (Fig. 1) using the GenePixPro 6.0 software (AXON).

Example 5: Data Analysis

Data were 1) quantile normalised and alternatively 2) quantile normalized and additionally adjusted for batch effects with ComBat when samples were processed on microarrays in 6 different runs; data analyses was conducted using BRB array tools (web at linus.nci.nih.gov/BRB-ArrayTools.html) upon the 2 different normalization strategies (quantile and ComBat normalized).

For identification of tumor marker profiles and classifier markers, class prediction analyses applying leave-one-out cross-validation was used. Classifiers were built for distinguishing each of the five classes of samples denoted "Carc" carcinoma (adenocarcinoma or large cell carcinoma or small cell carcinoma or squamous cell carcinoma) patients, "AdCa" patients harboring adenocarcinoma, "LCLC" patients harboring large cell carcinoma, "SCLC" patients harboring small cell carcinoma, "SCC" patients harboring squamous cell carcinoma, and "Contr" individuals with no carcinoma. In addition different combinations of classes were also built as listed in the table below (Tab. 1) and again class prediction analysis was conducted for differentiation of these different combinations.

TABLE 1

Lung tumor marker Classifiers defined for separation of different indications (Contr.: for age, sex, and smoking behavior statistically balanced controls; AdCa: adenocarcinoma; LCLC: large cell lung cancer; SCLC: small cell lung cancer; SCC: squamous cell lung cancer). The various examples upon data analyses after different normalization strategies A) and B) are given.

| Contrast analysed | A) examples with quantile normalisation | B) examples with ComBat normalisation |
|---|---|---|
| 1) Contr vs Carcinoma | 7.1-7.4 | 7.26-7.28 |
| 2) Contr vs AdCa | 7.5-7.9 | |
| 3) Contr vs LCLC | 7.10-7.14 | |
| 4) Contr vs SCLC | 7.15-7.19 | |
| 5) Contr vs SCC | 7.20-7.24 | |
| 6) Contr vs LCLC & AdCa | 7.25 | |
| 7) Contr vs SqCC & SCLC | | 7.29 |

Example 6: Results Summary

For distinguishing 1) healthy conditions vs. cancer (adenocarcinoma or large cell carcinoma or small cell carcinoma or squamous cell carcinoma), 2) healthy conditions vs. adenocarcinoma, 3) healthy conditions vs. large cell carcinoma, 4) healthy conditions vs. small cell carcinoma, 5) healthy conditions vs. squamous cell carcinoma, 6) healthy conditions vs. large cell carcinoma plus adenocarcinoma, and 7) healthy conditions vs. squamous cell carcinoma plus small cell carcinoma, 52 genes were present in at least 5 classifier lists. The classification success with respect to different contrasts (differentiation of different patient classes and combinations thereof) and presence of 52 preferred List 2 markers is given in Table 2. As shown, the number of markers out of the 52 selected. Therefore the marker-lists, subsets and single markers (antigens; proteins;) are of particular diagnostic values.

TABLE 2

Data upon Quantil and ComBat normalisation have been analyzed with respect to different Contrasts given and classifiers generated by different class prediction methods, - the numbers of classifiers is depicted; out of these a valuable number of preferred 52 List 2 markers is present within those classifiers lists. Correct classification for each example is given in %. The right column refers to the number of the example.

| normalisation | number of markers | number of markers within list 2 | distinguished contrast | contrast # | correct classification | Example |
|---|---|---|---|---|---|---|
| Quantil normalised data | 99 | 27 | 1) Contr vs Carcinoma | 1 | 79% | 7.1 |
| | 100 | 11 | | 1 | 71% | 7.2 |
| | 99 | 19 | | 1 | 83% | 7.3 |
| | 99 | 6 | | 1 | 77% | 7.4 |

TABLE 2-continued

Data upon Quantil and ComBat normalisation have been analyzed with respect to different Contrasts given and classifiers generated by different class prediction methods, - the numbers of classifiers is depicted; out of these a valuable number of preferred 52 List 2 markers is present within those classifiers lists. Correct classification for each example is given in %. The right column refers to the number of the example.

| normalisation | number of markers | number of markers within list 2 | distinguished contrast | contrast # | correct classification | Example |
|---|---|---|---|---|---|---|
| | 99 | 16 | 2) Contr vs AdCa | 2 | 89% | 7.5 |
| | 100 | 18 | | 2 | 85% | 7.6 |
| | 50 | 3 | | 2 | 94% | 7.7 |
| | 98 | 16 | | 2 | 100% | 7.8 |
| | 50 | 8 | | 2 | 91% | 7.9 |
| | 99 | 15 | 3) Contr vs LCLC | 3 | 85% | 7.1 |
| | 99 | 18 | | 3 | 85% | 7.11 |
| | 50 | 4 | | 3 | 85% | 7.12 |
| | 97 | 13 | | 3 | 88% | 7.13 |
| | 50 | 4 | | 3 | 82% | 7.14 |
| | 100 | 16 | 4) Contr vs SCLC | 4 | 98% | 7.15 |
| | 50 | 4 | | 4 | 94% | 7.16 |
| | 99 | 13 | | 4 | 100% | 7.17 |
| | 95 | 8 | | 4 | 97% | 7.18 |
| | 50 | 3 | | 4 | 97% | 7.19 |
| | 100 | 12 | 5) Contr vs SCC | 5 | 88% | 7.20 |
| | 49 | 7 | | 5 | 90% | 7.21 |
| | 98 | 15 | | 5 | 94% | 7.22 |
| | 99 | 16 | | 5 | 89% | 7.23 |
| | 50 | 6 | | 5 | 97% | 7.24 |
| | 393 | 19 | 6) Contr vs LCLC & AdCa | 6 | 85% | 7.25 |
| ComBat normalised data | 50 | 13 | 1) Contr vs Carcinoma | 1 | 85% | 7.26 |
| | 99 | 15 | | 1 | 78% | 7.27 |
| | 50 | 14 | | 1 | 81% | 7.28 |
| | 100 | 6 | 7) Contr vs SqCC & SCLC | 7 | 96% | 7.29 |

Different classifier lists have been elucidated for the "contrasts" listed in Table 1, —upon A) quantile normalization (QNORM) and B) ComBat normalization.

Classifier markers (n=1389) were identified according to List 1. 129 markers were present in both sets of A) and B) normalized data; 1304 markers were present in classifier-sets upon A) quantile normalization, and 214 are present in classifiers upon ComBat normalization.

Upon marker annotation 0 markers present an identical protein, 0 duplicates can be removed and remaining unique make up a list of 1389 single Unigenes; thereof 129 are present in both sets of QNORM (A) and ComBat (B) normalized data; 1304 are present in classifiers upon QNORM, and an additional 214 are present in classifiers upon ComBat normalization.

Example 7: Detailed Results

Quantile-Normalized Data

Example 7.1: "All Carcinoma Vs. Healthy Controls"-100 Recursive Feature Elimination>79% 3NN The following markers were identified according to this example:
List 3:
ACO2 (includes EG:11429), ADH5 (includes EG:100145871), ADI1 (includes EG:104923), AGRN, AKAP13, AKR1C4, ALDOA, APBB1, ARHGDIA, ARH-GEF1, ARHGEF18, ATXN2L, BAZ1A, BCAS2, C10orf35, CCDC88C, CD81, CEP250, CLDN5, COL4A1, COMP, COPE, CUL7, D2HGDH, DUSP2, EDARADD, EIF3M, EPS8, ERCC5, EXOSC10, FAM192A, FAM21A/FAM21C, FBF1, FGFR3, FPGS, FYN, G3BP2, GABBR1, GGA2, GLOD4, GOLGA7, HERC2, HLA-E, HMGB2, IGHG1, KCTD15, KIF5A, LRP1 (includes EG:16971), MC1R, MDFIC, MED20, MEGF6, MUC2 (includes EG:4583), NECAP1, NEDD9, NFKB1, NFKBIA, NFYA, NLRC5, NLRP1, NOL11, PCBP1, PLCG1, PPP1CA, PPP6R1, PRMT1, PSAP, PSMC4, RCSD1, RPS25, RRP1B, RSBN1, SBK1, SETD2, SFN, SLC9A3R2, SMYD5, SNCB, SNRNP48, SREBF2, SRPR, SRRM2, SUMO1P3, TBCB, TMEM222, TOMM20 (includes EG:100043869), TP53 (includes EG:22059), TP53BP2, TRAK1, TRIM28, TRIM78P, TRIOBP, TXN2, UQCRC1, UTP14A, VIMP, WNK2, ZC3H13, ZEB1.

The "recursive feature elimination" strategy was used for class prediction of "all adenocarcinoma" samples including AdCa, SCLC, LCLC, and SCLC cases versus their age, sex, and smoking behavior statistically balanced Contr samples (contrast 1) using 192 samples (99 carcinoma, 93 controls). Using the recursive extraction of 100 features, for those 100 features the Support Vector Machine (SVM) predictor enabled correct classification of 100% of the tested samples. Feature subsetting and prediction was performed repeatedly for each of the K-fold (K=192) cross-validations of this subsetting method. By that means the rate of correct classification was calculated.

Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vectors Machines Correct? | Bayesian Compound Covariate Predictor Correct? |
|---|---|---|---|---|---|---|---|---|---|
| Mean percent of correct classification: | | | 69 | 71 | 75 | 79 | 69 | 77 | 74 |

Performance of the 3-Nearest Neighbors Classifier:

| Class | Sensitivity | Specificity | ppv | NPV |
|---|---|---|---|---|
| carcinoma | 0.758 | 0.828 | 0.824 | 0.762 |
| control | 0.828 | 0.758 | 0.762 | 0.824 |

Prior to feature subsetting only features higher expressed in carcinoma were selected for further processing. Feature subsetting and prediction was performed repeatedly for each of the K-fold (K=192) cross-validations of this subsetting method. By that means the rate of correct classification was calculated.

Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vectors Machines Correct? | Bayesian Compound Covariate Predictor Correct? |
|---|---|---|---|---|---|---|---|---|---|
| Mean percent of correct classification: | | | 69 | 69 | 68 | 71 | 69 | 70 | 79 |

Example 7.2: "All Carcinoma Vs. Healthy Controls" (Upregulated and Filtered Features)—100 Recursive Feature Elimination>71% 3NN The following markers were identified according to this example:
List 4:
ACBD5, ADAMDEC1, AKAP8, ANKRD12, AP1G1, AP1M1, ARFRP1, ATG16L1, AZGP1, BACE1, BICD2, BRD2, C11orf30, C1QTNF4, CBX4, CD74, CHST10, CLIP1, CLTC, CLUAP1, COL6A3, COPA, CTBP2, DAGLB, DDX54, DLG5, DNAJB1, EML3, FBXW5, FGFR3, FLOT1, FOSL2, GABBR1, GGA1 (includes EG:106039), HAUS7, HERC2, HOXB2, HSPA8, HSPG2, ID3, IL1B, IMPDH2, ISOC1, ITFG3, KRT73, LOC341056, LYSMD2, MED11 (includes EG:100148504), MED4 (includes EG:29079), METAP2, NAP1L1, NFATC1, NOTCH2, NPHP3, NR1H2, NSMCE1, NUMBL, OTUD4, PARP14, PCBP1, PFKL, PKM, POTEE/POTEF, PPP1R15B, PPP4C, PRC1 (includes EG:233406), PRRC2A, PSMA1, PSMB5, PSMC4, PSME4, QARS, RAI1, RAP2B, RASAL3, RECQL, RNF39, RPS19, SCAF1, SCML4, SMG5, SNRNP48, SNRPF, STAG2, SUMO1P3, TAPBPL, TBX21, TFRC, TGOLN2, TIAM1, TMC8, TMEM154, TP53 (includes EG:22059), UBFD1, VAT1, YLPM1, YWHAE, YWHAQ, ZAP70, ZNF837.
The "recursive feature elimination" strategy was used for class prediction of "all adenocarcinoma" samples including AdCa, SCLC, LCLC, and SCLC cases versus their age, sex, and smoking behavior statistically balanced Contr samples (contrast 1) using 192 samples. Using the recursive extraction of 100 features, for those 100 features the 3-Nearest-Neighbor (3NN) predictor enabled correct classification of 71% of the tested samples.

Performance of the 3-Nearest Neighbors Classifier:

| Class | Sensitivity | Specificity | PPV | NPV |
|---|---|---|---|---|
| carcinoma | 0.636 | 0.785 | 0.759 | 0.67 |
| control | 0.785 | 0.636 | 0.67 | 0.759 |

Example 7.3: "All Carcinoma Vs. Healthy Controls" (Using Just Runs 1-4)—50 Greedy Pairs>83% 1NN, SVM The following markers were identified according to this example:
List 5:
ADH5 (includes EG:100145871), ADI1 (includes EG:104923), AGT, AKR1C4, AP2M1, APLP1, ARCN1, ARHGDIA, ASAP1, B3GNT1, BNIP3L, C12orf32, C19orf66, CCT8, CD81, CDC42EP3, CFDP1, CNBP, COG4, COPS6, CORO2A, CTPS1, CYCS, DALRD3, DDX10, DDX41, DHX35, EIF3M, FABP7, FAM192A, FASN, FLYWCH1, FPGS, GNAI2, GNPDA1, H1F0, HNRNPAB, HSPA5, IL16, IMPDH2, ISOC1, ITPR3, JUNB, KIF5A, LRRC8B, MARCH2, MBD1, MEGF6, MORF4L1, NAGLU, NCOA3, NEK1, NLRC5, NPHP3, NPLOC4, NSUN5P1, OLFML3, PAM, PHF23, PHIP, PIN1, PPM1G, PSAP, PSMC4, R3HCC1, RABGGTB, RCSD1, RFC1, RIC8A, RPL18, RPS19, RPS4Y2, RTKN, SAMHD1, SGK2, SND1, SPHK2, SPTBN4, STAG1, STAT3, SUMO1P3, TAPBPL, TMUB2, TP53 (includes EG:22059), TRAK1, TRAP1, TRIM28, TRIOBP, TSR1, U2SURP, UQCRC1, USP7, WBP11, WDR24, WDR33, WDR73, ZC3H13, ZNF554, ZNFX1.

The "50 greedy pairs" strategy was used for class prediction, distinguishing "all adenocarcinoma" samples including AdCa, SCLC, LCLC, and SCLC cases versus their age, sex, and smoking behavior statistically balanced Contr samples (contrast 1) using only the first 139 samples (72 carcinoma, 67 healthy control), which were processed in runs 1-4. Using the "50 greedy pairs" the 1-Nearest-Neighbor (1NN) predictor and the Support Vector Machine (SVM) predictor enabled correct classification of 83% of the tested samples. Feature subsetting and prediction was performed repeatedly for each of the K-fold (K=139) cross-validations of this subsetting method. By that means the rate of correct classification was calculated.

MGA, MICAL1, MINA, MRPS18C, NECAP1, PARP14, PCBP1, PIGT, PIK3R5, POLR2J4, PPP1R15A, PRKAG1, PRSS53, PSMC5, RNF4, RPL13, RPS25, RRP9, S100A9, SCAF1, SIPA1, SIPA1L3, SLC4A2, SMG5, SOX4, SPTBN1, SRA1, SRM, SRRM2, SRSF2, STAT1, SYT1 (includes EG:20979), TBX21, TKT, TREX1, TRIP12, TUBGCP3, TWF2, UBAP1, UBXN1, USP30, USP42, UXT, VAT1, VIMP, YWHAE, ZFPL1, ZMIZ2, ZNF335, ZNF358, ZNF629, ZNF837.

The "50 greedy pairs" strategy was used for class prediction of "all adenocarcinoma" samples including AdCa, SCLC, LCLC, and SCLC cases versus their age, sex, and smoking behavior statistically balanced Contr samples (contrast 1) using the last 53 samples (27 carcinoma, 26 control) which were processed in runs 5 and 6. Using "50 greedy pairs" of features on arrays, the 3-Nearest-Neighbor, and the Support Vector Machine (SVM) Predictor enabled best correct classification of 77% of the tested samples.

Prior to feature subsetting features with less than 20% of expression data having least a 1.5-fold change in either direction from gene's median value, a percentile of the log-ratio variation in less than 75, and the 50th Percentile of intensities with less than a value of 500 got filtered out. Feature subsetting and prediction was performed repeatedly for each of the K-fold (K=53) cross-validations of this subsetting method. By that means the rate of correct classification was calculated.

Performance of Classifiers During Cross-Validation.

| | Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vectors Machines Correct? | Bayesian Compound Covariate Predictor Correct? |
|---|---|---|---|---|---|---|---|---|---|---|
| Mean percent of correct classification: | | | | 68 | 68 | 83 | 81 | 68 | 83 | 75 |

Performance of the 1-Nearest Neighbor Classifier:

| Class | Sensitivity | Specificity | PPV | NPV |
|---|---|---|---|---|
| carcinoma | 0.903 | 0.746 | 0.793 | 0.877 |
| control | 0.746 | 0.903 | 0.877 | 0.793 |

Performance of the Support Vector Machine Classifier:

| Class | Sensitivity | Specificity | PPV | NPV |
|---|---|---|---|---|
| carcinoma | 0.903 | 0.761 | 0.802 | 0.879 |
| control | 0.761 | 0.903 | 0.879 | 0.802 |

| | Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|---|
| Mean percent of correct classification: | | | | 72 | 70 | 74 | 77 | 72 | 77 | 76 |

Example 7.4: "All Carcinoma Vs. Healthy Controls" (Using Runs 5 and 6 and Feature Filtering)—50 Greedy Pairs>77% 3NN, SVM The following markers were identified according to this example:
List 6:
A2M, AATK, ANAPC2, ANKRD11, ANKRD13B, ARHGAP30, ATP5O, ATRX, ATXN2L, C11orf2, C11orf68, C19orf43, C7orf41, CCDC88A, CCDC88C, CCT5, CD2BP2, CNPPD1, COPA, CPE, CSTB, CTAGE5, CTC1, DNTTIP2, FAM213A, FGFBP3, FYN, GEN1, GOLGA8A/GOLGA8B, GOLGB1, GRN, HDAC2, HLA-C, HLA-E, HMGB2, HNRNPM, HSP90AA1, INF2, KIAA1462, KRT19 (includes EG:16669), LDHB (includes EG:3945), LRIG1, MAGI1, MAN2C1, MARS, MDFIC, MED15, Performance of the 3-Nearest Neighbors Classifier:

| Class | Sensitivity | Specificity | PPV | NPV |
|---|---|---|---|---|
| carcinoma | 0.667 | 0.885 | 0.857 | 0.719 |
| control | 0.885 | 0.667 | 0.719 | 0.857 |

Performance of the Support Vector Machine Classifier:

| Class | Sensitivity | Specificity | PPV | NPV |
|---|---|---|---|---|
| carcinoma | 0.741 | 0.808 | 0.8 | 0.75 |
| control | 0.808 | 0.741 | 0.75 | 0.8 |

Example 7.5: "Adenocarcinoma Vs. Healthy Controls"-100 Recursive Feature Elimination>89% SVM The following markers were identified according to this example:

List 7:

AAMP, AHCY, ANXA11, ANXA6, AP2M1, ARL6IP4, ARPC4, ASMTL, ATP5H, ATRX, BBS2, BEX4, C10orf35, C14orf129, C9orf16, CALR, CCT3, CDC123, CEP250, CUL7, DALRD3, DDR1, DDX19B, DNMBP, ELK1, EPHB3, F5, FAM192A, FAM208B, FKBP15, FLYWCH1, GANAB, GBE1, GPSM1, HIST1H1C, HNRNPC, HOOK2, IGF2, IGFBP6, INTS1, INTS9, LAMB1, LAMC2, LCP2, LRP1 (includes EG:16971), LRPAP1, MARS, MATK, MBD3 (includes EG:17192), MC1R, MORC2, MUC2 (includes EG:4583), NAGLU, NAV2, NELF, NFKB1, NKRF, NOL11, OGFR, PCDH7, PCGF2, PLXNB2, PODXL2, PPP1R15A, PPP6R1, PRDX5, PSMB1, PSMB8, RAPGEF1, RCSD1, RFC1, RPL37A, RPP40, RPS25, SEL1L3, SFI1 (includes EG:305467), SH3BGRL3, SIVA1, SLC35A2, SMG5, SNCB, SOX4, SRA1, STAT6, STRN4, STX16, SUMF2, SYTL1, TBC1D10B, TMEM222, TMEM230, TRAK1, TRIOBP, TSC22D3, TWF2, VRK1, WAPAL, ZNF146, ZNRF1.

The "recursive feature elimination" strategy was used for class prediction distinguishing Adenocarcinoma versus their age, sex, and smoking behaviour statistically balanced Contr samples (24 adenocarcinoma, 23 control) (contrast 2). Using the recursive extraction of 100 features, for those 100 features on the array the Support Vector Machine (SVM) predictor enabled correct classification of 89% of the tested samples.

Feature subsetting and prediction was performed repeatedly for each of the K-fold (K=47) cross-validations of this subsetting method. By that means the rate of correct classification was calculated.

Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 79 | 83 | 83 | 81 | 79 | 89 | 82 |

Performance of the Support Vector Machine Classifier:

| Class | Sensitivity | Specificity | PPV | NPV |
|---|---|---|---|---|
| ca_Adenocarcinoma | 0.917 | 0.87 | 0.88 | 0.909 |
| control | 0.87 | 0.917 | 0.909 | 0.88 |

Example 7.6: "Adenocarcinoma Vs. Healthy Controls"-100 Recursive Feature Elimination (Filtered Features)>85% 1NN The following markers were identified according to this example:

List 8:

AHCY, AKT3, ANXA6, AP1M1, ARPC4, ASNSD1, ATP1A3, ATP5H, ATRX, BEX4, BRK1, BZW1, C10orf35, C14orf129, C17orf101, C9orf16, CDKN2D, CEP250, CIAO1, CNBP, CUL7, DDX19B, DNMBP, DNTTIP2, EIF1, ELK1, EZR, FAM13A, FAM192A, FAM208B, FAM40A, FAM65B, GANAB, GBE1, HAPLN3, HECTD1, HIST1H1C, HOOK2, INTS9, KIF13B, LAMB1, LCP2, LRRC37A3 (includes others), MAD1L1, MARS, MATK, MED15, MEPCE, MUC2 (includes EG:4583), NAGLU, NAV2, NDUFS7, NFKB1, NKRF, NOL11, OGFR, OS9, PARP1, PLXNB2, PPP4C, PRDX5, PREP, PRKAG1, PSMB8, PSMC4, RALBP1, RAP1GAP, RAPGEF1, RCSD1, RPP40, RPS25, SERINC2, SH3BGRL3, SHKBP1, SMG5, SNCB, SOX4, SSRP1, STAT6, STRN4, SUMF2, SUMO1P3, TGS1, TMEM222, TP53 (includes EG:22059), TPM3, TRIOBP, TRPS1, TSC22D3, TWF2, UCHL3, UQCRC2, USP30, VIMP, VRK1, WAPAL, WDR11, XAF1, ZFPL1, ZNF146.

The "recursive feature elimination" strategy was used for class prediction distinguishing Adenocarcinoma versus their age, sex, and smoking behavior statistically balanced Contr samples (24 adenocarcinoma, 23 control) (contrast 2). Using the recursive extraction of 100 features, for those 100 features on the array the 1-Nearest-Neighbor (1NN) predictor enabled correct classification of 85% of the tested samples.

Prior to feature subsetting features with less than 20% of expression data having least a 1.5-fold change in either direction from gene's median value, a percentile of the log-ratio variation in less than 75, and the 50th Percentile of intensities with less than a value of 500 got filtered out. Feature subsetting and prediction was performed repeatedly for each of the K-fold (K=47) cross-validations of this subsetting method. By that means the rate of correct classification was calculated.

Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 77 | 77 | 85 | 83 | 79 | 81 | 76 |

Performance of the 1-Nearest Neighbor Classifier:

| Class | Sensitivity | Specificity | PPV | NPV |
|---|---|---|---|---|
| ca_Adenocarcinoma | 0.792 | 0.913 | 0.905 | 0.808 |
| control | 0.913 | 0.792 | 0.808 | 0.905 |

Performance of the Support Vector Machine Classifier:

| Class | Sensitivity | Specificity | PPV | NPV |
|---|---|---|---|---|
| ca_Adenocarcinoma | 0.917 | 0.957 | 0.957 | 0.917 |
| control | 0.957 | 0.917 | 0.917 | 0.957 |

Example 7.7: "Adenocarcinoma Vs. Healthy Controls"-25 Greedy Pairs>94% SVM

The following markers were identified according to this example:
List 9:
AP2M1, AP3D1, ARCN1, C3orf19, CCDC86, CSTB, DNAJA1, DYNC1H1, FAM120A, FAM208B, FAM32A, FNDC3A, FOXP4, HDAC10, HIST1H1C, HMGN2, HNRNPA2B1, HOXB3, HSF1 (includes EG:15499), IBA57 (includes EG:100330979), KHDRBS1, LARP4, MAP1A, MARS, MAST1, MCM6, MEPCE, MPST, MUC2 (includes EG:4583), NCOA4, NT5C3L, PCGF2, PPP6R1, PTPN1, RASSF7, RIC8A, RPL10A, RPL18, RPL37A, SAMD1, SDHB, SHKBP1, SIPA1L1, SSSCA1, TRAK1, TRIM28, TRIOBP, UBE2J2, WAPAL, ZMYM2.

The "25 greedy pairs" strategy was used for class prediction, and it was possible to very efficiently build classifiers for distinguishing adenocarcinoma versus their age, sex, and smoking behavior statistically balanced Contr samples (24 adenocarcinoma, 23 control) (contrast 2). Using "25 greedy pairs" of features on arrays, the Support Vector Machine (SVM) predictor enabled correct classification of 94% of the tested samples.

Feature subsetting and prediction was performed repeatedly for each of the K-fold (K=47) cross-validations of this subsetting method. By that means the rate of correct classification was calculated.

Performance of Classifiers During Cross-Validation.

Example 7.8: "Adenocarcinoma Vs. Healthy Controls" (Using Run 4)—100 Recursive Feature Elimination>100% 1NN The following markers were identified according to this example:
List 10:
AKR1A1, AKR7A2, AKT3, ANKRD24, ANXA1, AP2M1, AP3D1, ARCN1, ARL6IP4, ARPC4, ASAP1, ATP5H, BRF2, C19orf66, C1QTNF4, CBWD1, CCT3, CEP250, COX6B1, CSTF2T, DALRD3, EIF2A, EME2, FAM192A, FLYWCH1, GANAB, GART, GPS1, GPSM1, HAPLN3, HIST1H1C, HNRNPC, INPP5E, ITGA6, KCTD15, KIF1C, LOC285463, LRPAP1, LRRC37A3 (includes others), MAD1L1, MCM2, MEGF6, MLL3, MUC2 (includes EG:4583), N4BP3, NDST2, NELF, NHEJ1, NKRF, NR1H2, NUDT5, OGFR, PCGF2, PFAS, PJA2, PLCG1, PODXL2, PPP1CA, PPP4C, PSMB1, RANBP2, RAP1GAP, RAPGEF1, RFC1, RPP40, SAP30BP, SEC13, SEL1L3, SERBP1, SF3B3, SFI1 (includes EG:305467), SH3BGRL3, SHCBP1, SMCHD1, SNCB, SNRNP48, SNX15, SPTBN1, SRA1, STAT6, SYTL1, TACC2, TGS1, TMEM222, TMEM8A, TMSB10/TMSB4X, TP53 (includes EG:22059), TPM3, TRAF2, TRAF4, TRAK1, TRIM28, TRIOBP, UCHL3, UFD1L, VPS72 (includes EG:100001285), VRK1, ZFP36L2.

The "recursive feature elimination" strategy was used for class prediction, and it was possible to build classifiers for distinguishing adenocarcinoma versus their age, sex, and smoking behavior statistically balanced Contr samples (contrast 2) using just the first 34 samples (18 adenocarcinoma, 16 healthy controls processed in run 4). Using the recursive extraction of 100 features, for those 100 features on the array the Support Vector Machine (SVM) predictor enabled correct classification of 100% of the tested samples.

Feature subsetting and prediction was performed repeatedly for each of the K-fold (K=34) cross-validations of this subsetting method. By that means the rate of correct classification was calculated.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 85 | 87 | 91 | 91 | 85 | 94 | 88 |

Performance of Classifiers During Cross-Validation.

| | Array id | Class label | Mean Number of genes in classifier | Compound Covariate Predictor Correct? | Diagonal Linear Discriminant Analysis Correct? | 1- Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|---|
| Mean percent of correct classification: | | | | 94 | 91 | 100 | 97 | 97 | 97 | 97 |

Performance of the 1-Nearest Neighbor Classifier:

| Class | Sensitivity | Specificity | PPV | NPV |
|---|---|---|---|---|
| ca_Adenocarinoma | 1 | 1 | 1 | 1 |
| control | 1 | 1 | 1 | 1 |

Example 7.9: "Adenocarcinoma Vs. Healthy Controls" (Using Run 4)—100 Recursive Feature Elimination>91% 1NC The following markers were identified according to this example:
List 11:
AATK, AGRN, ANXA1, AP3D1, ARCN1, ASAP1, C3orf19, CEP250, CORO1A, DYNC1H1, FAM32A, FNDC3A, FOXP4, GGA1 (includes EG:106039), HIST1H1C, HSF1 (includes EG:15499), KIF1C, KLC4, KLHDC3, LAMB1, MAP1A, MEPCE, MTCH2, PCGF2, PPP1R15A, PPP4C, PTPN1, RFC1, RNF13, RPL18, SAMD1, SERPINF1, SETD2, SGCE, SH3BGRL3, SIPA1L1, SNCB, ST3GAL3, STX18, TACC2, TMEM222, TMEM59L, TMSB10/TMSB4X, TRAK1, TRIM28, TRIOBP, U2SURP, VRK1, WHSC2, ZNF439.

The "recursive feature elimination" strategy was used for class prediction, and it was possible to very efficiently build classifiers for distinguishing adenocarcinoma versus their age, sex, and smoking behavior statistically balanced Contr samples (contrast 2) using just the first 34 samples (18 adenocarinoma, 16 healthy controls) contained in run 4. Using "recursive feature elimination" of 100 samples the Nearest Centrod (NC) predictor enabled correct classification of 91% of the tested samples. Feature subsetting and prediction was performed repeatedly for each of the K-fold (K=34) cross-validations of this subsetting method. By that means the rate of correct classification was calculated.
Performance of Classifiers During Cross-Validation.

Performance of the Nearest Centroid Classifier:

| Class | Sensitivity ↓ | Specificity | PPV | NPV |
|---|---|---|---|---|
| ca_Adenocarinoma | 0.889 | 0.938 | 0.941 | 0.882 |
| control | 0.938 | 0.889 | 0.882 | 0.941 |

Example 7.10: "Large Cell Carcinoma Vs. Healthy Controls"-100 Recursive Feature Elimination>85% CCP, SVM The following markers were identified according to this example:
List 12:
AKR1B1, ANXA6, APOBR, ARHGAP30, ARID1B, ATP5SL, BCL11A, C11orf68, C2orf29, CAPN2, CCT3, CD81, CHMP1A, CLN6 (includes EG:315746), CLNS1A, COL4A1, CORO7/CORO7-PAM16, DDR1, DDX10, DHX16, DYNC1I2, ECSCR, EEF1A2, EIF2A, EIF3G, EPS8L3, ERCC5, FAM208A, FAM32A, FAM73A, FBXW5, FGFR3, GBP5, GLRX3, HNRNPA1, HNRPDL, IL17RA, L3MBTL2, LDB1, LOC285463, LOC494127, LOC644762, LPPR3, MAGED4/MAGED4B, MAP1B, MAPK6, MCRS1, MLL, NARS, NCL, NFATC1, NOTCH2, PAIP1, PARP1, PEPD, PES1, PLCB3, PLXNA2, POLR2J, PPP1R15A, PPP6R1, PRC1 (includes EG:233406), PRDX1, PRPF3, PRPF8, PSD4, PSMF1, PTPN4, RAI1, RARS2, RBM39, RFX5, RGS14, RNF166, RPL26, RPL28, RPP40, SETD2, SH2D2A, SLC9A3R2, SND1, SPAG7, SRA1, TAX1BP1, TCEA2, TRIOBP, TUBA1B, TXNIP, UBE2D2, UBE2Q1, UFD1L, USP7, UTP14A, WDR6, WDR90, XBP1 (includes EG:140614), ZC3H13, ZEB1, ZNF837.

The "recursive feature elimination" strategy was used for class prediction, and it was possible to build classifiers for distinguishing large cell carcinoma versus their age, sex, and smoking behavior statistically balanced Contr samples (25 large cell carcinoma, 23 controls) (contrast 3). Using the recursive extraction of 100 features, for those 100 features on the array the Compound Covariate Predictor (CCP) and the Support Vector Machine (SVM) predictor enabled correct classification of 85% of the tested samples.

| | Array id | Class label | Mean Number of genes in classifier | Compound Covariate Predictor Correct? | Diagonal Linear Discriminant Analysis Correct? | 1- Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|---|
| Mean percent of correct classification: | | | | 88 | 88 | 85 | 85 | 91 | 85 | 91 |

Feature subsetting and prediction was performed repeatedly for each of the K-fold (K=48) cross-validations of this subsetting method. By that means the rate of correct classification was calculated.

Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 85 | 81 | 77 | 75 | 75 | 85 | 85 |

Performance of the Compound Covariate Predictor Classifier:

| Class | Sensitivity | Specificity | PPV | NPV |
|---|---|---|---|---|
| ca_Large cell carcinoma | 0.84 | 0.87 | 0.875 | 0.833 |
| control | 0.87 | 0.84 | 0.833 | 0.875 |

Performance of the Support Vector Machine Classifier:

| Class | Sensitivity | Specificity | PPV | NPV |
|---|---|---|---|---|
| ca_Large cell carcinoma | 0.84 | 0.87 | 0.875 | 0.833 |
| control | 0.87 | 0.84 | 0.833 | 0.875 |

TBX21, TRIOBP, TSEN54, UBE2D2, UFD1L, UTP14A, UVSSA, WDR6, WDR90, WRB, ZC3H13, ZC3H7B, ZEB1, ZNF837.

The "recursive feature elimination" strategy was used for class prediction, and it was possible to build classifiers for distinguishing large cell carcinoma versus their age, sex, and smoking behavior statistically balanced Contr samples (25 large cell carcinoma, 23 controls) (contrast 3). Using the recursive extraction of 100 features, for those 100 features the Support Vector Machine (SVM) predictor enabled correct classification of 85% of the tested samples.

Prior to feature subsetting features with less than 20% of expression data having least a 1.5-fold change in either direction from gene's median value, a percentile of the log-ratio variation in less than 75, and the 50th Percentile of intensities with less than a value of 500 got filtered out. Feature subsetting and prediction was performed repeatedly for each of the K-fold (K=48) cross-validations of this subsetting method. By that means the rate of correct classification was calculated.

Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 83 | 79 | 75 | 73 | 81 | 85 | 83 |

Example 7.11: "Large Cell Carcinoma Vs. Healthy Controls" (Filtered Features)—100 Recursive Feature Elimination>85% SVM The following markers were identified according to this example:

List 13:

ACSS1, ANAPC2, ANKRD44, ANXA6, ATXN3, BCL11A, C11orf68, C19orf43, C2orf29, CAPN2, CCT3, CD81, CLDN5, CLN6 (includes EG:315746), COBRA1, DDX10, DDX54, DNAJA4, DNAJC11, EIF2A, EPS8L3, ERCC5, EZR, FAM32A, FBXW5, GBP5, GLE1 (includes EG:2733), GLRX3, GNL3, GRN, HDAC3, HDAC6, HDLBP, HINT1, HNRNPUL1, HNRPDL, IGF2R, IGHG1, ITFG3, KCNJ14, KRT73, LIN7C, LOC494127, L00644762, LPPR3, MAGI1, MAP1B, MCRS1, NELL2, NFATC1, NFKB1, NMT1, NOL11, OGFR, PAIP1, PARP1, PLCL2, PLD3, PLXNA2, PNMA1, POLR2J, PPP1R13B, PPP1R15A, PRC1 (includes EG:233406), PRDX1, PRPF8, PSD4, RAI1, RBM39, RNF166, RNF39, RPL18, RPL26, RPL28, RPP40, RSL1D1, SEC24B, SH2D2A, SLC3A2, SLC9A3R2, SMC1A, SNCB, SND1, SPAG7, TAP1, Performance of the Support Vector Machine Classifier:

| Class | Sensitivity | Specificity | PPV | NPV |
|---|---|---|---|---|
| ca_Large cell carcinoma | 0.8 | 0.913 | 0.909 | 0.808 |
| control | 0.913 | 0.8 | 0.808 | 0.909 |

Example 7.12: "Large Cell Carcinoma Vs. Healthy Controls"-25 Greedy Pairs>85% SVM The following markers were identified according to this example:

List 14:

AKR1B1, ATXN7L2, BMS1, C12orf32, CCDC56, CCT3, CD81, CHD3, CLN6 (includes EG:315746), CTPS1, DDOST, DDR1, DENND5A, EIF2B4, EPN2, GLE1 (includes EG:2733), GNAI2, HNRPDL, KAT6B, L00644762, LTBP3, MAP1B, MAPK8IP1, MEAF6, MLL4, MPP3, NCKAP5L, NCOA3, NNAT, PIK3R2, PKD1, PKN1, POLR2J, PPBP, RFX5, RPL15, SDHB, SEC24B, SENP2, SGSM3, SKIV2L2, SLC9A3R2, SMG6, SNRPD3, SYP, TADA3, TAX1BP1, TCEA2, TXN2, ZBTB22.

The "25 greedy pairs" strategy was used for class prediction, and it was possible to build classifiers for distinguishing large cell carcinoma versus their age, sex, and smoking behavior statistically balanced Contr samples (25 large cell carcinoma, 23 controls) (contrast 3). Using "25 greedy pairs" of features on arrays, the Support Vector Machine (SVM) predictor enabled correct classification of 85% of the tested samples.

Feature subsetting and prediction was performed repeatedly for each of the K-fold (K=48) cross-validations of this subsetting method. By that means the rate of correct classification was calculated.

Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 79 | 79 | 75 | 77 | 77 | 85 | 80 |

Performance of the Support Vector Machine Classifier:

| Class | Sensitivity | Specificity | PPV | NPV |
|---|---|---|---|---|
| ca_Large cell carcinoma | 0.84 | 0.87 | 0.875 | 0.833 |
| control | 0.87 | 0.84 | 0.833 | 0.875 |

SPECC1L, SPG7, SRSF4, SYNPO, TAF1C, TBX21, THBS1, TRIM44, TRNAU1AP, TSEN54, UBAP2L, UIMC1, USP7, UTP14A, YARS, YTHDF1, ZFYVE28, ZNF668, ZNFX1.

The "recursive feature elimination" strategy was used for class prediction, and it was possible to build classifiers for distinguishing "large cell carcinoma" versus their age, sex, and smoking behavior statistically balanced Contr samples (contrast 3) using just the first 34 samples (18 large cell carcinoma, 16 healthy controls) processed in run 3. Using the recursive extraction of 100 features, for those 100 features the 1-Nearest-Neighbor (1NN) and the 3-Nearest-Neighbor (3NN) predictor enabled correct classification of 88% of the tested samples.

Prior to feature subsetting only features higher expressed in carcinoma were selected for further processing. Feature subsetting and prediction was performed repeatedly for each of the K-fold (K=34) cross-validations of this subsetting method. By that means the rate of correct classification was calculated.

Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 85 | 82 | 88 | 88 | 85 | 82 | 85 |

Example 7.13: "Large Cell Carcinoma Vs. Healthy Controls" (Using Just Run 3 Only Upregulated Features)—100 Recursive Feature Elimination>88% 1NN, 3NN The following markers were identified according to this example:

List 15:
AKAP11, AKAP9, ANKRD11, ANKRD44, ARHGEF1, BINS, BMS1, BRD2, C12orf35, C17orf101, CAPN2, CD81, CDC123, CLIP1, CNOT2, CREM (includes EG:12916), CRIP1, CSNK2B, CUL7, DEF6, DENND5A, DENR, DIP2C, DNAJA4, DNLZ, ERCC5, FAM59A, FAM65B, FBXW5, FGFR3, GJA9, HERC2, HLA-B, IGH-MBP2, ITFG3, KARS, KIAA0947, LOC100130899, LOC389705, LOC440354, MAN2B1, MAP1B, MAP7D1, MBD3 (includes EG:17192), MLL, MVD, NCOA3, NPHP3, OBSCN, OS9, OSTM1, PABPC1, PAIP1, PCBP1, PHF3, PIPSL, PPP1R13B, PRC1 (includes EG:233406), PRDM8, PRPF19, PRRT1, PSMB8, PSME1, PTGS2, RAB-GGTB, RAI1, RBM15, RERE, RFX5, RNF39, RPS10, RPS19, SAP18, SCHIP1, SETD2, SF3B2, SMEK2, SND1, Performance of the 1-Nearest Neighbor Classifier:

| Class | Sensitivity | Specificity | PPV | NPV |
|---|---|---|---|---|
| ca_Large cell carcinoma | 0.889 | 0.875 | 0.889 | 0.875 |
| control | 0.875 | 0.889 | 0.875 | 0.889 |

Performance of the 3-Nearest Neighbors Classifier:

| Class | Sensitivity | Specificity | PPV | NPV |
|---|---|---|---|---|
| ca_Large cell carcinoma | 0.889 | 0.875 | 0.889 | 0.875 |
| control | 0.875 | 0.889 | 0.875 | 0.889 |

Example 7.14: "Large Cell Carcinoma Vs. Healthy Controls" (Using Just Run 3)—25 Greedy Pairs>82% 1NN The following markers were identified according to this example:

List 16:
AHSG, AKR1B1, CASP1, CCT6A, CELF3, CFDP1, EIF2B4, EIF4A2, FASN, FLII, FNTB, GNAI2, GPR56, HNRPDL, INPP5D, LCAT, LIN7C, LRRC47, LRWD1, LTBP3, MAP1B, MAP7D1, MAPK8IP1, MPP3, MYH9 (includes EG:17886), NBPF15 (includes others), NCOA3, NFIC, NOMO1 (includes others), OSTM1, PANK4, PFKM, PIGQ, PKD1, PMPCB, PNN, RBL2 (includes EG:100331892), RGS14, RPS19, SGTA, SLC9A3R2, SND1, SRSF1, STAU1, TPM3, TXN2, U2SURP, UBE2D4, UBE4A, ZNFX1.

The "25 greedy pairs" strategy was used for class prediction, and it was possible to build classifiers for distinguishing "large cell carcinoma" versus their age, sex, and smoking behavior statistically balanced Contr samples (contrast 3) using just the first 34 samples (18 large cell carcinoma, 16 healthy controls) contained in run 3. Using "25 greedy pairs" of features on arrays, the 1-Nearest-Neighbor (1NN) predictor enabled correct classification of 82% of the tested samples.

Feature subsetting and prediction was performed repeatedly for each of the K-fold (K=34) cross-validations of this subsetting method. By that means the rate of correct classification was calculated.

Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 79 | 79 | 82 | 79 | 76 | 79 | 81 |

Performance of the 1-Nearest Neighbor Classifier:

| Class | Sensitivity | Specificity | PPV | NPV |
|---|---|---|---|---|
| ca_Large cell carcinoma | 0.778 | 0.875 | 0.875 | 0.778 |
| control | 0.875 | 0.778 | 0.778 | 0.875 |

Example 7.15: SCLC Vs Contr—100 Recursive Features>98% SVM

The following markers were identified according to this example:

List 17:
ACTR1B, ADH5 (includes EG:100145871), AEBP1, AKR1C4, AP3D1, ARID5A, ATP5H, ATP6AP1, BEX4, BTBD6, CCT6A, CD74, CDC37, CDC42BPB, CDCA4, CENPB, CEP192, COMMD7, CRAT, CSRP1, CTSK, DCAF6, DIRAS3, DMPK, EDARADD, EIF1, EIF3D, EIF3M, ELAVL4, EPN1, EPS8, ERBB2, ERCC3, EXOSC10, FBLL1, FBXL17, FBXW5, FURIN, GJA9, GRN, HIVEP2, HNRNPUL1, HSPA5, HSPG2, INPPL1, IQGAP2, IWS1, KCTD15, LAT, LOC285463, LOC341056, LOXL2, MAGED4/MAGED4B, MAGI2, MARS, METTL3, MKLN1, MPST, MRPS9 (includes EG:301371), MYCBP2, NARFL, NECAP1, NEK1, NFKBIA, NOL11, NPEPL1, OFD1, P4HB, PHC2, PHF1, PHF3, PRKAR2A, PSMD6, PSTPIP1, RABGGTB, RASSF1, RFC1, RFX5, RPL18A, RPL26, SAP30BP, SEPN1, SIAH1, SLC35A2, SNCB, SRSF2, SIAM, SYNPO, TMEM184B, TMSB10/TMSB4X, TP53 (includes EG:22059), TRIOBP, TTYH1, TUBB4B, UNK, UQCRC1, USP39, VDAC1, ZNF439, ZNF592. For example the "recursive feature" strategy was used for class prediction of all SCLC vs their age, sex, and smoking behavior statistically balanced Contr samples (25 SCLC; 24 contr), and it was possible to very efficiently build a classifier for distinguishing classes. Using 100 recursive features on arrays, the Support Vector Machine predictor enabled correct classification of 98% of samples.

Recursive Feature Elimination method was used to select 100 genes. Repeated 1 times K-fold (K=49) cross-validation method was used to compute mis-classification rate.

Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 96 | 94 | 92 | 96 | 88 | 98 | 98 |

Performance of the Support Vector Machine Classifier:

| Class | Sensitivity | Specificity | PPV | NPV |
|---|---|---|---|---|
| ca_Small cell carcinoma | 1 | 0.958 | 0.962 | 1 |
| control | 0.958 | 1 | 1 | 0.962 |

Example 7.16: SCLC Vs Contr 25 Greedy Pairs>94% 1NN, SVM

The following markers were identified according to this example:

List 18:
ANKIB1, ANKRD54, AP2M1, BCR, BIRC5, CACNB3, CC2D1A (includes EG:212139), CDCA4, CHD8, CLIC1, CNPPD1, COA5, CORO2A, CRAT, DHX16, EDF1, EPS8L2, FAM21B, FGFBP3, GON4L, ILF3, INPP5E, INPPL1, IP6K1, LCMT1, LOC341056, MARCH2, MSLN, NEUROD2, NFATC4, NFKBIA, PHAX, PIN1, POLR2B, PTP4A3, PTPRA, QSOX2, RPL36A, SGSM3, SIAH1, SLC35B2, SMURF2, SRCAP, SYNE2, TMEM43, U2AF1, UBE2J2, VBP1, WBP11, WSB1. The "greed pairs" strategy was used for class prediction of all SCLC vs their age, sex, and smoking behavior statistically balanced Contr samples (25 SCLC; 24 contr), and a classifier for distinguishing classes was defined. Using 50 features on arrays, the 1-Nearest-Neighbor Analysis (1NN) and Support Vector Machine (SVM) predictors enabled correct classification of 94% of samples.

Greedy pairs algorithm was used to select 25 pairs of genes. Repeated 1 times K-fold (K=49) cross-validation method was used to compute mis-classification rate.

Performance of Classifiers During Cross-Validation.

| | Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|---|
| Mean percent of correct classification: | | | | 92 | 92 | 94 | 92 | 88 | 94 | 96 |

Performance of the 1-Nearest Neighbor Classifier:

| Class | Sensitivity | Specificity | PPV | NPV |
|---|---|---|---|---|
| ca_Small cell carcinoma | 0.92 | 0.958 | 0.958 | 0.92 |
| control | 0.958 | 0.92 | 0.92 | 0.958 |

Performance of the Support Vector Machine Classifier:

| Class | Sensitivity | Specificity | PPV | NPV |
|---|---|---|---|---|
| ca_Small cell carcinoma | 0.96 | 0.917 | 0.923 | 0.957 |
| control | 0.917 | 0.96 | 0.957 | 0.923 |

Example 7.17: SCLC Vs Contr 50 Greedy Pairs (Filtered Features)>100% SVM

The following markers were identified according to this example:

List 19:
ACBD5, ACTR1B, ADH5 (includes EG:100145871), AKR1C4, ANXA6, ANXA7, ARHGEF11, BCL9, C17orf28, C17orf56, CBWD1, CC2D1A (includes EG:212139), CDCA4, CEP192, CHCHD7, CHKB, CISH, CLK1, CNPPD1, COMMD7, CRAT, CTPS1, CYTIP, DDX24, DDX39B, DMPK, DNM2, DOT1L, EFR3A, EIF3D, ELAVL4, EPS8, ERCC3, EXOSC10, EXT2, FAM181A, GJA9, GON4L, GPR98, HIC1, HIVEP2, HSPA1A/HSPA1B, IMPDH2, INPPL1, IQGAP2, KIF21B, KIF22, KLF6, LAT, LAT2, LMF2, LOC341056, LOXL2, MARS, MED11 (includes EG:100148504), METTL3, MPST, MTA1, NAP1L1, NECAP1, NFKB1, NIP7, NXPH3, PA2G4, PCBP1, PLXNB1, POLR2J4, PPP1R8, PSMD6, PUF60, QSOX2, RAB43, RABGGTB, RALGDS, RCSD1, RPAP2, RPL18A, SAP30BP, SLC44A2, SREBF2, SRSF2, SSH3, SIAM, SUMO1P3, SUPV3L1, TGOLN2, TMEM173, TMEM184B, TP53 (includes EG:22059), TRIM28, TSC2, TUBB4B, UBXN4, USP39, WSB1, ZC3H13, ZCCHC9, ZNF12, ZNF260. The "greed pairs" strategy was used for class prediction of all SCLC vs their age, sex, and smoking behavior statistically balanced Contr samples (25 SCLC; 24 contr), and a classifier for distinguishing classes was defined. Using 100 features on arrays, the Support Vector Machine (SVM) predictors enabled correct classification of 100% of samples.

Prior to feature subsetting features with less than 20% of expression data having least a 1.5-fold change in either direction from gene's median value, a percentile of the log-ratio variation in less than 75, and the 50th Percentile of intensities with less than a value of 500 got filtered out. Greedy pairs algorithm was used to select 50 pairs of genes. Repeated 1 times K-fold (K=49) cross-validation method was used to compute mis-classification rate.

Performance of Classifiers During Cross-Validation.

| | Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|---|
| Mean percent of correct classification: | | | | 94 | 92 | 92 | 94 | 90 | 100 | 93 |

Performance of the Support Vector Machine Classifier:

| Class | Sensitivity | Specificity | PPV | NPV |
|---|---|---|---|---|
| ca_Small cell carcinoma | 1 | 1 | 1 | 1 |
| control | 1 | 1 | 1 | 1 |

Example 7.18: SCLC Vs. Contr (Run 1)—100 Recursive Features>97% CCP

The following markers were identified according to this example:

List 20:
ACTR1B, AKNA, AKR1C4, ALB, ARAF, ATRX, BAG1, BCL6, BCL9, BINS, C9orf86, CC2D1A (includes EG:212139), CCND1, CD74, CD97, CDCA4, CEP192, CEP76, COG4, COL3A1, COMMD9, CPE, CTSK, DCAF6, DDX39B, DLD, DMPK, ECSCR, EIF3D, EIF3M, ENTPD6, EPS8L2, EXOSC10, EXT2, FBLL1, FBXW5, FURIN, HAPLN3, INPPL1, IQGAP2, KLF4, KLHL23/PHOSPHO2-KLHL23, LAMA5, LMO4, LOC285463, LOXL2, MAZ, METTL3, MKLN1, MPST, MUC5AC/MUC5B, MYCBP2, NARFL, NBPF15 (includes others), NEK1, NFKBIA, NOA1, NOL12, NPEPL1, NRAS (includes EG:18176), PARP1, PLXNB1, POLR2A, PPP1R1B, PRDX1, PRPF31, PSMB5, PSMF1, RNF135, RPL26, RPS17/RPS17L, SART3, SCAF4, SEC13, SECISBP2, SEPN1, SLC44A2, SNX1, SUPV3L1, TARS2, TGS1, TOMM34, TP53 (includes EG:22059), TPI1P2, TSC2, TTC27, UBE2J2, UNK, UQCRC1, USP39, VDAC1, ZNF12, ZNF428, ZNF439, ZNF574. Alternatively to the "greedy pairs" strategy for class prediction of the first 36 (18 SCLC; 18 contr) samples, including SCLC cases and their age, sex, and smoking behaviour statistically balanced Contr samples, processed in run 1, the "Recursive feature" extraction strategy was used and selection of 100 features enabled 97% correct classification using the CCP method.

Recursive Feature Elimination method was used to select 100 genes. Repeated 1 times K-fold (K=36) cross-validation method was used to compute mis-classification rate.
Performance of Classifiers During Cross-Validation.

Performance of the Compound Covariate Predictor Classifier:

| Class | Sensitivity | Specificity | PPV | NPV |
|---|---|---|---|---|
| ca_Small cell carcinoma | 0.944 | 1 | 1 | 0.947 |
| control | 1 | 0.944 | 0.947 | 1 |

Example 7.19: SCLC Vs. Contr (Run 1)—25 Greedy Pairs>97% 3NN, NC

The following markers were identified according to this example:

List 21:

AKNA, AP2M1, APBA2, BCL9, BCR, CC2D1A (includes EG:212139), CDCA4, CLIC1, CNPPD1, CORO2A, DHX16, EDF1, EEF1D, GABARAPL2, GART, GPR98, GTF3C1, HSPA9, IP6K1, ITFG3, KIF4A, LCMT1, MCM3AP, MOB4, MPST, MRPS24, NDUFAB1, NFATC4, OPA1, PEF1, PHAX, PKP3, POLR2B, PPM1F, PTPRA, QSOX2, RCSD1, RUSC2, SAP30BP, SEPN1, SF3B2, SGSM3, SIAH1, SLC35B2, SRCAP, TMEM160, U2AF1, U2SURP, UBE2J2, WBP11. The "greedy pairs" strategy was used for class prediction of the first 36 (18 SCLC; 18 contr) samples, including SCLC cases and their age, sex, and smoking behavior statistically balanced Contr samples, processed in run 1, and it was possible to very efficiently build classifiers for distinguishing "Contr" versus "SCLC". Using "25 greedy pairs" of features on arrays, the 3-Nearest Neighbor (3NN) and Nearest Centroid (NC) Predictors enabled best correct classification of 97% of samples.

Greedy pairs algorithm was used to select 25 pairs of genes. Leave-one-out cross-validation method was used to compute mis-classification rate.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 97 | 89 | 92 | 94 | 92 | 94 | 97 |

Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 94 | 94 | 94 | 97 | 97 | 94 | 97 |

Performance of the 3-Nearest Neighbors Classifier:

| Class | Sensitivity | Specificity | PPV | NPV |
|---|---|---|---|---|
| ca_Small cell carcinoma | 1 | 0.944 | 0.947 | 1 |
| control | 0.944 | 1 | 1 | 0.947 |

Performance of the Nearest Centroid Classifier:

| Class | Sensitivity | Specificity | PPV | NPV |
|---|---|---|---|---|
| ca_Small cell carcinoma | 1 | 0.944 | 0.947 | 1 |
| control | 0.944 | 1 | 1 | 0.947 |

Example 7.20: "SCC Vs Contr"—100 Recursive Feature Extr>88% SVM

The following markers were identified according to this example:
List 22:
ABT1, ACTN4, ADI1 (includes EG:104923), AKR1C4, APBB1, ARHGDIA, ATP1A3, ATRX, BCL11A, BLMH, C10orf35, CD81, CEP70, CHD3, CLASRP, CNKSR3, COPA, CRAMP1L, CSTB, DNAJB1, DNAJC11, DUS3L, DYNC1I2, ENTPD6, EPS8, ETFA, FADD, FAM192A, FBRS, FKBP10, FKBP1A, FYN, GLOD4, GLRX3, GRN, HAX1, HINFP, HLA-A, HLA-B, HNRNPK, HNRNPR, INPP4A, ITK, LAMB1, LOC285463, LSM14A, LSP1 (includes EG:16985), MAP7D1, MFHAS1, MLH3 (includes EG:217716), MSL1 (human), NAA25, NARFL, NCOA4, NDUFA10, NDUFS2, NECAP1, NFRKB, NIPAL3, NOL11, NUDC, NUMA1, OBFC1, OTUD1, PARP10, PEX1 (includes EG:100534854), PHC2, PIGR, PPID, PPP1CA, PRMT6, PRPS1, PSMA1, PUF60, RAD21, RGS1, RPL17, RPS15, SCML4, SEC24C, SF3A1, SIRT7, SKP1/SKP1P2, SLC3A2, SLK, SMG5, SPTAN1, SRA1, STAB1, STAT4, TBC1D10A, TMUB2, TP53BP2, TSPYL2, UBE2N, UFD1L, WASL, ZC3H3 (includes EG:223642), ZNF333, ZXDC. For example the "recursive feature" strategy was used for class prediction of all SCC vs their age, sex, and smoking behavior statistically balanced Contr samples (25 SCC; 23 contr), and it was possible to very efficiently build a classifier for distinguishing classes. Using 100 recursive features on arrays, the Support Vector Machine predictor enabled correct classification of 88% of samples.

Recursive Feature Elimination method was used to select 100 genes. Repeated 1 times K-fold (K=48) cross-validation method was used to compute mis-classification rate.

Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 83 | 83 | 79 | 79 | 75 | 88 | 83 |

Performance of the Support Vector Machine Classifier:

| Class | Sensitivity | Specificity | PPV | NPV |
|---|---|---|---|---|
| ca_Squamous cell carcinoma | 0.8 | 0.957 | 0.952 | 0.815 |
| control | 0.957 | 0.8 | 0.815 | 0.952 |

Example 7.21: SCC Vs Contr 25 Greedy Pairs>90% DLDA

The following markers were identified according to this example:
List 23:
ACTB, AIM1 (includes EG:11630), AKR1C4, BEX4, CD81, CELF3, CHMP1A, CHMP1B, CRAMP1L, CRAT, DDR1, DIRAS3, DVL2, EDC4, ETFA, EXOSC5, FBN3, FBXO44, GSK3A, HNRNPA2B1, HNRNPAB, HNRNPH1, IL32, LONP1, MAPK7, MBD4, MSTO1, NARFL, NARS2, NCAPG, NUF2, NUMA1, PFKM, PPL, RBM39, RPL9, RPS15, RPS4Y2, SLK, SORD, SRA1, TMEM222, TOE1, TRIM8, U2SURP, WASL, XPO1, ZEB1, ZNFX1.

The "greed pairs" strategy was used for class prediction of all SCC vs their age, sex, and smoking behavior statistically balanced Contr samples (25 SCC; 23 contr), and a classifier for distinguishing classes was defined. Using 50 features on arrays, the Diagonal Linear Discriminant Analysis (DLDA) predictor enabled correct classification of 90% of samples.

Greedy pairs algorithm was used to select 25 pairs of genes. Repeated 1 times K-fold (K=48) cross-validation method was used to compute mis-classification rate.

Performance of Classifiers During Cross-Validation.

| | Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|---|
| Mean percent of correct classification: | | | 83 | 90 | 75 | 75 | 75 | 83 | 88 | |

Performance of the Diagonal Linear Discriminant Analysis Classifier:

| Class | Sensitivity | Specificity | PPV | NPV |
|---|---|---|---|---|
| ca_Squamous cell carcinoma | 0.92 | 0.87 | 0.885 | 0.909 |
| control | 0.87 | 0.92 | 0.909 | 0.885 | log-ratio variation in less than 75, and the 50th Percentile of intensities with less than a value of 500 got filtered out. Greedy pairs algorithm was used to select 50 pairs of genes. Repeated 1 times K-fold (K=48) cross-validation method was used to compute mis-classification rate.

Performance of Classifiers During Cross-Validation.

| | Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|---|
| Mean percent of correct classification: | | | 83 | 85 | 92 | 94 | 83 | 90 | 86 | |

Example 7.22: SCC Vs Contr 50 Greedy Pairs (Filtered Features)>94% 3NN

The following markers were identified according to this example:

List 24:
ABT1, ACO2 (includes EG:11429), AIM1 (includes EG:11630), AKR1C4, ALG3, AP2M1, ARID5A, BCL11A, CARD11, CC2D1A (includes EG:212139), CD81, CHD3, CHMP1B, CLC, CLIP1, CNKSR3, COPA, CRAT, DAXX, DDX27, DDX56, DIRAS3, DNAJB1, DNAJC11, DSE, EIF4H, ENTPD6, EXOC6, FAM40A, FASN, FEM1A, FKBP10, GEN1, GLOD4, GRN, HAX1, HLA-B, ISM1, ISOC1, ITFG3, KHDRBS1, LAMA5, LAMB1, MBD4, MFHAS1, MTM1, MUS81, MYO1F, NAA25, NARFL, NDFIP2, NECAP1, NET1 (includes EG:10276), NOL12, NR1H2, NUMA1, NYNRIN, OBFC1, OTUD1, PARP10, PDXDC1, PFKM, PIGR, PLEC, PPP1CA, PPP4C, PRPF8, PRRC2C, PSMA1, PSMC4, QARS, RAB14, RALBP1, RBM39, RCSD1, RPL9, SCRIB, SCYL1, SETD4, SFN, SH2D2A, SLK, SMG5, SNX17, SRRM2, SYNPO, TBC1D10A, TBR1, TBX21, TFF1, TMEM222, TMUB2, TOE1, TRAP1, TSC2, TXNRD1, VAT1, ZNFX1. The "greed pairs" strategy was used for class prediction of all SCC vs their age, sex, and smoking behaviour statistically balanced Contr samples (25 SCC; 23 contr), and a classifier for distinguishing classes was defined. Using 100 features on arrays, the 3-Nearest-Neighbor predictor enabled correct classification of 94% of samples.

Prior to feature subsetting features with less than 20% of expression data having least a 1.5-fold change in either direction from gene's median value, a percentile of the Performance of the 3-Nearest Neighbors Classifier:

| Class | Sensitivity | Specificity | PPV | NPV |
|---|---|---|---|---|
| ca_Squamous cell carcinoma | 0.96 | 0.913 | 0.923 | 0.955 |
| control | 0.913 | 0.96 | 0.955 | 0.923 |

Example 7.23: SCC Vs. Contr (Run 2)—100 Recursive Features>89% CCP, DLDA

The following markers were identified according to this example:
List 25:
AAMP, AHCTF1, AKR1C4, ANKRD24, AP3D1, ARHGEF6, ATF1 (includes EG:100040260), ATG13 (includes EG:362164), ATP1A3, ATRX, BCL11A, BLMH, C10orf35, CARD11, CC2D1A (includes EG:212139), CD81, CDC27, CIRH1A, CNKSR3, CRYM, CSRNP1, DDX42, DIDO1, DUS3L, DYNC1I2, EIF3H, EIF4G1, ENTPD6, EPRS, ETFA, FAM40A, FAM59A, GLTSCR1, HINFP, HLA-B, IL32, ISM1, KCTD15, KLF4, LOC285463, MAPK8IP1, MARK3, MAZ, MTHFS, MYO1F, NARFL, NCOA6, NDUFA10, NFKBIA, NFRKB, NOL11, NRBP1, NRXN2, NUMA1, OBFC1, PAAF1, PARP10, PEPD, PEX1 (includes EG:100534854), PFKFB4, PIGQ, PIPSL, PPID, PPP1CA, PPP1R2, PRMT6, PSMC4, RASSF1, RCSD1, REV3L, RIMBP3 (includes others), RPL7, RPP40, RPS15, RPS17/RPS17L, S1PR4, SCRIB, SDF4, SF3A1, SIL1 (includes EG:100334837), SKP1/SKP1P2, SLC3A2, SMC1A, SPTAN1, SRA1, TBCB, TLE3 (includes EG:100007463), TMEM184B, TMEM199, TOE1, TP53 (includes EG:22059), TPR, TRAK2, UBE2N, USP5, VAT1, VPS72 (includes EG:100001285), WASF1, ZBTB40.

Alternatively to the "greedy pairs" strategy for class prediction of the first 35 (18 SCC; 17 contr) samples, including SCC cases and their for age, sex, and smoking behavior statistically balanced Contr samples, processed in run 2, the "Recursive feature" extraction strategy was used and selection of 100 features enabled 89% correct classification using the CCP and DLDA method.

Recursive Feature Elimination method was used to select 100 genes. Repeated 1 times K-fold (K=35) cross-validation method was used to compute mis-classification rate.
Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 89 | 89 | 86 | 86 | 86 | 86 | 89 |

Performance of the Compound Covariate Predictor Classifier:

| Class | Sensitivity | Specificity | PPV | NPV |
|---|---|---|---|---|
| ca_Squamous cell carcinoma | 0.778 | 1 | 1 | 0.81 |
| control | 1 | 0.778 | 0.81 | 1 |

Performance of the Diagonal Linear Discriminant Analysis Classifier:

| Class | Sensitivity | Specificity | PPV | NPV |
|---|---|---|---|---|
| ca_Squamous cell carcinoma | 0.833 | 0.941 | 0.938 | 0.842 |
| control | 0.941 | 0.833 | 0.842 | 0.938 |

Example 7.24: SCC Vs. Contr (Run 2)—25 Greedy Pairs>97% SVM

The following markers were identified according to this example:

List 26:

AACS, ACOT7, ACTR1B, AGT, AIM1 (includes EG:11630), AKR1C4, APLP1, ARF3, BTBD10, BTBD2, CELF3, CHMP1B, CLIP1, DUSP8, EXOSC5, FAM21A/FAM21C, FBN3, FHL2, GSDMD, GSK3A, HADH, HMGB2, INTS1, KEAP1, LAMA5, LAMP1, MLL3, NARFL, NARS2, NCAPG, NDUFA10, NFRKB, NUMA1, OGFR, PARP10, PFKM, PMVK, PPP1R18, RAI1, RC3H2, SFXN1, SLC44A2, SMARCE1, SORD, SYT6, TAGLN3, TMEM199, TOE1, TUBA1B, USP15.

The "greedy pairs" strategy was used for class prediction of the first 35 (18 SCC; 17 contr) samples, including SCC cases and their for age, sex, and smoking behaviour statistically balanced Contr samples, processed in run 2, and it was possible to very efficiently build classifiers for distinguishing "Contr" versus "SCC". Using "25 greedy pairs" of features on arrays, the Support Vector Machine Predictor (SVM) enabled best correct classification of 97% of samples.

Greedy pairs algorithm was used to select 25 pairs of genes. Leave-one-out cross-validation method was used to compute mis-classification rate.
Performance of Classifiers During Cross-Validation.

| Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|
| Mean percent of correct classification: | | | 94 | 94 | 89 | 91 | 94 | 97 | 97 |

Performance of the Support Vector Machine Classifier:

| Class | Sensitivity | Specificity | PPV | NPV |
|---|---|---|---|---|
| ca_Squamous cell carcinoma | 0.944 | 1 | 1 | 0.944 |
| control | 1 | 0.944 | 0.944 | 1 |

Example 7.25: LCLC and AdCa Vs. Contr (Run 6 and Filtered Features)—PAM>85%

The following markers were identified according to this example:

List 27:

AATK, ACAA1, ACO2 (includes EG:11429), ACSS1, ACSS2, ADAMTS16, AHNAK, AK2, AKAP8, AKR1B1, ALDOA, ALKBH5, ANAPC2, ANKRD11, ANKRD13B, ANKRD44, APBB1IP, APOBR, APOL1, APOM, ARHGAP1, ARHGEF1, ATP13A2, ATP8B5P, ATRX, ATXN2L, BAD, BAP1, BAZ2A, BICD2, BNC2, BRPF1, BTRC, BYSL, BZRAP1, C17orf70, C19orf43, C1orf144, C20orf3, C21orf2, C5orf55, C7orf41, C8orf33, C9orf16, CALB2, CBLC, CCDC137, CCDC77, CCDC86, CCDC88A, CCNDBP1, CCT3, CCT5, CD40LG, CD81, CDCA4, CDK16, CDKN2D, CENPT, CEP70, CERK, CFP, CHD4, CHMP4B, CLK1, CLUAP1, CNBP, COBRA1, COL1A2, COL4A1, COL6A1, COMMD9, COQ6, COX6B1, CPNE1, CRIPAK, CSK, CTAGE5, CTTN, CUL7, DAZAP2, DBNL, DCTN1, DDX20, DDX51, DEDD2, DNAJA1, DNAJB1, DNAJC13, DNM2, DNMT1, DNTTIP2, DOCK2, DPYSL3, DRAP1, DUSP10, DVL2, EDF1, EGR2, EIF1, EIF2A, EIF2S2, EIF3A, EIF3H, EIF4G1, EIF5A, EIF5B, ELAVL4, ENTPD4, ERCC5, ESYT1, EXOC6, EZR, FAM160B2, FAM208B, FAM32A, FAM40A, FAM60A, FBF1, FIGNL1, FOXK1, FUT8, GEN1, GGA1 (includes EG:106039), GIMAP5, GLE1 (includes EG:2733), GLTSCR1, GNB2, GOLGA4, GOLM1, GON4L, GPATCH1, GSDMD, GYG1, GYS1, HADHA, HBP1, HDAC2, HECTD1, HERC2, HLA-A, HLA-C, HNRNPA2B1, HNRNPH3, HNRNPL, HNRNPM, HNRNPUL1, HSPA1A/HSPA1B, HYOU1, IARS2, IGHG1, IKZF5, IL1B, IL2RG, ILF3, INF2, INTS1, IQGAP2, IRF4, ISG15, IST1 (includes EG:307833), JUP, KAT7, KCNN4, KCTD15, KIAA0319L, KIAA1462, KIF13B, KIF2A, KPNA2, KRT73, KSR1, LAG3, LAMB1, LANCL2, LARP1, LAT, LENG8, LGMN, LRIG1, LRSAM1, MAGI1, MALT1, MAP7D1, MAPK8IP3, MARK3, MAST4, MAT2A, ME3, MED13, MED15, MED8 (includes EG:112950), MEGF6, MGA, MICALL2, MIIP, MLH1, MLL2, MLST8, MRPL49 (includes EG:18120), MYCBP2, MYO1F, NAGLU, NARF, NAV2, NET1 (includes EG:10276), NFATC1, NFX1, NHSL1, NMT1, NOLC1, NOTCH1, NOTCH2, NPIPL3 (includes others), NUP93, ODC1, OGFR, OS9, PA2G4, PARP1, PCBP1, PEX5, PEX6 (includes EG:117265), PHAX, PHC1, PHC2, PHF14, PHF20, PKD1, PKM, PKN1, PLCL2, PLD3, PLEKHB2, PLEKHJ1, PLEKHM1P, PMF1, PNMA1, POLR1D, POM121, PPA1, PPP1R15A, PPP2R2B, PPRC1, PRC1 (includes EG:233406), PRDX5, PRKCSH, PRPF8, PRRC2A, PSD4, PSMA1, PSMC4, PSMD1, PSMD6, PSME1, PTBP1, R3HDM2, RAD52 (includes EG:100426645), RAI1, RALGDS, RANGAP1, RAP1GAP, RAPGEF1, RARA, RASAL3, RASSF1, RASSF5, RASSF7, RCSD1, RELB, RFX5, RIPK1, RNF114, RPL13, RPL18, RPL22, RPL26, RPL7, RPLP0P2, RPS18, RPS25, RPS6KA1, RPTOR, RSL1D1, RSL24D1, SCAF11, SEC16A, SERBP1, SERINC2, SETD1B, SETD2, SETX, SF3A1, SF3B2, SH2D2A, SHE, SHKBP1, SIPA1, SKIV2L, SLC1A5, SLC4A3, SLC7A5, SLC9A3R2, SMARCB1, SMC1A, SMCHD1, SNF8, SNRNP48, SON, SOX4, SPAG7, SPG20, SPINT1, SPNS2, SPRR3, SRRM2, SRSF7, SS18, SSBP4, SSRP1, STAT1, STIM2, STK10, STOML2, SUMO1P3, SURF6, SUSD2, SYNPO, TACC2, TACC3, TADA2B, TAF1 (includes EG:270627), TALDO1, TAOK2, TAP1, TAP2, TBC1D1, TBCC, TBX21, TCHP, TFF1, TGOLN2, TNFAIP8L2, INKS, TNKS1BP1, TNRC6B, TOR1A, TPM3, TRADD, TRAF3IP3, TREX1, TRIAP1, TRIM66, TRIP12, TSC22D3, TSHZ1, TUBGCP6, TWF2, U2AF1, U2SURP, UBE2D2, UBR4, UBXN1, UQCRC1, USP30, UTP14A, UTY, VAV1, VCAN, VPS11, WBP2, WDR75, WDR90, XAF1, YTHDC1, YWHAE, ZAP70, ZC3H7A, ZC3H7B, ZC3HAV1, ZFPL1, ZMIZ2, ZNF12, ZNF146, ZNF227, ZNF253, ZNF358, ZNF554, ZNF629, ZNF830, ZNF837, ZNFX1, ZYX.

The "Prediction Analysis for Microarrays" (PAM) strategy was used for class prediction of the last 27 (13 SCLC; 14 contr) samples, including Adenocarcinoma and LCLC cases and their age, sex, and smoking behaviour statistically balanced Contr samples, processed in run 6, the PAM strategy was used and selection of 422 features enabled 85% correct classification.

Prior to feature subsetting features with less than 20% of expression data having least a 1.5-fold change in either direction from gene's median value, a percentile of the log-ratio variation in less than 75, and the 50th Percentile of intensities with less than a value of 500 got filtered out. Recursive Feature Elimination method was used and repeated 1 times K-fold (K=27) cross-validation method was used to compute mis-classification rate.

Performance of Classifier During Cross-Validation:

| Array id | Class label | Prediction Correct? | Prediction |
|---|---|---|---|
| Percent correctly classified: | | 85 | |

Performance of PAM Classifier During Cross-Validation:

| Class | Sensitivity | Specificity | PPV | NPV |
|---|---|---|---|---|
| carcinoma | 0.846 | 0.857 | 0.846 | 0.857 |
| control | 0.857 | 0.923 | 0.923 | 0.857 |

ComBat-Normalized Data:

Example 7.26: Carc Vs. Contr—25 Greedy Pairs>85% SVM

The following markers were identified according to this example:

List 28:

AGT, ARHGEF18, BCAS2, BRD2, C12orf32, CAP1, CD81, CFDP1, CLIP1, CNPPD1, EDC4, EIF3M, EPS8, FAM189B, FPGS, GSTM4, IMPDH2, KIF5A, MARCH2, MEGF6, MRPL10 (includes EG:107732), NFKB1, NONO, OCIAD2, OTUD1, PIN1, POLR2B, PRKAG1, PSMC4, R3HCC1, RABGGTB, RPL18, RPL9, RRP9, SGK2, SIRT7, SPTBN4, SRSF3, SUMO1P3, TANK, U2AF1, U2SURP, WBP11, WDR73, WHSC2, XPO4, ZC3H13, ZNF629, ZNF638, ZNFX1.

The "greedy pairs" strategy was used for class prediction of all 192 (99 Carc; 93 contr) samples, including AdCa, SCLC, LCLC, and SCLC cases and their age, sex, and smoking behavior statistically balanced Contr samples, and it was possible to very efficiently build classifiers for distinguishing "Contr" versus "Carc". Using "25 greedy pairs" of features on arrays, the Support Vector Machine (SVM) Predictor enabled best correct classification of 85% of samples.

Greedy pairs algorithm was used to select 25 pairs of genes. Leave-one-out cross-validation method was used to compute mis-classification rate.

Performance of Classifiers During Cross-Validation.

| | Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|---|
| Mean percent of correct classification: | | | | 70 | 72 | 74 | 73 | 69 | 85 | 82 |

Performance of the Support Vector Machine Classifier:

| Class | Sensitivity | Specificity | PPV | NPV |
|---|---|---|---|---|
| carcinoma | 0.848 | 0.849 | 0.857 | 0.84 |
| control | 0.849 | 0.848 | 0.84 | 0.85 |

Example 7.27: "All Carcinoma Vs. Healthy Controls"-50 Greedy Pairs>78% SVM

The following markers were identified according to this example:
List 29:
AGT, ALKBH2, ANXA6, APLP1, ARHGEF18, BCAS2, BRD2, C12orf32, C19orf66, CAP1, CCDC74A/CCDC74B, CCDC88C, CD81, CFDP1, CLIP1, CLPTM1, CNPPD1, CORO2A, CORO7/CORO7-PAM16, EDC4, EIF3M, EIF6, EPS8, ERBB3, FAM189B, FASN, FPGS, GNPDA1, GREM1, GRWD1, GSTM4, IL16, IMPDH2, ITGB2, JTB, KIF5A, MAGED2, MARCH2, MBD4, MEGF6, MRPL10 (includes EG:107732), MRPL23, NAP1L1, NARS2, NEFM, NFKB1, NFKBIA, NFYA, NONO, OCIAD2, OTUD1, PCBP1, PIN1, POLR2B, PRKAG1, PSMC2, PSMC4, R3HCC1, RAB3A, RABGGTB, RPL10, RPL18, RPL29 (includes EG:100039782), RPL9, RRP9, RUNDC3A, SEPT7, SERPINF1, SGK2, SIPA1L1, SIRT7, SORD, SPTBN4, SREBF2, SRRM2, SRSF3, SUMO1P3, TANK, TCEAL2, TMEM160, TMUB2, TSPAN7, TXLNA, TXN2, U2AF1, U2SURP, UBA1, USP10, WBP11, WDR73, WHSC2, XPO1, XPO4, ZC3H13, ZNF192, ZNF284, ZNF629, ZNF638, ZNFX1.

The "recursive feature elimination" strategy was used for class prediction of "all adenocarcinoma" versus "healthy controls" (contrast 1) using 192 samples (99 carcinoma, 93 controls). Using "50 greedy pairs" of features on arrays, the Support Vector Machine (SVM) Predictor enabled best correct classification of 78% of the tested samples.
Feature subsetting and prediction was performed repeatedly for each of the K-fold (K=53) cross-validations of this subsetting method. By that means the rate of correct classification was calculated.
Performance of Classifiers During Cross-Validation.

Performance of the Support Vector Machine Classifier:

| Class | Sensitivity | Specificity | PPV | NPV |
|---|---|---|---|---|
| carcinoma | 0.737 | 0.817 | 0.811 | 0.745 |
| control | 0.817 | 0.737 | 0.745 | 0.811 |

Example 7.28: Carc Vs. Contr (Run 1-4)—25 Greedy Pairs>81% 1NN, 3NN

The following markers were identified according to this example:
List 30:
APLP1, ARHGEF18, ASAP1, C19orf66, CD81, CDCA4, CFDP1, CLIP1, CNPPD1, COG4, CYFIP1, DDX10, DHX35, EIF3M, FABP7, FASN, FPGS, GNAI2, IL16, IMPDH2, JPH3, KIF5A, LRRC8B, MBD1, NONO, OCIAD2, PPM1G, PRPF4B, PSMC4, R3HCC1, RABGGTB, RPL29 (includes EG:100039782), RPL9, RPS4Y2, SIPA1L1, SPTBN4, SUMO1P3, TAPBPL, THAP7, TP53 (includes EG:22059), TRAP1, U2AF1, U2SURP, WBP11, WDR73, WHSC2, XPO4, ZC3H13, ZNF554, ZNFX1.

The "greedy pairs" strategy was used for class prediction of the first 139 (72 Carc; 67 contr) samples, including AdCa, SCLC, LCLC, and SCLC cases and their age, sex, and smoking behaviour statistically balanced Contr samples, and it was possible to very efficiently build classifiers for distinguishing "Contr" versus "Carc". Using "25 greedy pairs" of features on arrays, the 1-Nearest Neighbour (1NN) and 3-Nearest Neighbour (3NN) Predictors enabled best correct classification of 81% of samples.

Greedy pairs algorithm was used to select 25 pairs of genes. Leave-one-out cross-validation method was used to compute mis-classification rate.

| | Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|---|
| Mean percent of correct classification: | | | | 76 | 74 | 73 | 74 | 77 | 78 | 86 |

Performance of Classifiers During Cross-Validation.

| | Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|---|
| Mean percent of correct classification: | | | | 75 | 78 | 81 | 81 | 74 | 78 | 83 |

Performance of the 1-Nearest Neighbor Classifier:

| Class | Sensitivity | Specificity | PPV | NPV |
|---|---|---|---|---|
| carcinoma | 0.792 | 0.821 | 0.826 | 0.786 |
| control | 0.821 | 0.792 | 0.786 | 0.826 |

Performance of the 3-Nearest Neighbors Classifier:

| Class | Sensitivity | Specificity | PPV | NPV |
|---|---|---|---|---|
| carcinoma | 0.847 | 0.776 | 0.803 | 0.825 |
| control | 0.776 | 0.847 | 0.825 | 0.803 | prediction of the last 25 samples of SCLC and SCC vs their age, sex, and smoking behavior statistically balanced Contr (14 SCLC; 12 contr), and a classifier for distinguishing classes was defined. Using 100 features on arrays, the Compound Covariate Predictor (CCP), the Diagonal Linear Discriminant Analysis (DLDA), the 1-Nearest-Neighbor (1NN), the 3-Nearest-Neighbor (3NN), the Nearest Centroid (NC), and the Support Vector Machine (SVM) predictors enabled correct classification of 96% of samples.

Prior to feature subsetting features with less than 20% of expression data having least a 1.5-fold change in either direction from gene's median value, a percentile of the log-ratio variation in less than 75, and the 50th Percentile of intensities with less than a value of 500 got filtered out. Greedy pairs algorithm was used to select 50 pairs of genes. Repeated 1 times K-fold (K=26) cross-validation method was used to compute mis-classification rate.

Performance of Classifiers During Cross-Validation.

| | Array id | Class label | Mean Number of genes in classifier | Compound Covariate Predictor Correct? | Diagonal Linear Discriminant Analysis Correct? | 1-Nearest Neighbor | 3-Nearest Neighbors Correct? | Nearest Centroid Correct? | Support Vector Machines Correct? | Bayesian Compound Covariate Predictor Correct? |
|---|---|---|---|---|---|---|---|---|---|---|
| Mean percent of correct classification: | | | | 96 | 96 | 96 | 96 | 96 | 96 | 96 |

Example 7.29: SCLC and SCC Vs Contr (Run 5, Filtered Features) 50 Greedy Pairs>96% CCP, DLDA, 1NN, 3NN, NC, SVM The following markers were identified according to this example:
List 31:
ADAR, AFAP1, ATP5O, BEX4, C19orf21, C19orf43, C22orf28, CDC5L, CEBPB (includes EG:1051), CLASRP, CLN6 (includes EG:315746), CNDP2, COBRA1, CPNE8, DDX10, DDX41, DDX42, DIAPH1, DIEXF, DPP3, EIF3D, EPHB3, EPN1, EXOSC7, FBLL1, FKBP9L, GJA9, GLG1 (includes EG:20340), GLUL, GOLGA8A/GOLGA8B, GSTM2, HAUS4, HAX1, HNRNPUL1, HNRPDL, HSP90AB1, IRF4, KDM3B, KIF1C, KRBA1, LAMB1, LAS1L, LAT2, LCK, MED13L, MICAL1, MLL3, MPDU1, MRPS18C, MTHFD2, MUC1, NBPF15 (includes others), NDFIP2, NECAP1, NFKB1, NPEPL1, NRXN2, NUCB1, OBFC1, P4HB, PCID2, PEBP1, POLR2J4, PPP1CA, PPP1R26, PRKCQ, PRPS1, PTOV1, RAB14, RABGGTB, RASGRP2, RFX5, RGS2 (includes EG:19735), RNF4, RPL13, RPL36, RPS25, RRP36 (includes EG:100360664), SEMA3F, SETD4, SGCB, SIPA1L3, SIRT2, SLK, SMPD1, SPAG7, SREBF2, SSRP1, TCF7, TESC, TPI1P2, TRAF2, TRIM24, TUBGCP3, TWF2, USP11, USP42, VAT1, YAF2, ZNF256. The "greed pairs" strategy was used for class Performance of the Compound Covariate Predictor Classifier:

| Class | Sensitivity | Specificity | PPV | NPV |
|---|---|---|---|---|
| carcinoma | 1 | 0.917 | 0.933 | 1 |
| control | 0.917 | 1 | 1 | 0.933 |

Performance of the Diagonal Linear Discriminant Analysis Classifier:

| Class | Sensitivity | Specificity | PPV | NPV |
|---|---|---|---|---|
| carcinoma | 1 | 0.917 | 0.933 | 1 |
| control | 0.917 | 1 | 1 | 0.933 |

Performance of the 1-Nearest Neighbor Classifier:

| Class | Sensitivity | Specificity | PPV | NPV |
|---|---|---|---|---|
| carcinoma | 1 | 0.917 | 0.933 | 1 |
| control | 0.917 | 1 | 1 | 0.933 |

Performance of the 3-Nearest Neighbors Classifier:

| Class | Sensitivity | Specificity | PPV | NPV |
|---|---|---|---|---|
| carcinoma | 1 | 0.917 | 0.933 | 1 |
| control | 0.917 | 1 | 1 | 0.933 |

Performance of the Nearest Centroid Classifier:

| Class | Sensitivity | Specificity | PPV | NPV |
|---|---|---|---|---|
| carcinoma | 1 | 0.917 | 0.933 | 1 |
| control | 0.917 | 1 | 1 | 0.933 |

Performance of the Support Vector Machine Classifier:

| Class | Sensitivity | Specificity | PPV | NPV |
|---|---|---|---|---|
| carcinoma | 1 | 0.917 | 0.933 | 1 |
| control | 0.917 | 1 | 1 | 0.933 |

The invention claimed is:

1. A method comprising detecting autoantibodies that bind an antigenic fragment of one or more marker protein(s) in a sample from the patient; wherein the one or more marker protein(s) comprise AKR1C4.

2. The method of claim 1, further defined as comprising detecting lung cancer in the patient by detecting at least 2 or least 20% of the marker proteins selected from ACO2 (includes EG:11429), ADH5 (includes EG:100145871), ADI1 (includes EG:104923), AGRN, AKAP13, AKR1C4, ALDOA, APBB1, ARHGDIA, ARHGEF1, ARHGEF18, ATXN2L, BAZ1A, BCAS2, C10orf35, CCDC88C, CD81, CEP250, CLDN5, COL4A1, COMP, COPE, CULT, D2HGDH, DUSP2, EDARADD, EIF3M, EPS8, ERCC5, EXOSC10, FAM192A, FAM21A/FAM21C, FBF1, FGFR3, FPGS, FYN, G3BP2, GABBR1, GGA2, GLOD4, GOLGA7, HERC2, HLA-E, HMGB2, IGHG1, KCTD15, KIF5A, LRP1 (includes EG:16971), MC1R, MDFIC, MED20, MEGF6, MUC2 (includes EG:4583), NECAP1, NEDD9, NFKB1, NFKBIA, NFYA, NLRC5, NLRP1, NOL11, PCBP1, PLCG1, PPP1CA, PPP6R1, PRMT1, PSAP, PSMC4, RCSD1, RPS25, RRP1B, RSBN1, SBK1, SETD2, SFN, SLC9A3R2, SMYD5, SNCB, SNRNP48, SREBF2, SRPR, SRRM2, SUMO1P3, TBCB, TMEM222, TOMM20 (includes EG:100043869), TP53 (includes EG:22059), TP53BP2, TRAK1, TRIM28, TRIM78P, TRIOBP, TXN2, UQCRC1, UTP14A, VIMP, WNK2, ZC3H13, ZEB1, ACBD5, ADAMDEC1, AKAP8, ANKRD12, AP1G1, AP1M1, ARFRP1, ATG16L1, AZGP1, BACE1, BICD2, BRD2, C11orf30, C1QTNF4, CBX4, CD74, CHST10, CLIP1, CLTC, CLUAP1, COL6A3, COPA, CTBP2, DAGLB, DDX54, DLG5, DNAJB1, EML3, FBXW5, FLOT1, FOSL2, GGA1 (includes EG:106039), HAUS7, HOXB2, HSPA8, HSPG2, ID3, IL1B, IMPDH2, ISOC1, ITFG3, KRT73, LOC341056, LYSMD2, MED11 (includes EG:100148504), MED4 (includes EG:29079), METAP2, NAP1L1, NFATC1, NOTCH2, NPHP3, NR1H2, NSMCE1, NUMBL, OTUD4, PARP14, PFKL, PKM, POTEE/POTEF, PPP1R15B, PPP4C, PRC1 (includes EG:233406), PRRC2A, PSMA1, PSMB5, PSME4, QARS, RAIL RAP2B, RASAL3, RECQL, RNF39, RPS19, SCAF1, SCML4, SMG5, SNRPF, STAG2, TAPBPL, TBX21, TFRC, TGOLN2, TIAM1, TMC8, TMEM154, UBFD1, VAT1, YLPM1, YWHAE, YWHAQ, ZAP70, ZNF837, AGT, AP2M1, APLP1, ARCN1, ASAP1, B3GNT1, BNIP3L, C12orf32, C19orf66, CCT8, CDC42EP3, CFDP1, CNBP, COG4, COPSE, CORO2A, CTPS1, CYCS, DALRD3, DDX10, DDX41, DHX35, FABP7, FASN, FLYWCH1, GNAI2, GNPDA1, H1F0, HNRNPAB, HSPA5, IL16, ITPR3, JUNB, LRRC8B, MARCH2, MBD1, MORF4L1, NAGLU, NCOA3, NEK1, NPLOC4, NSUN5P1, OLFML3, PAM, PHF23, PHIP, PIN1, PPM1G, R3HCC1, RABGGTB, RFC1, RIC8A, RPL18, RPS4Y2, RTKN, SAMHD1, SGK2, SND1, SPHK2, SPTBN4, STAG1, STAT3, TMUB2, TRAP1, TSR1, U2SURP, USP7, WBP11, WDR24, WDR33, WDR73, ZNF554, ZNFX1, A2M, AATK, ANAPC2, ANKRD11, ANKRD13B, ARHGAP30, ATP5O, ATRX, C11orf2, C11orf68, C19orf43, C7orf41, CCDC88A, CCT5, CD2BP2, CNPPD1, CPE, CSTB, CTAGE5, CTC1, DNTTIP2, FAM213A, FGFBP3, GEN1, GOLGA8A/GOLGA8B, GOLGB1, GRN, HDAC2, HLA-C, HNRNPM, HSP90AA1, INF2, KIAA1462, KRT19 (includes EG:16669), LDHB (includes EG:3945), LRIG1, MAGI1, MAN2C1, MARS, MED15, MGA, MICAL1, MINA, MRPS18C, PIGT, PIK3R5, POLR2J4, PPP1R15A, PRKAG1, PRSS53, PSMC5, RNF4, RPL13, RRP9, S100A9, SIPA1, SIPA1L3, SLC4A2, SOX4, SPTBN1, SRA1, SRM, SRSF2, STAT1, SYT1 (includes EG:20979), TKT, TREX1, TRIP12, TUBGCP3, TWF2, UBAP1, UBXN1, USP30, USP42, UXT, ZFPL1, ZMIZ2, ZNF335, ZNF358, ZNF629, AAMP, AHCY, ANXA11, ANXA6, ARL6IP4, ARPC4, ASMTL, ATP5H, BBS2, BEX4, C14orf129, C9orf16, CALR, CCT3, CDC123, DDR1, DDX19B, DNMBP, ELK1, EPHB3, F5, FAM208B, FKBP15, GANAB, GBE1, GPSM1, HIST1H1C, HNRNPC, HOOK2, IGF2, IGFBP6, INTS1, INTS9, LAMB1, LAMC2, LCP2, LRPAP1, MATK, MBD3 (includes EG:17192), MORC2, NAV2, NELF, NKRF, OGFR, PCDH7, PCGF2, PLXNB2, PODXL2, PRDX5, PSMB1, PSMB8, RAPGEF1, RPL37A, RPP40, SEL1L3, SFI1 (includes EG:305467), SH3BGRL3, SIVA1, SLC35A2, STATE, STRN4, STX16, SUMF2, SYTL1, TBC1D10B, TMEM230, TSC22D3, VRK1, WAPAL, ZNF146, ZNRF1, AKT3, ASNSD1, ATP1A3, BRK1, BZW1, C17orf101, CDKN2D, CIAO1, EIF1, EZR, FAM13A, FAM40A, FAM65B, HAPLN3, HECTD1, KIF13B, LRRC37A3, MAD1L1, MEPCE, NDUFS7, OS9, PARP1, PREP, RALBP1, RAP1GAP, SERINC2, SHKBP1, SSRP1, TGS1, TPM3, TRPS1, UCHL3, UQCRC2, WDR11, XAF1, AP3D1, C3 orf19, CCDC86, DNAJA1, DYNC1H1, FAM120A, FAM32A, FNDC3A, FOXP4, HDAC10, HMGN2, HNRNPA2B1, HOXB3, HSF1 (includes EG:15499), IBA57 (includes EG:100330979), KHDRBS1, LARP4, MAP1A, MAST1, MCM6, MPST, NCOA4, NT5C3L, PTPN1, RASSF7, RPL10A, SAMD1, SDHB, SIPA1L1, SSSCA1, UBE2J2, ZMYM2, AKR1A1, AKR7A2, ANKRD24, ANXA1, BRF2, CBWD1, COX6B1, CSTF2T, EIF2A, EME2, GART, GPS1, INPP5E, ITGA6, KIF1C, LOC285463, MCM2, MLL3, N4BP3, NDST2, NHEJ1, NUDT5, PFAS, PJA2, RANBP2, SAP30BP, SEC13, SERBP1, SF3B3, SHCBP1, SMCHD1, SNX15, TACC2, TMEM8A, TMSB10/TMSB4X, TRAF2, TRAF4, UFD1L, VPS72 (includes EG:100001285), ZFP36L2, CORO1A, KLC4, KLHDC3, MTCH2, RNF13, SERPINF1, SGCE, ST3GAL3, STX18, TMEM59L, WHSC2, ZNF439, AKR1B1, APOBR, ARID1B, ATP5SL, BCL11A, C2orf29, CAPN2, CHMP1A, CLN6 (includes EG:315746), CLNS1A, CORO7/CORO7-PAM16, DHX16, DYNC1I2, ECSCR, EEF1A2, EIF3G, EPS8L3, FAM208A, FAM73A, GBP5, GLRX3, HNRNPA1, HNRNPDL, IL17RA, L3MBTL2, LDB1, LOC494127, LOC644762, LPPR3, MAGED4/MAGED4B, MAP1B, MAPK6, MCRS1, MLL, NARS, NCL, PAIP1, PEPD, PES1, PLCB3, PLXNA2, POLR2J, PRDX1, PRPF3, PRPF8, PSD4, PSMF1, PTPN4, RARS2, RBM39, RFX5, RGS14, RNF166, RPL26, RPL28, SH2D2A, SPAG7, TAX1BP1, TCEA2, TUBA1B, TXNIP, UBE2D2, UBE2Q1, WDR6, WDR90, XBP1 (includes EG:140614), ACSS1, ANKRD44, ATXN3, COBRA1, DNAJA4, DNAJC11, GLE1 (includes EG:2733), GNL3, HDAC3, HDAC6, HDLBP, HINT1, HNRNPUL1, IGF2R, KCNJ14, LIN7C, NELL2, NMT1, PLCL2, PLD3, PNMA1, PPP1R13B, RSL1D1, SEC24B, SLC3A2, SMC1A, TAP1, TSEN54, UVSSA, WRB, ZC3H7B, ATXN7L2, BMS1, CCDC56, CHD3, DDOST, DENND5A, EIF2B4, EPN2, KAT6B, LTBP3, MAPK8IP1, MEAF6, MLL4, MPP3, NCKAP5L, NNAT, PIK3R2, PKD1, PKN1, PPBP, RPL15, SENP2, SGSM3, SKIV2L2, SMG6, SNRPD3, SYP, TADA3, ZBTB22, AKAP11, AKAP9, BIN3, C12orf35, CNOT2, CREM (includes EG:12916), CRIP1, CSNK2B, DEF6, DENR, DIP2C, DNLZ, FAM59A, GJA9, HLA-B, IGHMBP2, KARS, KIAA0947, LOC100130899, LOC389705, LOC440354, MAN2B1, MAP7D1, MVD, OBSCN, OSTM1, PABPC1, PHF3, PIPSL, PRDM8, PRPF19, PRRT1, PSME1, PTGS2, RBM15, RERE, RPS10, SAP18, SCHIP1, SF3B2, SMEK2, SPECC1L, SPG7, 5R5F4, SYNPO, TAF1C, THBS1, TRIM44, TRNAU1AP, UBAP2L, UIMC1, YARS, YTHDF1, ZFYVE28, ZNF668, AHSG, CASP1, CCT6A, CELF3, EIF4A2, FLIT, FNTB, GPR56, INPP5D, LCAT, LRRC47, LRWD1, MYH9 (includes EG:17886), NBPF15, NFIC, NOMO1, PANK4, PFKM, PIGQ, PMPCB, PNN, RBL2 (includes EG:100331892), SGTA, SRSF1, STAU1, UBE2D4, UBE4A, ACTR1B, AEBP1, ARID5A, ATP6AP1, BTBD6, CDC37, CDC42BPB, CDCA4, CENPB, CEP192, COMMD7, CRAT, CSRP1, CTSK, DCAF6, DIRAS3, DMPK, EIF3D, ELAVL4, EPN1, ERBB2, ERCC3, FBLL1, FBXL17, FURIN, HIVEP2, INPPL1, IQGAP2, IWS1, LAT, LOXL2, MAGI2, METTL3, MKLN1, MRPS9 (includes EG:301371), MYCBP2, NARFL, NPEPL1, OFD1, P4HB, PHC2, PHF1, PRKAR2A, PSMD6, PSTPIP1, RASSF1, RPL18A, SEPN1, SIAH1, STAM, TMEM184B, TTYH1, TUBB4B, UNK, USP39, VDAC1, ZNF592, ANKIB1, ANKRD54, BCR, BIRC5, CACNB3, CC2D1A (includes EG:212139), CHD8, CLIC1, COA5, EDF1, EPS8L2, FAM21B, GON4L, ILF3, IP6K1, LCMT1, MSLN, NEUROD2, NFATC4, PHAX, POLR2B, PTP4A3, PTPRA, QSOX2, RPL36A, SLC35B2, SMURF2, SRCAP, SYNE2, TMEM43, U2AF1, VBP1, WSB1, ANXA7, ARHGEF11, BCL9, C17orf28, C17orf56, CHCHD7, CHKB, CISH, CLK1, CYTIP, DDX24, DDX39B, DNM2, DOT1L, EFR3A, EXT2, FAM181A, GPR98, HIC1, HSPA1A/HSPA1B, KIF21B, KIF22, KLF6, LAT2, LMF2, MTA1, NIP7, NXPH3, PA2G4, PLXNB1, PPP1R8, PUF60, RAB43, RALGDS, RPAP2, SLC44A2, SSH3, SUPV3L1, TMEM173, TSC2, UBXN4, ZCCHC9, ZNF12, ZNF260, AKNA, ALB, ARAF, BAG1, BCL6, C9orf86, CCND1, CD97, CEP76, COL3A1, COMMD9, DLD, ENTPD6, KLF4, KLHL23/PHOSPHO2-KLHL23, LAMA5, LMO4, MAZ, MUC5AC/MUC5B, NOA1, NOL12, NRAS (includes EG:18176), POLR2A, PPP1R1B, PRPF31, RNF135, RPS17/RPS17L, SART3, SCAF4, SECISBP2, SNX1, TARS2, TOMM34, TPI1P2, TTC27, ZNF428, ZNF574, APBA2, EEF1D, GABARAPL2, GTF3C1, HSPA9, KIF4A, MCM3AP, MOB4, MRPS24, NDUFAB1, OPA1, PEF1, PKP3, PPM1F, RUSC2, TMEM160, ABT1, ACTN4, BLMH, CEP70, CLASRP, CNKSR3, CRAMP1L, DUS3L, ETFA, FADD, FBRS, FKBP10, FKBP1A, HAX1, HINFP, HLA-A, HNRNPK, HNRNPR, INPP4A, ITK, LSM14A, LSP1 (includes EG:16985), MFHAS1, MLH3 (includes EG:217716), MSL1 (human), NAA25, NDUFA10, NDUFS2, NFRKB, NIPAL3, NUDC, NUMA1, OBFC1, OTUD1, PARP10, PEX1 (includes EG:100534854), PIGR, PPID, PRMT6, PRPS1, RAD21, RGS1, RPL17, RPS15, SEC24C, SF3A1, SIRT7, SKP1/SKP1P2, SLK, SPTAN1, STAB1, STAT4, TBC1D10A, TSPYL2, UBE2N, WASL, ZC3H3 (includes EG:223642), ZNF333, ZXDC, ACTB, AIM1 (includes EG:11630), CHMP1B, DVL2, EDC4, EXOSC5, FBN3, FBXO44, GSK3A, HNRNPH1, IL32, LONP1, MAPK7, MBD4, MSTO1, NARS2, NCAPG, NUF2, PPL, RPL9, SORD, TOE1, TRIMS, XPO1, ALG3, CARD11, CLC, DAXX, DDX27, DDX56, DSE, EIF4H, EXOC6, FEM1A, ISM1, MTM1, MUS81, MYO1F, NDFIP2, NET1 (includes EG:10276), NYNRIN, PDXDC1, PLEC, PRRC2C, RAB14, SCRIB, SCYL1, SETD4, SNX17, TBR1, TFF1, TXNRD1, AHCTF1, ARHGEF6, ATF1 (includes EG:100040260), ATG13 (includes EG:362164), CDC27, CIRH1A, CRYM, CSRNP1, DDX42, DIDO1, EIF3H, EIF4G1, EPRS, GLTSCR1, MARK3, MTHFS, NCOA6, NRBP1, NRXN2, PAAF1, PFKFB4, PPP1R2, REV3L, RIMBP3, RPL7, S1PR4, SDF4, SIL1 (includes EG:100334837), TLE3 (includes EG:100007463), TMEM199, TPR, TRAK2, USP5, WASF1, ZBTB40, AACS, ACOT7, ARF3, BTBD10, BTBD2, DUSP8, FHL2, GSDMD, HADH, KEAP1, LAMP1, PMVK, PPP1R18, RC3H2, SFXN1, SMARCE1, SYT6, TAGLN3, USP15, ACAA1, ACSS2, ADAMTS16, AHNAK, AK2, ALKBH5, APBB1IP, APOL1, APOM, ARHGAP1, ATP13A2, ATP8B5P, BAD, BAP1, BAZ2A, BNC2, BRPF1, BTRC, BYSL, BZRAP1, C17orf70, C1orf144, C20orf3, C21orf2, C5orf55, C8orf33, CALB2, CBLC, CCDC137, CCDC77, CCNDBP1, CD40LG, CDK16, CENPT, CERK, CFP, CHD4, CHMP4B, COL1A2, COL6A1, COQ6, CPNE1, CRIPAK, CSK, CTTN, DAZAP2, DBNL, DCTN1, DDX20, DDX51, DEDD2, DNAJC13, DNMT1, DOCK2, DPYSL3, DRAP1, DUSP10, EGR2, EIF2S2, EIF3A, EIF5A, EIF5B, ENTPD4, ESYT1, FAM160B2, FAM60A, FIGNL1, FOXK1, FUT8, GIMAP5, GNB2, GOLGA4, GOLM1, GPATCH1, GYG1, GYS1, HADHA, HBP1, HNRNPH3, HNRNPL, HYOU1, IARS2, IKZF5, IL2RG, IRF4, ISG15, IST1 (includes EG:307833), JUP, KAT7, KCNN4, KIAA0319L, KIF2A, KPNA2, KSR1, LAG3, LANCL2, LARP1, LENG3, LGMN, LRSAM1, MALT1, MAPK8IP3, MAST4, MAT2A, ME3, MED13, MED8 (includes EG:112950), MICALL2, MIIP, MLH1, MLL2, MLST8, MRPL49 (includes EG:18120), NARF, NFX1, NHSL1, NOLC1, NOTCH1, NPIPL3, NUP93, ODC1, PEX5, PEX6 (includes EG:117265), PHC1, PHF14, PHF20, PLEKHB2, PLEKHJ1, PLEKHM1P, PMF1, POLR1D, POM121, PPA1, PPP2R2B, PPRC1, PRKCSH, PSMD1, PTBP1, R3HDM2, RAD52 (includes EG:100426645), RANGAP1, RARA, RASSF5, RELB, RIPK1, RNF114, RPL22, RPLP0P2, RPS18, RPS6KA1, RPTOR, RSL24D1, SCAF11, SEC16A, SETD1B, SETX, SHE, SKIV2L, SLC1A5, SLC4A3, SLC7A5, SMARCB1, SNF8, SON, SPG20, SPINT1, SPNS2, SPRR3, SRSF7, SS18, SSBP4, STIM2, STK10, STOML2, SURF6, SUSD2, TACC3, TADA2B, TAF1 (includes EG:270627), TALDO1, TAOK2, TAP2, TBC1D1, TBCC, TCHP, TNFAIP8L2, TNKS, TNKS1BP1, TNRC6B, TOR1A, TRADD, TRAF3IP3, TRIAP1, TRIM66, TSHZ1, TUBGCP6, UBR4, UTY, VAV1, VCAN, VPS11, WBP2, WDR75, YTHDC1, ZC3H7A, ZC3HAV1, ZNF227, ZNF253, ZNF830, ZYX, CAP1, FAM189B, GSTM4, MRPL10 (includes EG:107732), NONO, OCIAD2, SRSF3, TANK, XPO4, ZNF638, ALKBH2, CCDC74A/CCDC74B, CLPTM1, EIF6, ERBB3, GREM1, GRWD1, ITGB2, JTB, MAGED2, MRPL23, NEFM, PSMC2, RAB3A, RPL10, RPL29 (includes EG:100039782), RUNDC3A, SEPT7, TCEAL2, TSPAN7, TXLNA, UBA1, USP10, ZNF192, ZNF284, CYFIP1, JPH3, PRPF4B, THAP7, ADAR, AFAP1, C19orf21, C22orf28, CDC5L, CEBPB (includes EG:1051), CNDP2, CPNE8, DIAPH1, DIEXF, DPP3, EXOSC7, FKBP9L, GLG1 (includes EG:20340), GLUL, GSTM2, HAUS4, HSP90AB1, KDM3B, KRBA1, LAS1L, LCK, MED13L, MPDU1, MTHFD2, MUC1, NUCB1, PCID2, PEBP1, PPP1R26, PRKCQ, PTOV1, RASGRP2, RGS2 (includes EG:19735), RPL36, RRP36 (includes EG:100360664), SEMA3F, SGCB, SIRT2, SMPD1, TCF7, TESC, TRIM24, USP11, YAF2, and/or ZNF256 or any combination thereof, in the patient.

3. The method of claim 1, wherein the one or more markers comprise A2M, AATK, ACBD5, ACO2 (includes EG:11429), ADAMDEC1, ADH5 (includes EG:100145871), ADI1 (includes EG:104923), AGRN, AGT, AKAP13, AKAP8, ALDOA, ALKBH2, ANAPC2, ANKRD11, ANKRD12, ANKRD13B, ANXA6, AP1G1, AP1M1, AP2M1, APBB1, APLP1, ARCN1, ARFRP1, ARHGAP30, ARHGDIA, ARHGEF1, ARHGEF18, ASAP1, ATG16L1, ATP5O, ATRX, ATXN2L, AZGP1, B3GNT1, BACE1, BAZ1A, BCAS2, BICD2, BNIP3L, BRD2, C10orf35, C11orf2, C11orf30, C11orf68, C12orf32, C19orf43, C19orf66, C1QTNF4, C7orf41, CAP1, CBX4, CCDC74A/CCDC74B, CCDC88A, CCDC88C, CCT5, CCT8, CD2BP2, CD74, CD81, CDC42EP3, CDCA4, CEP250, CFDP1, CHST10, CLDN5, CLIP1, CLPTM1, CLTC, CLUAP1, CNBP, CNPPD1, COG4, COL4A1, COL6A3, COMP, COPA, COPE, COPSE, CORO2A, CORO7/CORO7-PAM16, CPE, CSTB, CTAGE5, CTBP2, CTC1, CTPS1, CULT, CYCS, CYFIP1, D2HGDH, DAGLB, DALRD3, DDX10, DDX41, DDX54, DHX35, DLG5, DNAJB1, DNTTIP2, DUSP2, EDARADD, EDC4, EIF3M, EIF6, EML3, EPS8, ERBB3, ERCC5, EXOSC10, FABP7, FAM189B, FAM192A, FAM213A, FAM21A/FAM21C, FASN, FBF1, FBXW5, FGFBP3, FGFR3, FLOT1, FLYWCH1, FOSL2, FPGS, FYN, G3BP2, GABBR1, GEN1, GGA1 (includes EG:106039), GGA2, GLOD4, GNAI2, GNPDA1, GOLGA7, GOLGA8A/GOLGA8B, GOLGB1, GREM1, GRN, GRWD1, GSTM4, H1F0, HAUS7, HDAC2, HERC2, HLA-C, HLA-E, HMGB2, HNRNPAB, HNRNPM, HOXB2, HSP90AA1, HSPA5, HSPA8, HSPG2, ID3, IGHG1, IL16, IL1B, IMPDH2, INF2, ISOC1, ITFG3, ITGB2, ITPR3, JPH3, JTB, JUNB, KCTD15, KIAA1462, KIF5A, KRT19 (includes EG:16669), KRT73, LDHB (includes EG:3945), LOC341056, LRIG1, LRP1 (includes EG:16971), LRRC8B, LYSMD2, MAGED2, MAGI1, MAN2C1, MARCH2, MARS, MBD1, MBD4, MC1R, MDFIC, MED11 (includes EG:100148504), MED15, MED20, MED4 (includes EG:29079), MEGF6, METAP2, MGA, MICAL1, MINA, MORF4L1, MRPL10 (includes EG:107732), MRPL23, MRPS18C, MUC2 (includes EG:4583), NAGLU, NAP1L1, NARS2, NCOA3, NECAP1, NEDD9, NEFM, NEK1, NFATC1, NFKB1, NFKBIA, NFYA, NLRC5, NLRP1, NOL11, NONO, NOTCH2, NPHP3, NPLOC4, NR1H2, NSMCE1, NSUN5P1, NUMBL, OCIAD2, OLFML3, OTUD1, OTUD4, PAM, PARP14, PCBP1, PFKL, PHF23, PHIP, PIGT, PIK3R5, PIN1, PKM, PLCG1, POLR2B, POLR2J4, POTEE/POTEF, PPM1G, PPP1CA, PPP1R15A, PPP1R15B, PPP4C, PPP6R1, PRC1 (includes EG:233406), PRKAG1, PRMT1, PRPF4B, PRRC2A, PRSS53, PSAP, PSMA1, PSMB5, PSMC2, PSMC4, PSMC5, PSME4, QARS, R3HCC1, RAB3A, RABGGTB, RAI1 RAP2B, RASAL3, RCSD1, RECQL, RFC1, RIC8A, RNF39, RNF4, RPL10, RPL13, RPL18, RPL29 (includes EG:100039782), RPL9, RPS19, RPS25, RPS4Y2, RRP1B, RRP9, RSBN1, RTKN, RUNDC3A, S100A9, SAMHD1, SBK1, SCAF1, SCML4, SEPT7, SERPINF1, SETD2, SFN, SGK2, SIPA1, SIPA1L1, SIPA1L3, SIRT7, SLC4A2, SLC9A3R2, SMG5, SMYD5, SNCB, SND1, SNRNP48, SNRPF, SORD, SOX4, SPHK2, SPTBN1, SPTBN4, SRA1, SREBF2, SRM, SRPR, SRRM2, SRSF2, SRSF3, STAG1, STAG2, STAT1, STAT3, SUMO1P3, SYT1 (includes EG:20979), TANK, TAPBPL, TBCB, TBX21, TCEAL2, TFRC, TGOLN2, THAP7, TIAM1, TKT, TMC8, TMEM154, TMEM160, TMEM222, TMUB2, TOMM20 (includes EG:100043869), TP53 (includes EG:22059), TP53BP2, TRAK1, TRAP1, TREX1, TRIM28, TRIM78P, TRIOBP, TRIP12, TSPAN7, TSR1, TUBGCP3, TWF2, TXLNA, TXN2, U2AF1, U2SURP, UBA1, UBAP1, UBFD1, UBXN1, UQCRC1, USP10, USP30, USP42, USP7, UTP14A, UXT, VAT1, VIMP, WBP11, WDR24, WDR33, WDR73, WHSC2, WNK2, XPO1, XPO4, YLPM1, YWHAE, YWHAQ, ZAP70, ZC3H13, ZEB1, ZFPL1, ZMIZ2, ZNF192, ZNF284, ZNF335, ZNF358, ZNF554, ZNF629, ZNF638, ZNF837, and/or ZNFX1.

4. The method of claim 2, wherein the markers are selected from AAMP, AATK, AGRN, AHCY, AKR1A1, AKR7A2, AKT3, ANKRD24, ANXA1, ANXA11, ANXA6, AP1M1, AP2M1, AP3D1, ARCN1, ARL6IP4, ARPC4, ASAP1, ASMTL, ASNSD1, ATP1A3, ATP5H, ATRX, BBS2, BEX4, BRF2, BRK1, BZW1, C10orf35, C14orf129, C17orf101, C19orf66, C1QTNF4, C3orf19, C9orf16, CALR, CBWD1, CCDC86, CCT3, CDC123, CDKN2D, CEP250, CIAO1, CNBP, CORO1A, COX6B1, CSTB, CSTF2T, CUL7, DALRD3, DDR1, DDX19B, DNAJA1, DNMBP, DNTTIP2, DYNC1H1, EIF1, EIF2A, ELK1, EME2, EPHB3, EZR, F5, FAM120A, FAM13A, FAM192A, FAM208B, FAM32A, FAM40A, FAM65B, FKBP15, FLYWCH1, FNDC3A, FOXP4, GANAB, GART, GBE1, GGA1 (includes EG:106039), GPS1, GPSM1, HAPLN3, HDAC10, HECTD1, HIST1H1C, HMGN2, HNRNPA2B1, HNRNPC, HOOK2, HOXB3, HSF1 (includes EG:15499), IBA57 (includes EG:100330979), IGF2, IGFBP6, INPP5E, INTS1, INTS9, ITGA6, KCTD15, KHDRBS1, KIF13B, KIF1C, KLC4, KLHDC3, LAMB1, LAMC2, LARP4, LCP2, LOC285463, LRP1 (includes EG:16971), LRPAP1, LRRC37A3, MAD1L1, MAP1A, MARS, MAST1, MATK, MBD3 (includes EG:17192), MC1R, MCM2, MCM6, MED15, MEGF6, MEPCE, MLL3, MORC2, MPST, MTCH2, MUC2 (includes EG:4583), N4BP3, NAGLU, NAV2, NCOA4, NDST2, NDUFS7, NELF, NFKB1, NHEJ1, NKRF, NOL11, NR1H2, NT5C3L, NUDT5, OGFR, 0S9, PARP1, PCDH7, PCGF2, PFAS, PJA2, PLCG1, PLXNB2, PODXL2, PPP1CA, PPP1R15A, PPP4C, PPP6R1, PRDX5, PREP, PRKAG1, PSMB1, PSMB8, PSMC4, PTPN1, RALBP1, RANBP2, RAP1GAP, RAPGEF1, RASSF7, RCSD1, RFC1, RIC8A, RNF13, RPL10A, RPL18, RPL37A, RPP40, RPS25, SAMD1, SAP30BP, SDHB, SEC13, SEL1L3, SERBP1, SERINC2, SERPINF1, SETD2, SF3B3, SFI1 (includes EG:305467), SGCE, SH3BGRL3, SHCBP1, SHKBP1, SIPA1L1, SIVA1, SLC35A2, SMCHD1, SMG5, SNCB, SNRNP48, SNX15, SOX4, SPTBN1, SRA1, SSRP1, SSSCA1, ST3GAL3, STATE, STRN4, STX16, STX18, SUMF2, SUMO1P3, SYTL1, TACC2, TBC1D10B, TGS1, TMEM222, TMEM230, TMEM59L, TMEM8A, TMSB10/TMSB4X, TP53 (includes EG:22059), TPM3, TRAF2, TRAF4, TRAK1, TRIM28, TRIOBP, TRPS1, TSC22D3, TWF2, U2SURP, UBE2J2, UCHL3, UFD1L, UQCRC2, USP30, VIMP, VPS72 (includes EG:100001285), VRK1, WAPAL, WDR11, WHSC2, XAF1, ZFP36L2, ZFPL1, ZMYM2, ZNF146, ZNF439, and ZNRF1.

5. The method of claim 2, wherein the markers are selected from ACSS1, AHSG, AKAP11, AKAP9, AKR1B1, ANAPC2, ANKRD11, ANKRD44, ANXA6, APOBR, ARHGAP30, ARHGEF1, ARID1B, ATP5SL, ATXN3, ATXN7L2, BCL11A, BIN3, BMS1, BRD2, C11orf68, C12orf32, C12orf35, C17orf101, C19orf43, C2orf29, CAPN2, CASP1, CCDC56, CCT3, CCT6A, CD81, CDC123, CELF3, CFDP1, CHD3, CHMP1A, CLDN5, CLIP1, CLN6 (includes EG:315746), CLNS1A, CNOT2, COBRA1, COL4A1, CORO7/CORO7-PAM16, CREM (includes EG:12916), CRIP1, CSNK2B, CTPS1, CULT, DDOST, DDR1, DDX10, DDX54, DEF6, DENND5A, DENR, DHX16, DIP2C, DNAJA4, DNAJC11, DNLZ, DYNC1I2, ECSCR, EEF1A2, EIF2A, EIF2B4, EIF3G, EIF4A2, EPN2, EPS8L3, ERCC5, EZR, FAM208A, FAM32A, FAM59A, FAM65B, FAM73A, FASN, FBXW5, FGFR3, FLII, FNTB, GBP5, GJA9, GLE1 (includes EG:2733), GLRX3, GNAI2, GNL3, GPR56, GRN, HDAC3, HDAC6, HDLBP, HERC2, HINT1, HLA-B, HNRNPA1, HNRNPUL1, HNRPDL, IGF2R, IGHG1, IGH-MBP2, IL17RA, INPP5D, ITFG3, KARS, KAT6B, KCNJ14, KIAA0947, KRT73, L3MBTL2, LCAT, LDB1, LIN7C, LOC100130899, LOC285463, LOC389705, LOC440354, LOC494127, LOC644762, LPPR3, LRRC47, LRWD1, LTBP3, MAGED4/MAGED4B, MAGI1, MAN2B1, MAP1B, MAP7D1, MAPK6, MAPK8IP1, MBD3 (includes EG:17192), MCRS1, MEAF6, MLL, MLL4, MPP3, MVD, MYH9 (includes EG:17886), NARS, NBPF15, NCKAP5L, NCL, NCOA3, NELL2, NFATC1, NFIC, NFKB1, NMT1, NNAT, NOL11, NOMO1, NOTCH2, NPHP3, OBSCN, OGFR, OS9, OSTM1, PABPC1, PAIP1, PANK4, PARP1, PCBP1, PEPD, PES1, PFKM, PHF3, PIGQ, PIK3R2, PIPSL, PKD1, PKN1, PLCB3, PLCL2, PLD3, PLXNA2, PMPCB, PNMA1, PNN, POLR2J, PPBP, PPP1R13B, PPP1R15A, PPP6R1, PRC1 (includes EG:233406), PRDM8, PRDX1, PRPF19, PRPF3, PRPF8, PRRT1, PSD4, PSMB8, PSME1, PSMF1, PTGS2, PTPN4, RABGGTB, RAIL RARS2, RBL2 (includes EG:100331892), RBM15, RBM39, RERE, RFX5, RGS14, RNF166, RNF39, RPL15, RPL18, RPL26, RPL28, RPP40, RPS10, RPS19, RSL1D1, SAP18, SCHIP1, SDHB, SEC24B, SENP2, SETD2, SF3B2, SGSM3, SGTA, SH2D2A, SKIV2L2, SLC3A2, SLC9A3R2, SMC1A, SMEK2, SMG6, SNCB, SND1, SNRPD3, SPAG7, SPECC1L, SPG7, SRA1, SRSF1, SRSF4, STAU1, SYNPO, SYP, TADA3, TAF1C, TAP1, TAX1BP1, TBX21, TCEA2, THBS1, TPM3, TRIM44, TRIOBP, TRNAU1AP, TSEN54, TUBA1B, TXN2, TXNIP, U2SURP, UBAP2L, UBE2D2, UBE2D4, UBE2Q1, UBE4A, UFD1L, UIMC1, USP7, UTP14A, UVSSA, WDR6, WDR90, WRB, XBP1 (includes EG:140614), YARS, YTHDF1, ZBTB22, ZC3H13, ZC3H7B, ZEB1, ZFYVE28, ZNF668, ZNF837, ZNFX1.

6. The method of claim 1, wherein the one or more markers comprise ACBD5, ACTR1B, ADH5 (includes EG:100145871), AEBP1, AKNA, ALB, ANKIB1, ANKRD54, ANXA6, ANXA7, AP2M1, AP3D1, APBA2, ARAF, ARHGEF11, ARID5A, ATP5H, ATP6AP1, ATRX, BAG1, BCL6, BCL9, BCR, BEX4, BIN3, BIRC5, BTBD6, C17orf28, C17orf56, C9orf86, CACNB3, CBWD1, CC2D1A (includes EG:212139), CCND1, CCT6A, CD74, CD97, CDC37, CDC42BPB, CDCA4, CENPB, CEP192, CEP76, CHCHD7, CHD8, CHKB, CISH, CLIC1, CLK1, CNPPD1, COA5, COG4, COL3A1, COMMD7, COMMD9, CORO2A, CPE, CRAT, CSRP1, CTPS1, CTSK, CYTIP, DCAF6, DDX24, DDX39B, DHX16, DIRAS3, DLD, DMPK, DNM2, DOT1L, ECSCR, EDARADD, EDF1, EEF1D, EFR3A, EIF1, EIF3D, EIF3M, ELAVL4, ENTPD6, EPN1, EPS8, EPS8L2, ERBB2, ERCC3, EXOSC10, EXT2, FAM181A, FAM21B, FBLL1, FBXL17, FBXW5, FGFBP3, FURIN, GABARAPL2, GART, GJA9, GON4L, GPR98, GRN, GTF3C1, HAPLN3, HIC1, HIVEP2, HNRNPUL1, HSPA1A/HSPA1B, HSPA5, HSPA9, HSPG2, ILF3, IMPDH2, INPP5E, INPPL1, IP6K1, IQGAP2, ITFG3, IWS1, KCTD15, KIF21B, KIF22, KIF4A, KLF4, KLF6, KLHL23/PHOSPHO2-KLHL23, LAMA5, LAT, LAT2, LCMT1, LMF2, LMO4, LOC285463, LOC341056, LOXL2, MAGED4/MAGED4B, MAGI2, MARCH2, MARS, MAZ, MCM3AP, MED11 (includes EG:100148504), METTL3, MKLN1, MOB4, MPST, MRPS24, MRPS9 (includes EG:301371), MSLN, MTA1, MUC5AC/MUC5B, MYCBP2, NAP1L1, NARFL, NBPF15, NDUFAB1, NECAP1, NEK1, NEUROD2, NFATC4, NFKB1, NFKBIA, NIP7, NOA1, NOL11, NOL12, NPEPL1, NRAS (includes EG:18176), NXPH3, OFD1, OPA1, P4HB, PA2G4, PARP1, PCBP1, PEF1, PHAX, PHC2, PHF1, PHF3, PIN1, PKP3, PLXNB1, POLR2A, POLR2B, POLR2J4, PPM1F, PPP1R1B, PPP1R8, PRDX1, PRKAR2A, PRPF31, PSMB5, PSMD6, PSMF1, PSTPIP1, PTP4A3, PTPRA, PUF60, QSOX2, RAB43, RABGGTB, RALGDS, RASSF1, RCSD1, RFC1, RFX5, RNF135, RPAP2, RPL18A, RPL26, RPL36A, RPS17/RPS17L, RUSC2, SAP30BP, SART3, SCAF4, SEC13, SECISBP2, SEPN1, SF3B2, SGSM3, SIAH1, SLC35A2, SLC35B2, SLC44A2, SMURF2, SNCB, SNX1, SRCAP, SREBF2, SRSF2, SSH3, STAM, SUMO1P3, SUPV3L1, SYNE2, SYNPO, TARS2, TGOLN2, TGS1, TMEM160, TMEM173, TMEM184B, TMEM43, TMSB10/TMSB4X, TOMM34, TP53 (includes EG:22059), TPI1P2, TRIM28, TRIOBP, TSC2, TTC27, TTYH1, TUBB4B, U2AF1, U2SURP, UBE2J2, UBXN4, UNK, UQCRC1, USP39, VBP1, VDAC1, WBP11, WSB1, ZC3H13, ZCCHC9, ZNF12, ZNF260, ZNF428, ZNF439, ZNF574, and/or ZNF592.

7. The method of claim 1, wherein the one or more markers comprise AACS, AAMP, ABT1, ACO2 (includes EG:11429), ACOT7, ACTB, ACTN4, ACTR1B, ADI1 (includes EG:104923), AGT, AHCTF1, AIM1 (includes EG:11630), ALG3, ANKRD24, AP2M1, AP3D1, APBB1, APLP1, ARF3, ARHGDIA, ARHGEF6, ARID5A, ATF1 (includes EG:100040260), ATG13 (includes EG:362164), ATP1A3, ATRX, BCL11A, BEX4, BLMH, BTBD10, BTBD2, C10orf35, CARD11, CC2D1A (includes EG:212139), CD81, CDC27, CELF3, CEP70, CHD3, CHMP1A, CHMP1B, CIRH1A, CLASRP, CLC, CLIP1, CNKSR3, COPA, CRAMP1L, CRAT, CRYM, CSRNP1, CSTB, DAXX, DDR1, DDX27, DDX42, DDX56, DIDO1, DIRAS3, DNAJB1, DNAJC11, DSE, DUS3L, DUSP8, DVL2, DYNC1I2, EDC4, EIF3H, EIF4G1, EIF4H, ENTPD6, EPRS, EPS8, ETFA, EXOC6, EXOSC5, FADD, FAM192A, FAM21A/FAM21C, FAM40A, FAM59A, FASN, FBN3, FBRS, FBXO44, FEM1A, FHL2, FKBP10, FKBP1A, FYN, GEN1, GLOD4, GLRX3, GLTSCR1, GRN, GSDMD, GSK3A, HADH, HAX1, HINFP, HLA-A, HLA-B, HMGB2, HNRNPA2B1, HNRNPAB, HNRNPH1, HNRNPK, HNRNPR, IL32, INPP4A, INTS1, ISM1, ISOC1, ITFG3, ITK, KCTD15, KEAP1, KHDRBS1, KLF4, LAMA5, LAMB1, LAMP1, LOC285463, LONP1, LSM14A, LSP1 (includes EG:16985), MAP7D1, MAPK7, MAPK8IP1, MARK3, MAZ, MBD4, MFHAS1, MLH3 (includes EG:217716), MLL3, MSL1 (human), MSTO1, MTHFS, MTM1, MUS81, MYO1F, NAA25, NARFL, NARS2, NCAPG, NCOA4, NCOA6, NDFIP2, NDUFA10, NDUFS2, NECAP1, NET1 (includes EG:10276), NFKBIA, NFRKB, NIPAL3, NOL11, NOL12, NR1H2, NRBP1, NRXN2, NUDC, NUF2, NUMA1, NYNRIN, OBFC1, OGFR, OTUD1, PAAF1, PARP10, PDXDC1, PEPD, PEX1 (includes EG:100534854), PFKFB4, PFKM, PHC2, PIGQ, PIGR, PIPSL, PLEC, PMVK, PPID, PPL, PPP1CA, PPP1R18, PPP1R2, PPP4C, PRMT6, PRPF8, PRPS1, PRRC2C, PSMA1, PSMC4, PUF60, QARS, RAB14, RAD21, RAI1, RALBP1, RASSF1, RBM39, RC3H2, RCSD1, REV3L, RGS1, RIMBP3, RPL17, RPL7, RPL9, RPP40, RPS15, RPS17/RPS17L, RPS4Y2, S1PR4, SCML4, SCRIB, SCYL1, SDF4, SEC24C, SETD4, SF3A1, SFN, SFXN1, SH2D2A, SIL1 (includes EG:100334837), SIRT7, SKP1/SKP1P2, SLC3A2, SLC44A2, SLK, SMARCE1, SMC1A, SMG5, SNX17, SORD, SPTAN1, SRA1, SRRM2, STAB1, STAT4, SYNPO, SYT6, TAGLN3, TBC1D10A, TBCB, TBR1, TBX21, TFF1, TLE3 (includes EG:100007463), TMEM184B, TMEM199, TMEM222, TMUB2, TOE1, TP53 (includes EG:22059), TP53BP2, TPR, TRAK2, TRAP1, TRIM5, TSC2, TSPYL2, TUBA1B, TXNRD1, U2SURP, UBE2N, UFD1L, USP15, USP5, VAT1, VPS72 (includes EG:100001285), WASF1, WASL, XPO1, ZBTB40, ZC3H3 (includes EG:223642), ZEB1, ZNF333, ZNFX1, and/or ZXDC.

8. The method of claim 1, further defined as comprising detecting lung cancer in the patient by detecting a marker protein selected from ACO2 (includes EG:11429), ADH5 (includes EG:100145871), ADI1 (includes EG:104923), AGRN, AKAP13, AKR1C4, ALDOA, APBB1, ARHGDIA, ARHGEF1, ARHGEF18, ATXN2L, BAZ1A, BCAS2, C10orf35, CCDC88C, CD81, CEP250, CLDN5, COL4A1, COMP, COPE, CUL1, D2HGDH, DUSP2, EDARADD, EIF3M, EPS8, ERCC5, EXOSC10, FAM192A, FAM21A/FAM21C, FBF1, FGFR3, FPGS, FYN, G3BP2, GABBR1, GGA2, GLOD4, GOLGA7, HERC2, HLA-E, HMGB2, IGHG1, KCTD15, KIF5A, LRP1 (includes EG:16971), MC1R, MDFIC, MED20, MEGF6, MUC2 (includes EG:4583), NECAP1, NEDD9, NFKB1, NFKBIA, NFYA, NLRC5, NLRP1, NOL11, PCBP1, PLCG1, PPP1CA, PPP6R1, PRMT1, PSAP, PSMC4, RCSD1, RPS25, RRP1B, RSBN1, SBK1, SETD2, SFN, SLC9A3R2, SMYD5, SNCB, SNRNP48, SREBF2, SRPR, SRRM2, SUMO1P3, TBCB, TMEM222, TOMM20 (includes EG:100043869), TP53 (includes EG:22059), TP53BP2, TRAK1, TRIM28, TRIM78P, TRIOBP, TXN2, UQCRC1, UTP14A, VIMP, WNK2, ZC3H13, ZEB1, ACBD5, ADAMDEC1, AKAP8, ANKRD12, AP1G1, AP1M1, ARFRP1, ATG16L1, AZGP1, BACE1, BICD2, BRD2, C11orf30, C1QTNF4, CBX4, CD74, CHST10, CLIP1, CLTC, CLUAP1, COL6A3, COPA, CTBP2, DAGLB, DDX54, DLG5, DNAJB1, EML3, FBXW5, FLOT1, FOSL2, GGA1 (includes EG:106039), HAUS7, HOXB2, HSPA8, HSPG2, ID3, IL1B, IMPDH2, ISOC1, ITFG3, KRT73, LOC341056, LYSMD2, MED11 (includes EG:100148504), MED4 (includes EG:29079), METAP2, NAP1L1, NFATC1, NOTCH2, NPHP3, NR1H2, NSMCE1, NUMBL, OTUD4, PARP14, PFKL, PKM, POTEE/POTEF, PPP1R15B, PPP4C, PRC1 (includes EG:233406), PRRC2A, PSMA1, PSMB5, PSME4, QARS, RAI1 RAP2B, RASAL3, RECQL, RNF39, RPS19, SCAF1, SCML4, SMG5, SNRPF, STAG2, TAPBPL, TBX21, TFRC, TGOLN2, TIAM1, TMC8, TMEM154, UBFD1, VAT1, YLPM1, YWHAE, YWHAQ, ZAP70, ZNF837, AGT, AP2M1, APLP1, ARCN1, ASAP1, B3GNT1, BNIP3L, C12orf32, C19orf66, CCT8, CDC42EP3, CFDP1, CNBP, COG4, COPSE, CORO2A, CTPS1, CYCS, DALRD3, DDX10, DDX41, DHX35, FABP7, FASN, FLYWCH1, GNAI2, GNPDA1, H1F0, HNRNPAB, HSPA5, IL16, ITPR3, JUNB, LRRC8B, MARCH2, MBD1, MORF4L1, NAGLU, NCOA3, NEK1, NPLOC4, NSUN5P1, OLFML3, PAM, PHF23, PHIP, PIN1, PPM1G, R3HCC1, RABGGTB, RFC1, RIC8A, RPL18, RPS4Y2, RTKN, SAMHD1, SGK2, SND1, SPHK2, SPTBN4, STAG1, STAT3, TMUB2, TRAP1, TSR1, U2SURP, USP7, WBP11, WDR24, WDR33, WDR73, ZNF554, ZNFX1, A2M, AATK, ANAPC2, ANKRD11, ANKRD13B, ARHGAP30, ATP5O, ATRX, C11orf2, C11orf68, C19orf43, C7orf41, CCDC88A, CCT5, CD2BP2, CNPPD1, CPE, CSTB, CTAGE5, CTC1, DNTTIP2, FAM213A, FGFBP3, GEN1, GOLGA8A/GOLGA8B, GOLGB1, GRN, HDAC2, HLA-C, HNRNPM, HSP90AA1, INF2, KIAA1462, KRT19 (includes EG:16669), LDHB (includes EG:3945), LRIG1, MAGI1, MAN2C1, MARS, MED15, MGA, MICAL1, MINA, MRPS18C, PIGT, PIK3R5, POLR2J4, PPP1R15A, PRKAG1, PRSS53, PSMC5, RNF4, RPL13, RRP9, S100A9, SIPA1, SIPA1L3, SLC4A2, SOX4, SPTBN1, SRA1, SRM, SRSF2, STAT1, SYT1 (includes EG:20979), TKT, TREX1, TRIP12, TUBGCP3, TWF2, UBAP1, UBXN1, USP30, USP42, UXT, ZFPL1, ZMIZ2, ZNF335, ZNF358, ZNF629, AAMP, AHCY, ANXA11, ANXA6, ARL6IP4, ARPC4, ASMTL, ATP5H, BBS2, BEX4, C14orf129, C9orf16, CALR, CCT3, CDC123, DDR1, DDX19B, DNMBP, ELK1, EPHB3, F5, FAM208B, FKBP15, GANAB, GBE1, GPSM1, HIST1H1C, HNRNPC, HOOK2, IGF2, IGFBP6, INTS1, INTS9, LAMB1, LAMC2, LCP2, LRPAP1, MATK, MBD3 (includes EG:17192), MORC2, NAV2, NELF, NKRF, OGFR, PCDH7, PCGF2, PLXNB2, PODXL2, PRDX5, PSMB1, PSMB8, RAPGEF1, RPL37A, RPP40, SEL1L3, SFI1 (includes EG:305467), SH3BGRL3, SIVA1, SLC35A2, STATE, STRN4, STX16, SUMF2, SYTL1, TBC1D10B, TMEM230, TSC22D3, VRK1, WAPAL, ZNF146, ZNRF1, AKT3, ASNSD1, ATP1A3, BRK1, BZW1, C17orf101, CDKN2D, CIAO1, EIF1, EZR, FAM13A, FAM40A, FAM65B, HAPLN3, HECTD1, KIF13B, LRRC37A3, MAD1L1, MEPCE, NDUFS7, OS9, PARP1, PREP, RALBP1, RAP1GAP, SERINC2, SHKBP1, SSRP1, TGS1, TPM3, TRPS1, UCHL3, UQCRC2, WDR11, XAF1, AP3D1, C3orf19, CCDC86, DNAJA1, DYNC1H1, FAM120A, FAM32A, FNDC3A, FOXP4, HDAC10, HMGN2, HNRNPA2B1, HOXB3, HSF1 (includes EG:15499), IBA57 (includes EG:100330979), KHDRBS1, LARP4, MAP1A, MAST1, MCM6, MPST, NCOA4, NT5C3L, PTPN1, RASSF7, RPL10A, SAMD1, SDHB, SIPA1L1, SSSCA1, UBE2J2, ZMYM2, AKR1A1, AKR7A2, ANKRD24, ANXA1, BRF2, CBWD1, COX6B1, CSTF2T, EIF2A, EME2, GART, GPS1, INPP5E, ITGA6, KIF1C, LOC285463, MCM2, MLL3, N4BP3, NDST2, NHEJ1, NUDT5, PFAS, PJA2, RANBP2, SAP30BP, SEC13, SERBP1, SF3B3, SHCBP1, SMCHD1, SNX15, TACC2, TMEM8A, TMSB10/TMSB4X, TRAF2, TRAF4, UFD1L, VPS72 (includes EG:100001285), ZFP36L2, CORO1A, KLC4, KLHDC3, MTCH2, RNF13, SERPINF1, SGCE, ST3GAL3, STX18, TMEM59L, WHSC2, ZNF439, AKR1B1, APOBR, ARID1B, ATP5SL, BCL11A, C2orf29, CAPN2, CHMP1A, CLN6 (includes EG:315746), CLNS1A, CORO7/CORO7-PAM16, DHX16, DYNC1I2, ECSCR, EEF1A2, EIF3G, EPS8L3, FAM208A, FAM73A, GBP5, GLRX3, HNRNPA1, HNRPDL, IL17RA, L3MBTL2, LDB1, LOC494127, LOC644762, LPPR3, MAGED4/MAGED4B, MAP1B, MAPK6, MCRS1, MLL, NARS, NCL, PAIP1, PEPD, PES1, PLCB3, PLXNA2, POLR2J, PRDX1, PRPF3, PRPF8, PSD4, PSMF1, PTPN4, RARS2, RBM39, RFX5, RGS14, RNF166, RPL26, RPL28, SH2D2A, SPAG7, TAX1BP1, TCEA2, TUBA1B, TXNIP, UBE2D2, UBE2Q1, WDR6, WDR90, XBP1 (includes EG:140614), ACSS1, ANKRD44, ATXN3, COBRA1, DNAJA4, DNAJC11, GLE1 (includes EG:2733), GNL3, HDAC3, HDAC6, HDLBP, HINT1, HNRNPUL1, IGF2R, KCNJ14, LIN7C, NELL2, NMT1, PLCL2, PLD3, PNMA1, PPP1R13B, RSL1D1, SEC24B, SLC3A2, SMC1A, TAP1, TSEN54, UVSSA, WRB, ZC3H7B, ATXN7L2, BMS1, CCDC56, CHD3, DDOST, DENND5A, EIF2B4, EPN2, KAT6B, LTBP3, MAPK8IP1, MEAF6, MLL4, MPP3, NCKAP5L, NNAT, PIK3R2, PKD1, PKN1, PPBP, RPL15, SENP2, SGSM3, SKIV2L2, SMG6, SNRPD3, SYP, TADA3, ZBTB22, AKAP11, AKAP9, BIN3, C12orf35, CNOT2, CREM (includes EG:12916), CRIP1, CSNK2B, DEF6, DENR, DIP2C, DNLZ, FAM59A, GJA9, HLA-B, IGHMBP2, KARS, KIAA0947, LOC100130899, LOC389705, LOC440354, MAN2B1, MAP7D1, MVD, OBSCN, OSTM1, PABPC1, PHF3, PIPSL, PRDM8, PRPF19, PRRT1, PSME1, PTGS2, RBM15, RERE, RPS10, SAP18, SCHIP1, SF3B2, SMEK2, SPECC1L, SPG7, SRSF4, SYNPO, TAF1C, THBS1, TRIM44, TRNAU1AP, UBAP2L, UIMC1, YARS, YTHDF1, ZFYVE28, ZNF668, AHSG, CASP1, CCT6A, CELF3, EIF4A2, FLII, FNTB, GPR56, INPP5D, LCAT, LRRC47, LRWD1, MYH9 (includes EG:17886), NBPF15, NFIC, NOMO1, PANK4, PFKM, PIGQ, PMPCB, PNN, RBL2 (includes EG:100331892), SGTA, SRSF1, STAU1, UBE2D4, UBE4A, ACTR1B, AEBP1, ARID5A, ATP6AP1, BTBD6, CDC37, CDC42BPB, CDCA4, CENPB, CEP192, COMMD7, CRAT, CSRP1, CTSK, DCAF6, DIRAS3, DMPK, EIF3D, ELAVL4, EPN1, ERBB2, ERCC3, FBLL1, FBXL17, FURIN, HIVEP2, INPPL1, IQGAP2, IWS1, LAT, LOXL2, MAGI2, METTL3, MKLN1, MRPS9 (includes EG:301371), MYCBP2, NARFL, NPEPL1, OFD1, P4HB, PHC2, PHF1, PRKAR2A, PSMD6, PSTPIP1, RASSF1, RPL18A, SEPN1, SIAH1, STAM, TMEM184B, TTYH1, TUBB4B, UNK, USP39, VDAC1, ZNF592, ANKIB1, ANKRD54, BCR, BIRC5, CACNB3, CC2D1A (includes EG:212139), CHD8, CLIC1, COA5, EDF1, EPS8L2, FAM21B, GON4L, ILF3, IP6K1, LCMT1, MSLN, NEUROD2, NFATC4, PHAX, POLR2B, PTP4A3, PTPRA, QSOX2, RPL36A, SLC35B2, SMURF2, SRCAP, SYNE2, TMEM43, U2AF1, VBP1, WSB1, ANXA7, ARHGEF11, BCL9, C17orf28, C17orf56, CHCHD7, CHKB, CISH, CLK1, CYTIP, DDX24, DDX39B, DNM2, DOT1L, EFR3A, EXT2, FAM181A, GPR98, HIC1, HSPA1A/HSPA1B, KIF21B, KIF22, KLF6, LAT2, LMF2, MTA1, NIP7, NXPH3, PA2G4, PLXNB1, PPP1R8, PUF60, RAB43, RALGDS, RPAP2, SLC44A2, SSH3, SUPV3L1, TMEM173, TSC2, UBXN4, ZCCHC9, ZNF12, ZNF260, AKNA, ALB, ARAF, BAG1, BCL6, C9orf86, CCND1, CD97, CEP76, COL3A1, COMMD9, DLD, ENTPD6, KLF4, KLHL23/PHOSPHO2-KLHL23, LAMA5, LMO4, MAZ, MUC5AC/MUC5B, NOA1, NOL12, NRAS (includes EG:18176), POLR2A, PPP1R1B, PRPF31, RNF135, RPS17/RPS17L, SART3, SCAF4, SECISBP2, SNX1, TARS2, TOMM34, TPI1P2, TTC27, ZNF428, ZNF574, APBA2, EEF1D, GABARAPL2, GTF3C1, HSPA9, KIF4A, MCM3AP, MOB4, MRPS24, NDUFAB1, OPA1, PEF1, PKP3, PPM1F, RUSC2, TMEM160, ABT1, ACTN4, BLMH, CEP70, CLASRP, CNKSR3, CRAMP1L, DUS3L, ETFA, FADD, FBRS, FKBP10, FKBP1A, HAX1, HINFP, HLA-A, HNRNPK, HNRNPR, INPP4A, ITK, LSM14A, LSP1 (includes EG:16985), MFHAS1, MLH3 (includes EG:217716), MSL1 (human), NAA25, NDUFA10, NDUFS2, NFRKB, NIPAL3, NUDC, NUMA1, OBFC1, OTUD1, PARP10, PEX1 (includes EG:100534854), PIGR, PPID, PRMT6, PRPS1, RAD21, RGS1, RPL17, RPS15, SEC24C, SF3A1, SIRT7, SKP1/SKP1P2, SLK, SPTAN1, STAB1, STAT4, TBC1D10A, TSPYL2, UBE2N, WASL, ZC3H3 (includes EG:223642), ZNF333, ZXDC, ACTB, AIM1 (includes EG:11630), CHMP1B, DVL2, EDC4, EXOSC5, FBN3, FBXO44, GSK3A, HNRNPH1, IL32, LONP1, MAPK7, MBD4, MSTO1, NARS2, NCAPG, NUF2, PPL, RPL9, SORD, TOE1, TRIM5, XPO1, ALG3, CARD11, CLC, DAXX, DDX27, DDX56, DSE, EIF4H, EXOC6, FEM1A, ISM1, MTM1, MUS81, MYO1F, NDFIP2, NET1 (includes EG:10276), NYNRIN, PDXDC1, PLEC, PRRC2C, RAB14, SCRIB, SCYL1, SETD4, SNX17, TBR1, TFF1, TXNRD1, AHCTF1, ARHGEF6, ATF1 (includes EG:100040260), ATG13 (includes EG:362164), CDC27, CIRH1A, CRYM, CSRNP1, DDX42, DIDO1, EIF3H, EIF4G1, EPRS, GLTSCR1, MARK3, MTHFS, NCOA6, NRBP1, NRXN2, PAAF1, PFKFB4, PPP1R2, REV3L, RIMBP3, RPL7, S1PR4, SDF4, SIL1 (includes EG:100334837), TLE3 (includes EG:100007463), TMEM199, TPR, TRAK2, USP5, WASF1, ZBTB40, AACS, ACOT7, ARF3, BTBD10, BTBD2, DUSP8, FHL2, GSDMD, HADH, KEAP1, LAMP1, PMVK, PPP1R18, RC3H2, SFXN1, SMARCE1, SYT6, TAGLN3, USP15, ACAA1, ACSS2, ADAMTS16, AHNAK, AK2, ALKBH5, APBB1IP, APOL1, APOM, ARHGAP1, ATP13A2, ATP8B5P, BAD, BAP1, BAZ2A, BNC2, BRPF1, BTRC, BYSL, BZRAP1, C17orf70, C1orf144, C20orf3, C21orf2, C5orf55, C8orf33, CALB2, CBLC, CCDC137, CCDC77, CCNDBP1, CD40LG, CDK16, CENPT, CERK, CFP, CHD4, CHMP4B, COL1A2, COL6A1, COQ6, CPNE1, CRIPAK, CSK, CTTN, DAZAP2, DBNL, DCTN1, DDX20, DDX51, DEDD2, DNAJC13, DNMT1, DOCK2, DPYSL3, DRAP1, DUSP10, EGR2, EIF2S2, EIF3A, EIF5A, EIF5B, ENTPD4, ESYT1, FAM160B2, FAM60A, FIGNL1, FOXK1, FUT8, GIMAP5, GNB2, GOLGA4, GOLM1, GPATCH1, GYG1, GYS1, HADHA, HBP1, HNRNPH3, HNRNPL, HYOU1, IARS2, IKZF5, IL2RG, IRF4, ISG15, IST1 (includes EG:307833), JUP, KAT7, KCNN4, KIAA0319L, KIF2A, KPNA2, KSR1, LAG3, LANCL2, LARP1, LENG8, LGMN, LRSAM1, MALT1, MAPK8IP3, MAST4, MAT2A, ME3, MED13, MED8 (includes EG:112950), MICALL2, MIIP, MLH1, MLL2, MLST8, MRPL49 (includes EG:18120), NARF, NFX1, NHSL1, NOLC1, NOTCH1, NPIPL3, NUP93, ODC1, PEX5, PEX6 (includes EG:117265), PHC1, PHF14, PHF20, PLEKHB2, PLEKHJ1, PLEKHM1P, PMF1, POLR1D, POM121, PPA1, PPP2R2B, PPRC1, PRKCSH, PSMD1, PTBP1, R3HDM2, RAD52 (includes EG:100426645), RANGAP1, RARA, RASSF5, RELB, RIPK1, RNF114, RPL22, RPLP0P2, RPS18, RPS6KA1, RPTOR, RSL24D1, SCAF11, SEC16A, SETD1B, SETX, SHE, SKIV2L, SLC1A5, SLC4A3, SLC7A5, SMARCB1, SNF8, SON, SPG20, SPINT1, SPNS2, SPRR3, SRSF7, SS18, SSBP4, STIM2, STK10, STOML2, SURF6, SUSD2, TACC3, TADA2B, TAF1 (includes EG:270627), TALDO1, TAOK2, TAP2, TBC1D1, TBCC, TCHP, TNFAIP8L2, TNKS, TNKS1BP1, TNRC6B, TOR1A, TRADD, TRAF3IP3, TRIAP1, TRIM66, TSHZ1, TUBGCP6, UBR4, UTY, VAV1, VCAN, VPS11, WBP2, WDR75, YTHDC1, ZC3H7A, ZC3HAV1, ZNF227, ZNF253, ZNF830, ZYX, CAP1, FAM189B, GSTM4, MRPL10 (includes EG:107732), NONO, OCIAD2, SRSF3, TANK, XPO4, ZNF638, ALKBH2, CCDC74A/CCDC74B, CLPTM1, EIF6, ERBB3, GREM1, GRWD1, ITGB2, JTB, MAGED2, MRPL23, NEFM, PSMC2, RAB3A, RPL10, RPL29 (includes EG:100039782), RUNDC3A, SEPT7, TCEAL2, TSPAN7, TXLNA, UBA1, USP10, ZNF192, ZNF284, CYFIP1, JPH3, PRPF4B, THAP7, ADAR, AFAP1, C19orf21, C22orf28, CDC5L, CEBPB (includes EG:1051), CNDP2, CPNE8, DIAPH1, DIEXF, DPP3, EXOSC7, FKBP9L, GLG1 (includes EG:20340), GLUL, GSTM2, HAUS4, HSP90AB1, KDM3B, KRBA1, LAS1L, LCK, MED13L, MPDU1, MTHFD2, MUC1, NUCB1, PCID2, PEBP1, PPP1R26, PRKCQ, PTOV1, RASGRP2, RGS2 (includes EG:19735), RPL36, RRP36 (includes EG:100360664), SEMA3F, SGCB, SIRT2, SMPD1, TCF7, TESC, TRIM24, USP11, YAF2, and/or ZNF256 in the patient.

9. The method claim 1, wherein the step of detecting autoantibodies binding antigenic fragments comprises detecting a detection signal and comparing said detection signal with detection signals of one or more known control samples from lung cancer.

10. A method of treating a patient having lung cancer, comprising detecting lung cancer in the patient using a method comprising the step of detecting autoantibodies that bind an antigenic fragment of one or more marker protein(s) in a sample from the patient, wherein the one or more marker protein(s) comprise AKR1C4, and removing said lung cancer.

\* \* \* \* \*

UNITED STATES PATENT AND TRADEMARK OFFICE
CERTIFICATE OF CORRECTION

PATENT NO. : 10,156,570 B2
APPLICATION NO. : 14/893712
DATED : December 18, 2018
INVENTOR(S) : Andreas Weinhäusel It is certified that error appears in the above-identified patent and that said Letters Patent is hereby corrected as shown below:

In the Claims

Claim 2, Column 55, Line 36:
Delete "CULT" and replace with -- CUL7 --.

Claim 2, Column 55, Line 64:
Delete "RAIL" and replace with -- RAI1 --.

Claim 2, Column 56, Line 3:
Delete "COPSE" and replace with -- COPS6 --.

Claim 2, Column 56, Line 37:
Delete "STATE" and replace with -- STAT6 --.

Claim 2, Column 57, Line 24:
Delete "5R5F4" and replace with -- SRSF4 --.

Claim 2, Column 57, Line 26:
Delete "FLIT" and replace with -- FLII --.

Claim 2, Column 58, Line 11:
Delete "TRIMS" and replace with -- TRIM8 --.

Claim 3, Column 59, Line 31:
Delete "COPSE" and replace with -- COPS6 --.

Claim 3, Column 59, Line 33:
Delete "CULT" and replace with -- CUL7 --.

Signed and Sealed this
Twelfth Day of March, 2019

Andrei Iancu
*Director of the United States Patent and Trademark Office*

Claim 3, Column 59, Line 67:
Delete "RAIL" and replace with -- RAI1 --.

Claim 4, Column 60, Line 51:
Delete "0S9" and replace with -- OS9 --.

Claim 4, Column 60, Line 62:
Delete "STATE" and replace with -- STAT6 --.

Claim 5, Column 61, Line 14:
Delete "CULT" and replace with -- CUL7 --.

Claim 5, Column 61, Line 34:
Delete "0S9" and replace with -- OS9 --.

Claim 5, Column 61, Line 41:
Delete "RAIL" and replace with -- RAI1 --.

Claim 7, Column 63, Line 21:
Delete "TRIMS" and replace with -- TRIM8 --.

Claim 8, Column 63, Line 33:
Delete "CULT" and replace with -- CUL7 --.

Claim 8, Column 63, Line 60:
Delete "RAIL" and replace with -- RAI1 --.

Claim 8, Column 63, Line 66:
Delete "COPSE" and replace with -- COPS6 --.

Claim 8, Column 64, Line 34:
Delete "STATE" and replace with -- STAT6 --.

Claim 8, Column 65, Line 23:
Delete "FLIT" and replace with -- FLII --.

Claim 8, Column 66, Line 8:
Delete "TRIMS" and replace with -- TRIM8 --.